US009895373B2

(12) United States Patent
Dar et al.

(10) Patent No.: US 9,895,373 B2
(45) Date of Patent: Feb. 20, 2018

(54) SUBSTITUTED PYRAZOLO[3,4-D]PYRIMIDINES AND USES THEREOF

(71) Applicants: The Regents of the University of California, Oakland, CA (US); Icahn School of Medicine at Mount Sinai, New York, NY (US)

(72) Inventors: Arvin C. Dar, San Francisco, CA (US); Tirtha K. Das, New York, NY (US); Martin Sos, San Francisco, CA (US); Trever G. Bivona, San Francisco, CA (US); Kevan M. Shokat, San Francisco, CA (US); Ross L. Cagan, New York, NY (US)

(73) Assignees: The Regents of the University of California, Oakland, CA (US); Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/078,657

(22) Filed: Mar. 23, 2016

(65) Prior Publication Data
US 2016/0354377 A1 Dec. 8, 2016

Related U.S. Application Data

(63) Continuation of application No. 14/189,742, filed on Feb. 25, 2014, now Pat. No. 9,321,772, which is a continuation of application No. PCT/US2012/053542, filed on Aug. 31, 2012.

(60) Provisional application No. 61/530,847, filed on Sep. 2, 2011, provisional application No. 61/606,296, filed on Mar. 2, 2012.

(51) Int. Cl.
*A61K 31/519* (2006.01)
*A61K 45/06* (2006.01)
*C07D 487/04* (2006.01)

(52) U.S. Cl.
CPC ............ *A61K 31/519* (2013.01); *A61K 45/06* (2013.01); *C07D 487/04* (2013.01)

(58) Field of Classification Search
CPC ............................ C07D 487/04; A61K 31/519
USPC ........................................ 514/262.1; 544/262
See application file for complete search history.

(56) References Cited

U.S. PATENT DOCUMENTS

| 4,704,381 A | 11/1987 | Schaumann et al. |
|---|---|---|
| 4,861,760 A | 8/1989 | Mazuel et al. |
| 4,911,920 A | 3/1990 | Jani et al. |
| 5,010,175 A | 4/1991 | Rutter et al. |
| 5,212,162 A | 5/1993 | Missel et al. |
| 5,240,941 A | 8/1993 | Bruneau |
| 5,288,514 A | 2/1994 | Ellman |
| 5,310,731 A | 5/1994 | Olsson et al. |
| 5,364,862 A | 11/1994 | Spada et al. |
| 5,403,841 A | 4/1995 | Lang et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,539,083 A | 7/1996 | Cook et al. |
| 5,561,134 A | 10/1996 | Spada et al. |
| 5,563,257 A | 10/1996 | Zilch et al. |
| 5,593,853 A | 1/1997 | Chen et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |

(Continued)

FOREIGN PATENT DOCUMENTS

| CA | 1338379 | 6/1996 |
|---|---|---|
| CN | 101602768 | 12/2009 |

(Continued)

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
West et al., "Activation of the PI3K/Akt pathway and chemotherapeutic resistance," Drug Resistance Updates, 5, 2002, 234-248.
International Preliminary Report on Patentability and Written Opinion dated Mar. 4, 2014 for International Application No. PCT/US2012/053542, 10 pages.

(Continued)

*Primary Examiner* — Kristin Vajda
(74) *Attorney, Agent, or Firm* — Zachary L. Terranova; Mintz, Levin, Cohn, Ferris, Glovsky and Popeo, P.C.

(57) ABSTRACT

Presented herein are novel therapeutic compounds and methods of using the same for the treatment of cancers.

19 Claims, 46 Drawing Sheets

(56) References Cited

U.S. PATENT DOCUMENTS

| | | |
|---|---|---|
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 8,697,709 B2 | 4/2014 | Dar et al. |
| 8,980,899 B2 | 3/2015 | Korennykh et al. |
| 9,321,772 B2 | 4/2016 | Dar et al. |
| 2001/0019829 A1 | 9/2001 | Nelson |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Balkrishen et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0208800 A1 | 3/2003 | Eby |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0153752 A1 | 8/2003 | Hirst et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043388 A1 | 3/2004 | Come et al. |
| 2004/0043983 A1 | 3/2004 | Li |
| 2004/0067901 A1 | 4/2004 | Balkrishen et al. |
| 2004/0067915 A1 | 4/2004 | McMahon et al. |
| 2004/0072766 A1 | 4/2004 | June |
| 2004/0072788 A1 | 4/2004 | Balkrishen et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |

(56) References Cited

U.S. PATENT DOCUMENTS

| | | |
|---|---|---|
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0239820 A1 | 10/2005 | Borzilleri et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0035912 A1 | 2/2006 | Marx et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Milian et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0294930 A1 | 11/2012 | Ren et al. |
| 2012/0322814 A1 | 12/2012 | Korennykh et al. |
| 2012/0329776 A1 | 12/2012 | Ren et al. |

FOREIGN PATENT DOCUMENTS

| | | |
|---|---|---|
| EP | 773023 A1 | 5/1997 |
| EP | 1020445 B1 | 8/2008 |
| GB | 812366 | 4/1959 |
| GB | 937725 | 9/1963 |
| JP | 61109797 | 5/1986 |
| JP | 5256693 | 10/1993 |
| JP | 8295667 | 11/1996 |
| JP | 9143163 | 6/1997 |
| JP | 10-506624 | 6/1998 |
| JP | 10206995 | 8/1998 |
| JP | 2000-072773 A | 3/2000 |
| JP | 2001-1516353 A | 9/2001 |
| JP | 2002-037787 A | 2/2002 |
| JP | 2002-131859 | 5/2002 |
| JP | 2002-131859 A2 | 5/2002 |
| JP | 2002-526500 A | 8/2002 |
| JP | 2002-527359 A | 8/2002 |
| JP | 2003-073357 A | 3/2003 |
| JP | 2003-073357 A2 | 3/2003 |
| JP | 2003-509428 A | 3/2003 |
| JP | 2004-514405 A | 5/2004 |
| JP | 2004-161716 A | 6/2004 |
| JP | 2004-531513 A | 10/2004 |
| JP | 2005-501811 A | 1/2005 |
| JP | 2006-512356 A | 4/2006 |
| JP | 2007-511596 A | 5/2007 |
| JP | 2007-520559 A | 7/2007 |
| JP | 2008-500330 A | 1/2008 |
| JP | 2008-533172 A | 8/2008 |
| WO | WO-83/01446 A1 | 4/1983 |
| WO | WO-91/17161 A1 | 11/1991 |
| WO | WO-91/19735 A1 | 12/1991 |
| WO | WO-92/00091 A1 | 1/1992 |
| WO | WO-92/14733 A1 | 9/1992 |
| WO | WO-93/16091 A1 | 8/1993 |
| WO | WO-93/16092 A1 | 8/1993 |
| WO | WO-93/18035 A1 | 9/1993 |
| WO | WO-93/20242 A1 | 10/1993 |
| WO | WO-93/22443 A1 | 11/1993 |

(56) References Cited

FOREIGN PATENT DOCUMENTS

| | | |
|---|---|---|
| WO | WO-94/013677 A1 | 6/1994 |
| WO | WO-94/017803 A1 | 8/1994 |
| WO | WO-95/29673 A1 | 11/1995 |
| WO | WO-95/32984 A1 | 12/1995 |
| WO | WO-96/05309 A2 | 2/1996 |
| WO | WO-96/05309 A3 | 2/1996 |
| WO | WO-96/040706 A1 | 12/1996 |
| WO | WO-97/00271 A1 | 1/1997 |
| WO | WO-97/15658 A1 | 5/1997 |
| WO | WO-97/28133 A1 | 8/1997 |
| WO | WO-97/28161 A1 | 8/1997 |
| WO | WO-98/41525 A1 | 9/1998 |
| WO | WO-98/52611 A1 | 11/1998 |
| WO | WO-98/57952 A1 | 12/1998 |
| WO | WO-00/017202 A1 | 3/2000 |
| WO | WO-00/017203 A1 | 3/2000 |
| WO | WO-00/042042 A2 | 7/2000 |
| WO | WO-01/002369 A2 | 1/2001 |
| WO | WO-01/002369 A3 | 1/2001 |
| WO | WO-01/16114 A2 | 3/2001 |
| WO | WO-01/16114 A3 | 3/2001 |
| WO | WO-01/19829 A2 | 3/2001 |
| WO | WO-01/019829 A2 | 3/2001 |
| WO | WO-01/19829 A3 | 3/2001 |
| WO | WO-01/019829 A3 | 3/2001 |
| WO | WO-01/25238 A2 | 4/2001 |
| WO | WO-01/25238 A3 | 4/2001 |
| WO | WO-01/031063 A1 | 5/2001 |
| WO | WO-01/038584 A2 | 5/2001 |
| WO | WO-01/038584 A3 | 5/2001 |
| WO | WO-01/55140 A1 | 8/2001 |
| WO | WO-01/056988 A1 | 8/2001 |
| WO | WO-01/072751 A1 | 10/2001 |
| WO | WO-01/72778 A2 | 10/2001 |
| WO | WO-01/72778 A3 | 10/2001 |
| WO | WO-01/81346 A2 | 11/2001 |
| WO | WO-01/81346 A3 | 11/2001 |
| WO | WO-02/06192 A1 | 1/2002 |
| WO | WO-02/030944 A2 | 4/2002 |
| WO | WO-02/030944 A3 | 4/2002 |
| WO | WO-02/057425 A2 | 7/2002 |
| WO | WO-02/057425 A3 | 7/2002 |
| WO | WO-02/076986 A1 | 10/2002 |
| WO | WO-02/080926 A1 | 10/2002 |
| WO | WO-02/083143 A1 | 10/2002 |
| WO | WO-02/088025 A1 | 11/2002 |
| WO | WO-02/090334 A1 | 11/2002 |
| WO | WO-03/000187 A2 | 1/2003 |
| WO | WO-03/000187 A3 | 1/2003 |
| WO | WO-03/016275 A1 | 2/2003 |
| WO | WO-03/020880 A2 | 3/2003 |
| WO | WO-03/020880 A3 | 3/2003 |
| WO | WO-03/024969 A1 | 3/2003 |
| WO | WO-03/035075 A1 | 5/2003 |
| WO | WO-03/059884 A1 | 7/2003 |
| WO | WO-03/082341 A1 | 10/2003 |
| WO | WO-03/106426 A1 | 12/2003 |
| WO | WO-04/006906 A2 | 1/2004 |
| WO | WO-04/006906 A3 | 1/2004 |
| WO | WO-04/018058 A2 | 3/2004 |
| WO | WO-04/018058 A3 | 3/2004 |
| WO | WO-04/031177 A1 | 4/2004 |
| WO | WO-04/039774 A2 | 5/2004 |
| WO | WO-04/039774 A3 | 5/2004 |
| WO | WO-04/056830 A1 | 7/2004 |
| WO | WO-04/087053 A2 | 10/2004 |
| WO | WO-04/087053 A3 | 10/2004 |
| WO | WO-04/100868 A2 | 11/2004 |
| WO | WO-04/100868 A3 | 11/2004 |
| WO | WO-04/111014 A1 | 12/2004 |
| WO | WO-05/002585 A1 | 1/2005 |
| WO | WO-05/007085 A2 | 1/2005 |
| WO | WO-05/007085 A3 | 1/2005 |
| WO | WO-05/012323 A2 | 2/2005 |
| WO | WO-05/012323 A3 | 2/2005 |
| WO | WO-05/016348 A1 | 2/2005 |
| WO | WO-05/016349 A1 | 2/2005 |
| WO | WO-05/016528 A2 | 2/2005 |
| WO | WO-05/016528 A3 | 2/2005 |
| WO | WO-05/021533 A1 | 3/2005 |
| WO | WO-05/044181 A2 | 5/2005 |
| WO | WO-05/044181 A3 | 5/2005 |
| WO | WO-05/047289 A1 | 5/2005 |
| WO | WO-05/061460 A1 | 7/2005 |
| WO | WO-05/063258 A1 | 7/2005 |
| WO | WO-05/067901 A2 | 7/2005 |
| WO | WO-05/067901 A3 | 7/2005 |
| WO | WO-05/074603 A2 | 8/2005 |
| WO | WO-05/074603 A3 | 8/2005 |
| WO | WO-05/097800 A1 | 10/2005 |
| WO | WO-05/105760 A1 | 11/2005 |
| WO | WO-05/112935 A1 | 12/2005 |
| WO | WO-05/113556 A1 | 12/2005 |
| WO | WO-05/117889 A1 | 12/2005 |
| WO | WO-05/120511 A1 | 12/2005 |
| WO | WO-06/030032 A1 | 3/2006 |
| WO | WO-06/038865 A1 | 4/2006 |
| WO | WO-06/050501 A2 | 5/2006 |
| WO | WO-06/050501 A3 | 5/2006 |
| WO | WO-06/050946 A1 | 5/2006 |
| WO | WO-06/068760 A2 | 6/2006 |
| WO | WO-06/068760 A3 | 6/2006 |
| WO | WO-06/089106 A2 | 8/2006 |
| WO | WO-06/089106 A3 | 8/2006 |
| WO | WO-06/102079 A1 | 9/2006 |
| WO | WO-06/108107 A1 | 10/2006 |
| WO | WO-06/112666 A1 | 10/2006 |
| WO | WO-06/114064 A2 | 11/2006 |
| WO | WO-06/114064 A3 | 11/2006 |
| WO | WO-06/114065 A2 | 11/2006 |
| WO | WO-06/114065 A3 | 11/2006 |
| WO | WO-06/114180 A1 | 11/2006 |
| WO | WO-07/002293 A2 | 1/2007 |
| WO | WO-07/002293 A3 | 1/2007 |
| WO | WO-07/006547 A1 | 1/2007 |
| WO | WO-07/020046 A1 | 2/2007 |
| WO | WO-07/025090 A2 | 3/2007 |
| WO | WO-07/025090 A3 | 3/2007 |
| WO | WO-07/061737 A2 | 5/2007 |
| WO | WO-07/061737 A3 | 5/2007 |
| WO | WO-07/066189 A2 | 6/2007 |
| WO | WO-07/066189 A3 | 6/2007 |
| WO | WO-07/075554 A2 | 7/2007 |
| WO | WO-07/075554 A3 | 7/2007 |
| WO | WO-07/079164 A2 | 7/2007 |
| WO | WO-07/079164 A3 | 7/2007 |
| WO | WO-07/095223 A2 | 8/2007 |
| WO | WO-07/095223 A3 | 8/2007 |
| WO | WO-07/103308 A2 | 9/2007 |
| WO | WO-07/103308 A3 | 9/2007 |
| WO | WO-07/106503 A2 | 9/2007 |
| WO | WO-07/106503 A3 | 9/2007 |
| WO | WO-07/112005 A2 | 10/2007 |
| WO | WO-07/112005 A3 | 10/2007 |
| WO | WO-07/114926 A2 | 10/2007 |
| WO | WO-07/114926 A3 | 10/2007 |
| WO | WO-07/121453 A2 | 10/2007 |
| WO | WO-07/121453 A3 | 10/2007 |
| WO | WO-07/121920 A2 | 11/2007 |
| WO | WO-07/121920 A3 | 11/2007 |
| WO | WO-07/121924 A2 | 11/2007 |
| WO | WO-07/121924 A3 | 11/2007 |
| WO | WO-07/124854 A1 | 11/2007 |
| WO | WO-07/125310 A2 | 11/2007 |
| WO | WO-07/125310 A3 | 11/2007 |
| WO | WO-07/125315 A2 | 11/2007 |
| WO | WO-07/125315 A3 | 11/2007 |
| WO | WO-07/126841 A2 | 11/2007 |
| WO | WO-07/126841 A3 | 11/2007 |
| WO | WO-07/134828 A1 | 11/2007 |
| WO | WO-07/135380 A2 | 11/2007 |
| WO | WO-07/135380 A3 | 11/2007 |
| WO | WO-07/135398 A1 | 11/2007 |
| WO | WO-08/025755 A1 | 3/2008 |

(56) References Cited

FOREIGN PATENT DOCUMENTS

| WO | WO-08/037477 A1 | 4/2008 |
|---|---|---|
| WO | WO-08/047821 A1 | 4/2008 |
| WO | WO-08/063625 A2 | 5/2008 |
| WO | WO-08/063625 A3 | 5/2008 |
| WO | WO-08/064018 A1 | 5/2008 |
| WO | WO-08/079028 A1 | 7/2008 |
| WO | WO-08/082487 A2 | 7/2008 |
| WO | WO-08/082487 A3 | 7/2008 |
| WO | WO-08/094737 A2 | 8/2008 |
| WO | WO-08/094737 A3 | 8/2008 |
| WO | WO-08/112715 A2 | 9/2008 |
| WO | WO-08/112715 A3 | 9/2008 |
| WO | WO-08/118454 A2 | 10/2008 |
| WO | WO-08/118454 A3 | 10/2008 |
| WO | WO-08/118455 A1 | 10/2008 |
| WO | WO-08/118468 A1 | 10/2008 |
| WO | WO-08/125014 A1 | 10/2008 |
| WO | WO-08/125207 A1 | 10/2008 |
| WO | WO-08/127226 A2 | 10/2008 |
| WO | WO-08/127726 A3 | 10/2008 |
| WO | WO-08/136457 A1 | 11/2008 |
| WO | WO-09/000412 A1 | 12/2008 |
| WO | WO-09/004621 A1 | 1/2009 |
| WO | WO-09/010925 A2 | 1/2009 |
| WO | WO-09/010925 A3 | 1/2009 |
| WO | WO-09/023718 A2 | 2/2009 |
| WO | WO-09/023718 A3 | 2/2009 |
| WO | WO-09/044707 A1 | 4/2009 |
| WO | WO-09/050506 A2 | 4/2009 |
| WO | WO-09/050506 A3 | 4/2009 |
| WO | WO-09/064802 A2 | 5/2009 |
| WO | WO-09/064802 A3 | 5/2009 |
| WO | WO-2009/062118 A2 | 5/2009 |
| WO | WO-2009/062118 A3 | 5/2009 |
| WO | WO-09/088986 A1 | 7/2009 |
| WO | WO-09/088990 A1 | 7/2009 |
| WO | WO-09/100406 A2 | 8/2009 |
| WO | WO-09/100406 A3 | 8/2009 |
| WO | WO-09/117157 A1 | 9/2009 |
| WO | WO-10/009207 A1 | 1/2010 |
| WO | WO-10/019210 A2 | 2/2010 |
| WO | WO-10/019210 A3 | 2/2010 |
| WO | WO-10/036380 A1 | 4/2010 |
| WO | WO-10/039534 A2 | 4/2010 |
| WO | WO-10/039534 A3 | 4/2010 |
| WO | WO-2010/045542 A2 | 4/2010 |
| WO | WO-2010/045542 A3 | 4/2010 |
| WO | WO-2011/047384 A2 | 4/2011 |
| WO | WO-2011/047384 A3 | 4/2011 |
| WO | WO-2013/077921 A2 | 5/2013 |
| WO | WO-2013/077921 A3 | 5/2013 |
| WO | WO-2013/077921 A9 | 5/2013 |

OTHER PUBLICATIONS

"Report of the Expert Committee on the Diagnosis and Classification of Diabetes Mellitus", Diabetes Care (1992) 2(Suppl 1):S5-S19.

Abbott, L. et al. (Mar. 1, 2007, e-published Dec. 15, 2006). "Discovery of thienopyridines as Src-family selective Lck inhibitors," Bioorg Med Chem Lett 17(5):1167-1171.

Abdel-Mohsen, S.A., "Synthesis, reactions and antimicrobial activity of 2-amino-4-(8-quinolino1-5-y1)-1-(p-toly1)-pyrrole-3-carbonitrile", Bull. Korean Chem. Soc. 2005 26(5):719-728.

Ahmed, M. et al., *Eur J Endocrinol*, 2011, 165315-322.

Ames et al., "Heterocyclic Synthesis from o-Halogen-acids. Part II. Thienopyridinones and Thienopyranones from 3-bromothiophene-2- and 4-Bromothiophene-3-Carboxylic Acids", Journal of the Chemical Society, Perkin Transactions 1, Jan. 14:1390-1395 (1975).

Andrews, R.C., et al. "Effects of the 11p-Hydroxysteroid Dehydrogenase Inhibitor Carbenoxolone on Insulin Sensitivity in Men with Type 2 Diabetes", J. Clin. Endocrinol. Metab. (2003) 88(1):285¬291.

Apsel, B. et al., Nat Chem Biol, 2008. 4(11): p. 691-9) dual PI3K:tyrosine kinase inhibitor PP121 (Fig. 1B).

Aragon, Anthony D. et al., "Characterization of Differentiated Quiescent and Nonquiescent Cells in Yeast Stationary-Phase Cultures", Molecular Biology of the Cell 19:1271-1280, 2008 Aragon, Anthony D. et al., Microarray based analysis of temperature and oxidative stress induced messenger RNA in Schistosoma mansoni, Molecular & Biochemical Parasitology 162:134¬ 141, 2008.

Aragon, Tomas et al., "Messenger RNA targeting to endoplasmic reticulum stress signaling sites", Nature 457(7230):736-740, 2009.

Arnold, et al. "Pyrrolo[2,3-d]pyrimidines containing an extended 5-substituent as potent and selective inhibitors of Ick I", Bioorg. & Med. Chem. Lett (2000) 10:2167-70.

Banker, G.S., et al. Modern Pharmaceutics, 3ed, Marcel Dekker, New York, 1996, pp. 451-596.

Barf, T. et al. "Arylsulfonamidothiazoles as a New Class of Potential Antidiabetic Drugs. Discovery of Potent and Selective Inhibitors of the 11p-Hydroxysteroid Dehydrogenase Type 1", J. Med. Chem. (2002) 45(18):3813-3815.

Barnes, P.J., et al. "Efficacy and Safety of Inhaled Corticosteroids in Asthma", Am. Rev. Respir. Dis. (1993) 148:S1-26.

Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011, 10 pages.

Beeram, M. et al., "Akt-induced endocrine therapy resistance is reversed by inhibition of mTOR signaling", Annals of Oncology 18:1323-1328, 2007.

Bell, G., et al. "Glucokinase Mutations Insulin Secretion, and Diabetes Mellitus", Annu. Rev. Physiol., (1996) 58:171-186.

Berge, Stephen M. et al., "Pharmaceutical Salts", Journal of Pharmaceutical Sciences Berge et al., "Pharmaceutical Salts", Journal of Pharmaceutical Sciences 66(1):1-19, 1977.

Bhat, G. A., et al., "Pyrazolopyrimidine nucleosides. 12. Synthesis and biological activity of certain pyrazolo[3,4-d]pyrimidine nucleosides related to adenosine," J. Med. Chem. vol. 24, No. 10, (1981), pp. 1165-1172.

Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.

Bishop, Anthony C. et al., "Design of allele-specific inhibitors to probe protein kinase signalling", Current Biology 8:257-266, 1998.

Blethrow, Justin et al., "Design and Use of Analog-Sensitive Protein Kinases", Current Protocols in Molecular Biology 18.11.1-18.11.19, 2004.

Bohren, K.M., et al. "Expression, Crystallization and Preliminary Crystallographic Analysis of Human Carbonyl Reductase", J. Mol. Biol. (1994) 224:659-664.

Campora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.

Campora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.

Cannon, J.G., "Analog Design", Burger's Medicinal Chemistry and Drug Discovery, Fifth Edition, vol. 1: Principles and Practice, 1995, pp. 783-802.

Carlomagno, F. et al., *Cancer Res*, 2002. 62(24): p. 7284-90).

Carracedo, A. et al., *J Clin Invest*, 2008. 118(9): p. 3065-74.

Carrasco, Daniel R. et al., "The Differentiation and Stress Response Factor XBP-1 Drives Multiple Myeloma Pathogenesis", Cancer Cell 11:349-360, 2007.

Chaisuparat, et al. Dual Inhibition of PI3K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68(8):1029-1036.

(56) References Cited

OTHER PUBLICATIONS

Cox, B., et al. "Human Colorectal Cancer Cells Efficiently Conjugate the Cyclopentenone Prostaglandin, Prostaglandin J2 to Glutathione", Biochim. Biophys. Acta (2002) 1584:37-45.
Cox, Jeffery S. et al., "A Novel Mechanism for Regulating Activity of a Transcription Factor That Controls the Unfolded Protein Response", Cell 87:391-404, 1996.
Credle, Joel J. et al., "On the mechanism of sensing unfolded protein in the endoplasmic reticulum", Proceedings of the National Academy of Sciences 102(52):18773-18784, 2005.
Dar et al., "Small Molecule Recognition of c-Src via the Imatinib 1-35-Binding Conformation", Chemistry &Biology, vol. 15, 2008, 1015-1022.
Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.
Diederich, S., et al. "In the Search for Specific Inhibitors of Human 11p-Hydroxysteroid-Dehydrogenases (11(3-HSDs): Chenodeoxycholic Acid Selectively Inhibits 11p-HSD-I", Eur. J. Endocrinol. (2000) 142:200-207.
Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.
Ding, S., et al. "A Combinatorial Scaffold Approach Toward Kinase-Directed Heterocycle Libraries", J. Am. Chem. Soc. (2002) 124(8):1594-1596.
Ding, S., et al. "A Concise and Traceless Linker Strategy Toward Combinatorial Libraries of 2,6,9-Substituted Purines", J. Org. Chem. (2001) 66:8273-8276.
Ding, S., et al. "Resin-Capture and Release Strategy Toward Combinatorial Libraries of 2,6,9-Substituted Purines", J. Comb. Chem.(2002) 4:183-186.
Donati. Emerging Therapies for Neovascular Age-Related Macular Degeneration: State of the Art. Ophthalmologica. 2007;221:366-377.
Doody, Gina M. et al., "BLIMP-1 is a target of cellular stress and downstream of the unfolded protein response", European Journal of Immunology 36:1572-1582, 2006.
Durante, C. et al., *Expert Opin Investig Drugs* ,2011. 20(3): p. 407-413.
European Examination Report dated Sep. 14, 2011 for EP Application No. 07873406.8, 4 pages.
European search report and search opinion dated Oct. 26, 2011 for Application No. 9700424.6, 5 pages.
European Search Report dated Mar. 1, 2010 for EP Application No. 07873406.8, 5 pages.
European Search Report dated Feb. 4, 2011 for EP Application No. 05857011.0, 5 pages.
Examination Report for GB Application No. GB0819947.3 dated Oct. 27, 2010, 2 pages.
Extended European Search Report from corresponding European Application No. 09700784.3 dated Oct. 28, 2011, 6 pages.
Extended European Search Report from corresponding European Application No. 12175020.2 dated Jan. 1, 2013, 7 pages.
Extended European Search Report from corresponding European Application No. 12175019.4 dated Apr. 4, 2013, 12 pages.
Fajans, S., et al."Maturity Onset Diabetes of the Young (MODY)", Diabet. Med. (1996) 13:S90-S95.
Feinstein, M.B., et al. "Regulation of the Action of Hydrocotisone in Airway Epithelial Cells by 116-Hydroxysteroid Dehydrogenase", Am. J. Respir. Cell. Mol. Biol. (1999) 21:403-408.
Feldman, M.E. et al. , "Active site inhibitors of mTOR target rapamycin-resistant outputs of mTORC1 and mTORC2", PLOS Biology 7(2):371-383, Feb. 2009.
Fingl, E., et al. "General Principles", The Pharmacological Basis of Therapeutics, Fifth Edition (1975), Ch. 1, 1-46.
Forrest, G.L., et al. "Carbonyl Reductase", Chem. Biol. Interact. (2000) 129:21-40.

Forrest, G.L., et al. "Induction of a Human Carbonyl Reductase Gene Located on Chromosome 21", Biochim. Biophys. Acta. (1990) 1048:149-155.
Franzen, R. "The Suzuki, the Heck, and the Stille reaction—three versative methods for the introduction of new C—C bonds on solid support", Can J. Chem. (2000) 78:957-962.
Funder, J.W., et al. "Mineralocorticoid Action: Target Tissue Specificity Is Enzyme, Not Receptor, Mediated", Science (1998) 242:583-585.
Garber, M.E., et al. "Diversity of Gene Expression in Adenocarcinoma of the Lung", Proc. Nat. Acad. Sci. USA (2001) 98(24):13784-13789.
Gedaly, R. et al., *Anticancer Res.* 30(12): p. 4951-8, 2010.
Gonzalez, B., et al. "Protection against Daunorubicin Cytotoxicity by Expression of a Cloned Human Carbonyl Reductase cDNA in K562 Leukemia Cells", Cancer Res. (1995) 55:4646-4650.
Gonzalez, Tania N. et al., "Ire1p: A Kinase and Site-Specific Endoribonuclease", Methods in Molecular Biology 160:25-36, 2001.
Graupera, et al. Angiogenesis selectively requires the p110 isoform of PI3K to control endothelial cell migration. Nature. 2008;453:662-666.
Haase, A.,et al. "Detection of Viral Nucleic Acids by in Situ Hybridization", Methods in Virology (1984) VII:189-226.
Hanefeld, U., et al. "One-pot Synthesis of Tetrasubstituted Pyrazoles Proof of Regiochemistry", J. Chem. Soc. Perkin Trans. (1996) 1:1545-1552.
Hellwinkel, et al. Heterocyclensynthesen mit MF/A1203-Basensystemen: 2-Arylbenzofurane and 2,3-Diarylisochinolin-1(2H)-one. Synthesis. 1995;1995(9):1135-41.
International Preliminary Report on Patentability and Written Opinion dated Jan. 1, 2011 for International Application No. PCT/US2009/049969, 7 pages.
International Preliminary Report on Patentability and Written Opinion dated May 22, 2007 for International Application No. PCT/US2005/042524, 12 pages.
International Preliminary Report on Patentability and Written Opinion dated Nov. 4, 2008 for International Application No. PCT/US2007/008355, 7 pages.
International Preliminary Report on Patentability and Written Opinion dated Oct. 8, 2008 for International Application No. PCT/US2007/008395, 6 pages.
International Preliminary Report on Patentability from International Application No. PCT/US2009/000042 dated Jul. 6, 2010, 9 pages.
International Preliminary Report on Patentability and Written Opinion dated Apr. 19, 2011 for International Application No. PCT/US2009/060985, 6 pages.
International Preliminary Report on Patentability and Written Opinion dated Apr. 17, 2012 for International Application No. PCT/US2010/053072, 5 pages.
International Search Report dated Jun. 28, 2010 for International Application No. PCT/US2009/060985, 5 pages.
International Search report dated Jul. 4, 2011 for International Application No. PCT/US2010/053072, 5 pages.
International Search Report in the PCT/US2012/053542 application, dated Jun. 28, 2013.
International search report and written opinion dated Aug. 22, 2011 for PCT/US2011/037412, 2 pages.
International search report and written opinion dated Nov. 20, 2009 for PCT/US2009/005380, 9 pages.
International search report dated Nov. 2, 2010 for PCT Application No. PCT/US10/02020, 8 pages.
International search report dated Mar. 11, 2009 for PCT Application No. PCT/US2009/00038, 1 page.
International search report dated Mar. 23, 2009 for PCT Application No. PCT/US2009/00042, 2 pages.
International Search Report dated Apr. 5, 2006 for international Application No. PCT/FR2005/051073, 3 pages.
International Search Report dated Aug. 27, 2008 for International Application No. PCT/US07/08395, 4 pages.
International Search Report dated Mar. 15, 2010 for International Application No. PCT/US2009/049969, 4 pages.

(56) References Cited

OTHER PUBLICATIONS

International Search Report dated Oct. 2, 2006 for International Application No. PCT/US05/042524, 7 pages.
International Search Report dated Sep. 25, 2008 for International Application No. PCT/US07/08355, 1 page.
Ishiyama, T., et al. "A Stoichiometric Aromatic C—H Borylation Catalyzed by Iridium(I)/2,2'-Bipyridine Complexes at Room Temperature", Angew. Chem. Int. Ed. (2002) 41(16):3056-3058.
Ishiyama, T., et al. "Mild Iridium-Catalyzed Borylation of Arenes. High Turnover Numbers, Room Temperature Reactions, and Isolation of a Potential Intermediate", J. Am. Chem. Soc. (2002) 124(3):390-391.
Kajita, et al. Nickel-catalyzed decarbonylative addition of phthalimides to alkynes. J Am Chem Soc. May 14, 2008;130(19):6058-9.
Kallberg, Y., et al. "Short-Chain Dehydrogenase/Reductase (SDR) Relationships: a Large Family with Eight Clusters Common to Human, Animal, and Plant Genomes", Protein Sci. (2002) 11:636-641.
Kallberg, Y., et al. "Short-Chain Dehydrogenases/Reductases (SDRs)", Eur. J. Biochem. (2002) 269:4409-4417.
Kim, M. et al. , "Activation and function of the mTORC1 pathway in mast cells", The Journal of Immunology 180:4586-4595, Apr. 2008.
Kimata, Yukio et al., "Two regulatory steps of ER-stress sensor Ire 1 involving its cluster formation and interaction with unfolded proteins", The Journal of Cell Biology 179(1):75-86, 2007.
Knight, et al. "A Pharmacological Map of the P13-K Family Defines a Role for p110a in Insulin Signaling", Cell (2006) 125:733-747.
Knight, Z.A. et al., Nat. Rev. Cancer, 10(2): p. 130-7, 2010.
Koong, Albert C. et al., "Targeting XBP-1 as a Novel Anti-Cancer Strategy", Cancer Biology & Therapy 5(7):756-759, 2006.
Kost et al., "Recyclization of 3-Alkyl- and 1,3-Dialkylisoquinolinium Salts to Naphthylamines", Chemistry of Heterocyclic Compounds, Jan., 16(9):965-970 (1981).
Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.
Kreutzberger, A. et al. , "5-substituierte 4-aminopyrimidine durch aminomethinylierung von acetonitrilen", Justus Liebigs Annalen der Chemie 4:537-544, 1977.
Kudo, Takashi et al., "The Unfolded Protein Response Is Involved in the Pathology of Alzheimer's Disease", New York Academy of Sciences 977:349-355, 2002.
Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan. 8:857-862 (1978).
Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.
Kwok, B.H., et al. "The Anti-Inflammatory Natural Product Parthenolide from the Medicinal Herb Feverfew Directly Binds to and Inhibits IkB Kinase", Chem. Biol. (2001) 8:759-766.
Lee, et al. All roads lead to mTOR: integrating inflammation and tumor angiogenesis.. Cell Cycle. 2007;6(24):3011-3014.
Lee, Kenneth P.K. et al., "Structure of the Dual Enzyme Ire1 Reveals the Basis for the Catalysis and Regulation in Nonconventional RNA Splicing", Cell 132:89-100, 2008.
Lin, Jonathan H. et al., "IRE1 Signaling Affects Cell Fate During the Unfolded Protein Response", Science 318:944 (2007).
Liu, Y. and N. S. Gray, Nat Chem Biol, 2006. 2(7): p. 358-64.
Majumder, et al. mTOR inhibition reverses Akt-dependent prostate intraepithelial neoplasia through regulation of apoptotic and HIF-1-dependent pathways. Nature Medicine. 2004;10:594-601.
May, Yanjun et al., "The role of the unfolded protein response in tumour development: friend or foe?", Nature Reviews Cancer 4:966-977, 2004.
Mayer, T.U., et al. "Small Molecule Inhibitor of Mitotic Spindle Bipolarity Identified in a Pheontype-Based Screen", Science (1999) 286:971-974.
Mellinghoff, et al. TORward AKTually useful mouse models. Nature Medicine. 2004;10:579-580.
Miyaura, N., et al., "Palladium-Catalyzed Cross-Coupling Reactions of Organoboron Compounds," Chem. Rev. (1995) 95(7):2457-2483.
Modi, et at. Isoquinolones: Part IV—Synthesis of 3-Methyl, 3-Formyl & Other 3-Substituted N-Arylisoquinolones, Indian J. Chem. 1979; 18B:304-306.
Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.
Naidoo, Nirinjini et al., "Sleep deprivation induces the unfolded protein response in mouse cerebral cortex", Journal of Neurochemistry 92:1150-1157, 2005.
Nakanishi, M., et al. "Cloning and Sequence Analysis of a cDNA Encoding Tetrameric Carbonyl Reductase of Pig Lung", Biochem. Biophys. Acta (1993) 194(3):1311-1316.
Nemazanyi, et al. 3-Amino-4-aryl-1(2H)-isoquinolones. Chemistry of Heterocyclic Compounds. Mar. 1991;27(3):307-8.
Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.
Nobel, C.S.I., et al. "Purification of Full-Length Recombinant Human and Rat Type 1 11β-hydroxysteroid Dehydrogenases with Retained Oxidoreductase Activities", Protein Expr. Purif. (2002) 26:349-356.
Oda, et al. PIK3CA Cooperates with Other Phosphatidylinositol 3'-Kinase Pathway Mutations to Effect Oncogenic Transformation. Cancer Research. 2008;68:8127.
Oppermann, U.C., et al. "Forms and Functions of Human SDR Enzymes", Chem. Biol. Interact. (2001) 130-132(1-3):699-705.
Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Papa, Feroz R. et al., "Bypassing a Kinase Activity with an ATP-Competitive Drug", Science 302:1533-1537, 2003.
Patel, et al. Immunopathological aspects of age-related macular degeneration. Seminars in Immunopathology. 2008;30(2):97-110.
Persson, C.G. "Glucocorticoids for Asthma—Early Contributions", Pulm. Pharmacol. (1989) 2:163-166.
Petrie et al., "A novel biotinylated adenylate analogue derived from pyrazolo[3,4-d]pyrimidine for labeling DNA probes," Bioconj. Chem. vol. 2, No. 6, (1991), pp. 441-446.
Pudlo, J.S., et al. "Synthesis, Antiproliferative, and Antiviral Activity of Certain 4-Substituted and 4,5 Disubstituted 7[1,3-Dihydroxy-2-propoxy)methyl]pyrrolo[2,3-d]pyrimidines", J. Med. Chem. (1990) 33:1984-1992.
Read D. et al., Genetics, 2005. 171(3): p. 1057-81.
Read D., E.A. Bach, and R.L. Cagan, Mol Cell Biol, 2004. 24(15): p. 6676-89.
Robertson, R.P. "Eicosandoids and Human Disease", Harrison's Principles of Internal Medicine, Isselbacher K.J., et al. (eds.), McGraw-Hill, New York City (1994) 1:431-435.
Romero, D.G., et al. "Cloning and Expression of the Bovine 11β-hydroxysteroid Dehydrogenase Type-2", J. Steroid Biochm. Mol. Biol. (2000) 72:231-237.
Shamu, Caroline E. et al., "Oligomerization and phosphorylation of the Ire1p kinase during intracellular signaling from the endoplasmic reticulum to the nucleus", The EMBO Journal 15(12):3028-3039, 1996.

(56) References Cited

OTHER PUBLICATIONS

Sheridan, R.P., "The Most Common Chemical Replacements in Drug-Like Compounds". J. Chem. Inf. Comput. Sci. 2002, 42:103-108.
Singer, R.H., et al. "Optimization of in situ Hybridization Using Isotopic and Non-Isotopic Detection Methods", Biotechniques (1986) 4(3):230-250.
Soldan, M., et al. "Induction of Daunorubicin Carbonyl Reducing Enzymes by Daunorubicin in Sensitive and Resistant Pancreas Carcinoma Cells", Biochem. PharmacoL (1996) 51:117-123.
S.M. Wilhelm et al., Cancer Res, 2004. 64(19): p. 7099-109.
Stanoeva et al. Homophthalic anhydrides and their application to the synthesis of heterocyclic compounds (review). Chemistry of Heterocyclic Compounds. Dec. 1984;20(12);1305-15.
Sun, L. et al., J Med Chem, 2003. 46(7): p. 1116-9.
Supplementary European Examination Report dated Sep. 20, 2011 for EP Application No. 07754845.1, 4 pages.
Supplementary European Search Report dated Feb. 24, 2010 for EP Application No. 07754845, 4 pages.
Supplementary European Search Report dated Feb. 16, 2010 for EP Application No. 07754845.1, 4 pages.
Takeuchi, H. et al., "Synergistic augmentation of reapamycin-induced autophagy in malignant glioma cells by phosphatidylinositol 3-kinase/protein kinase B inhibitors", Cancer Research 65(8):3336-3346, Apr. 15, 2005.
Tanaka, M., et al. "An Unbiased Cell Morphology-Based Screen for New, Biologically Active Small Molecules", PLoS Biology (2005) 3(5):0764-0776.
Tseng, Ping-Hui et al., "Synergistic interactions between imatinib mesylate and the novel phosphoinositide-dependent kinase-1 inhibitor OSU-03012 in overcoming imatinib mesylate resistance", Blood 105:4021-4027, 2005.
Ugarkar, B.G., et al. "Adenosine Kinase Inhibitors. 2. Synthesis, Enzyme Inhibition, and Antiseizure Activity of Diaryltubercidin Analogues", J. Med. Chem. (2000) 43:2894-2905.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole-4-carboxylic acid hydrazides under the influence of CuCl: formatin of a diazepinone and dehydrodimerization into the corresponding bis(pyrazolo [4,3-d] [1,2] diazepinone)", Tetrahedron Letters, Jan., 46(26): 4457-4459 (2005).

Verbeek, N.H. et al., J Clin Endocrinol Metab, 2011. 96(6): p. E991-5.
Vidal, M. et al., Cancer Res, 2005. 65(9): p. 3538-41.
Vidal, M., D.E. Larson, and R.L. Cagan, Dev Cell, 2006. 10(1): p. 33-44.
Vidal, M. et al., Cancer Res, 2007. 67(21): p. 10278-85).
Walker et al., "Structural Determinants of Phosphoinositide 3-Kinase Inhibition by Wortmannin, LY294002, Quercetin, Myricetin, and Staurosporine", Molecular Cell 2000, 6(4):909-919.
Wells, S.A., Jr. et al., J Clin Oncol, 2010. 28(5): p. 767-72.
Wells SA, R.B., Gagel RF et al., JClin Oncol (Meeting Abstracts), 2010. 28(Suppl): p. 5503.
White, P.C., et al. "11p—Hydroxysteroid Dehydrogenase and the Syndrome of Apparent Mineralocorticoid Excess", Endocr. Rev. (1997) 18(1):135-156.
Widler, L., et al. "7-Alkyl- and 7-Cycloalkyl-5-aryl-pyrrolo[2,3-d]pyrimidines—Potent Inhibitors of the Tyrosine Kinase c-Src," Bioorganic & Medicinal Chemistry Letters (2001) 11(6):849-852.
Wolff, M. E. Burger's Medicinal Chemistry, 5ed, Part 1, John Wiley & Sons, 1995, pp. 975-977.
Wymann, et al., "Wortmannin Inactivates Phosphoinositide 3-Kinase by Covalent Modification of Lys-802, a Residue Involved in the Phosphate Transfer Reaction", Molecular and Cellular Biology 1996, 16(4):1722-1733.
Yaguchi, et al., "A novel phosphatidylinositol 3-kinase inhibitor, ZSTK474 exterted antitumor activity against human tumor xenografts by oral administration", Proc. Amer. Assoc. Cancer Res. 2005, 46:1691 (Abstract).
Yaguchi, et al. Antitumor activity of ZSTK474, a new phosphatidylinositol 3-kinase inhibitor. J. Natl. Cancer. Inst. 2006; 98(8): 545-556. Abstract only.
Yoshida, Hiderou et al., "XBP1 mRNA Is Induced by ATF6 and Spliced by IRE1 in Response to ER Stress to Produce a Highly Active Transcription Factor", Cell 107:881-891, 2001.
Zhang, Xuewu et al., "An Allosteric Mechanism for Activation of the Kinase Domain of Epidermal Growth Factor Receptor", Cell 125:1137-1149, 2006.
Zheng, Yi et al., "Hepatitis C Virus Non-structural Protein NS4B Can Modulate an Unfolded Protein Response", The Journal of Microbiology 43(6):529-536, 2005.
Korean Intellectual Property Office, PCT/US2009/060985 International Search Report and Written Opinion, dated Jun. 28, 2010, 14 pages.

\* cited by examiner

Experiment A
- 5x10⁶ TT cells, without matrigel, implanted per mouse to seed tumors
- tumors grown for 28 days prior to commencing dosing
- drugs administered by oral gavage once daily (5 days ON, 2 days OFF)

| | Day 0 | | | Day 38 | | | Tumor Growth (day38 / day0) | % Tumor Growth Inhibition = 100 − [100* (drug/vehicle)] |
|---|---|---|---|---|---|---|---|---|
| | Mean (mm³) | SEM | N | Mean (mm³) | SEM | N | | |
| vehicle | 67.7 | 26.1 | 6 | 388.9 | 207.4 | 6.0 | 5.7 | |
| 20 mg/kg AD57 | 63.7 | 20.9 | 10 | 170.5 | 44.8 | 10.0 | 2.7 | 53.5 |

Experiment B
- 5x10⁶ TT cells, with matrigel, implanted per mouse to seed tumors
- tumors grown for 11 days prior to commencing dosing
- drugs administered by oral gavage once daily (5 days ON, 2 days OFF)

| | Day 0 | | | Day 29 | | | Tumor Growth (day29 / day0) | % Tumor Growth Inhibition = 100 − [100* (drug/vehicle)] |
|---|---|---|---|---|---|---|---|---|
| | Mean (mm³) | SEM | N | Mean (mm³) | SEM | N | | |
| vehicle | 108.4 | 7.0 | 20 | 790.8 | 124.9 | 20.0 | 7.3 | |
| 30 mg/kg AD80 | 113.9 | 10.3 | 10 | 352.6 | 69.8 | 10.0 | 3.1 | 57.6 |
| 50 mg/kg VD | 121.7 | 5.7 | 10 | 604.5 | 75.1 | 10.0 | 5.0 | 31.9 |

Figure 11

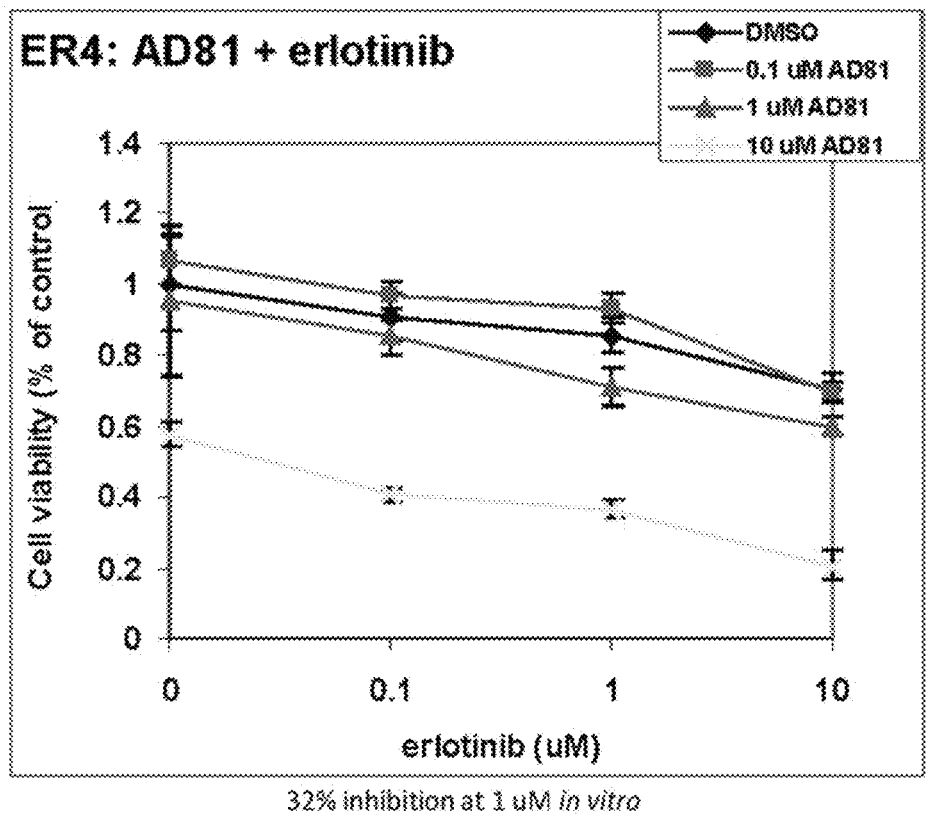
32% inhibition at 1 uM *in vitro*
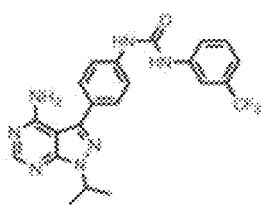
AD57
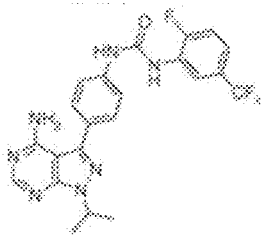
AD80
Figure 21 continued

SUBSTITUTED PYRAZOLO[3,4-D]PYRIMIDINES AND USES THEREOF

CROSS-REFERENCES TO RELATED APPLICATIONS

This application is a continuation of U.S. patent application Ser. No. 14/189,742, filed Feb. 25, 2014, which is a continuation of PCT Application No. PCT/US2012/053542, filed Aug. 31, 2012, which claims the benefit of U.S. Provisional Patent Applications No. 61/530,847, filed Sep. 2, 2011, and 61/606,296, filed Mar. 2, 2012, which are all incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. R01 EB001987, R01 CA084309 and R01 CA109730 awarded by the National Institutes of Health, and grant no. W81XWH-06-1-0727 awarded by the U.S. Army Medical Research and Materiel Command. The Government has certain rights in the invention.

BACKGROUND OF THE INVENTION

Protein kinases play important regulatory roles in numerous biological pathways controlling for example the cell cycle, cell division, metabolism, transcription and protein biosynthesis. The wide spread involvement of protein kinases in biology is underscored by links between dysregulated kinases and disease. A wide range of protein kinases have been identified as the critical drivers of various pathologies including cancer, diabetes, and inflammation. The cellular kinase signaling network is a major regulator of cancer progression: kinase signaling pathways are often co-opted for pathogenesis, and mutations in a large number of kinases have been identified as potent drivers of oncogenesis (Ding, L. et al., Nature, 2008. 455(7216): p. 1069-75; Greenman, C. et al., Nature, 2007. 446(7132): p. 153-8; Wood, L. D. et al., Science, 2007. 318(5853): p. 1108-13; Network, C.G.A.R., Nature, 2008. 455(7216): p. 1061-8). The paradigm for development of kinase inhibitor therapeutics in cancer has emerged from the success of Imatinib, which targets the single oncogenic kinase Bcr-Abl that directs Chronic Myelogenous Leukemia (CML) (Druker, B. J., Blood, 2008. 112(13): p. 4808-17). More generally, the architecture of kinase signaling networks provide multiple candidate targets for treatment of most cancer types (Knight, Z. A., H. Lin, and K. M. Shokat, Nat Rev Cancer, 10(2): p. 130-7; Manning, G. et al., Science, 2002. 298(5600): p. 1912-34). However, inhibition of specific kinases often provides only limited therapeutic efficacy. Although widely predicted to be successful, highly selective inhibitors of growth factor pathway-related kinases such as MEK1 or mitotic regulators such as Aurora B have been disappointing (Haura, E. B. et al., Clin Cancer Res., 16(8): p. 2450-7; Lorusso, P. M. et al., J Clin Oncol, 2005. 23(23): p. 5281-93; Pratilas, C. A. and D. B. Solit, Clin Cancer Res., 16(13): p. 3329-34; Rinehart, J. et al., J Clin Oncol, 2004. 22(22): p. 4456-62; Boss, D. S., J. H. Beijnen, and J. H. Schellens, Oncologist, 2009. 14(8): p. 780-93; Boss, D. S. et al., Ann Oncol., 22(2): p. 431-7). Sources of failure include rapidly emerging resistance as well as significant toxicity, which can limit dosing to levels insufficient to block tumor growth. The complexity of signaling networks and the challenge of attacking a tumor in the midst of multiple healthy organ systems that share many of the same pathway components has severely hampered the development of useful single target kinase inhibitors. By contrast most drugs approved for clinical use have multiple targets (Karaman, M. W. et al., Nat Biotechnol, 2008. 26(1): p. 127-32; Mestres, J. et al., Mol Biosyst, 2009. 5(9): p. 1051-7). For many or perhaps most, 'off-target' activities likely contribute to the drug's overall efficacy, although the mechanistic basis for this efficacy is known in only a small number of cases.

Phenotype-based drug discovery has historically been highly successful, but it has been largely supplanted by target-based discovery. Sorafenib provides a recent example of this mode of drug discovery (Lyons, J. F. et al., Endocr Relat Cancer, 2001. 8(3): p. 219-25). Sorafenib was initially developed as an inhibitor of Raf kinase, yet it showed little efficacy in mutant Ras- or Raf-driven tumors. The efficacy of Sorafenib in renal and hepatocellular cancer was later attributed to inhibition of the kinase VEGFR2 in endothelial cells and, potentially, PDGFR in pericytes; other targets may also play a role (Ahmad, T. and T. Eisen, Clin Cancer Res, 2004. 10(18 Pt 2): p. 6388S-92S; Liu, L. et al., Cancer Res, 2006. 66(24): p. 11851-8; Ostman, A. and C. H. Heldin, Adv Cancer Res, 2007. 97: p. 247-74).

Most MEN2 patients have an autosomal dominant activating mutation in the Ret (rearranged during transfection) receptor tyrosine kinase that is necessary and likely sufficient to direct a series of transformation events including medullary thyroid carcinoma (MTC), parathyroid adenoma, and pheochromocytoma (Lairmore, T. C. et al., Proc Natl Acad Sci USA, 1993. 90(2): p. 492-6; Almeida, M. Q. and C. A. Stratakis, Cancer Genet Cytogenet, 2010. 203(1): p. 30-6). The present invention provides solutions to these and other problems in the art.

BRIEF SUMMARY OF THE INVENTION

In a first aspect is provided a compound having the formula:

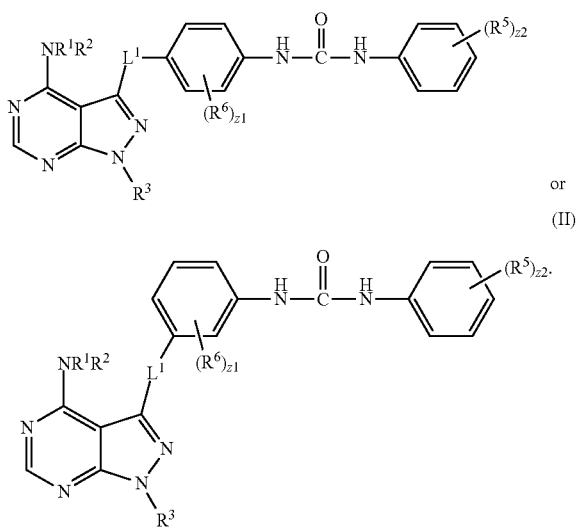

$R^1$ and $R^2$ are independently hydrogen or substituted or unsubstituted alkyl. $R^3$ is independently substituted or unsubstituted alkyl. $R^5$ is independently halogen, —CN, —$CX^a_3$, —$S(O)_2H$, —NO, —$NO_2$, —C(O)H, —C(O)$NH_2$, —$S(O)_2NH_2$, —OH, —SH, —$SO_2Cl$, —$SO_3H$, —$SO_4H$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$CO_2H$, or substituted or unsubstituted ($C_1$-$C_6$) alkyl. $R^6$ is independently halogen, —CN, —$CX^b_3$, —$S(O)_2H$, —NO, —$NO_2$, —C(O)H, —C(O)$NH_2$, —$S(O)_2NH_2$, —OH, —SH, —$SO_2Cl$, —$SO_3H$, —$SO_4H$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, or —$CO_2H$. $L^1$ is independently a bond or substituted or unsubstituted alkylene. The symbol z1 is independently an integer from 0 to 4. The symbol z2 is independently an integer from 0 to 5. The symbols $X^a$ and $X^b$ are independently —F, —Cl, —Br, or —I.

In a second aspect is provided a pharmaceutical composition including a pharmaceutically acceptable excipient and a compound as described herein (e.g. formula (I) to (XVIII), including embodiments thereof).

In a third aspect is provided a method of treating cancer in a subject in need thereof, the method including administering to the subject an effective amount of a compound as described herein (e.g. formula (I) to (XVIII), including embodiments thereof).

In a fourth aspect is provided a method of reducing the activity of RET kinase, Raf kinase, Src kinase, and S6K kinase, the method including contacting a RET kinase, a Raf kinase, a Src kinase, and a S6K kinase with an effective amount of a compound as described herein (e.g. formula (I) to (XVIII), including embodiments thereof).

In a fifth aspect is provided a method of reducing the activity of AXL kinase, the method including contacting an AXL kinase with an effective amount of a compound as described herein (e.g. formula (I) to (XVIII), including embodiments thereof).

A. Suppression of $Ret^{MEN2B}$-induced developmental block and whole animal toxicity were scored based on number of embryos (n) that survived as pupae (x) and adults (y). Drugs were mixed into food and fed to flies starting at larval stages.

B. Percent viability of control or drug treated flies determined for pupae (x/n) and adults (y/n). AD57 emerged as the best single-agent hit from the screen.

C. ptc>$dRet^{MEN2B}$ adults exhibited notum defects including excessive bristles (asterisks) and scutellum defects (brackets); controls (+DMSO) died as unenclosed adults. AD57 strongly suppressed while Sorafenib (SF) weakly suppressed these defects, yielding fully enclosed adults.

D. Structure-activity relationships suggest that Ret inhibition alone is insufficient to rescue MEN2B flies. Half maximal inhibitory concentrations (IC50) were determined against a purified form of the Ret kinase domain.

E. The AD series of compounds displayed broad-spectrum kinase inhibition profiles. Clinical (*) and known kinase inhibitors are shown for comparison.

Figure 2:
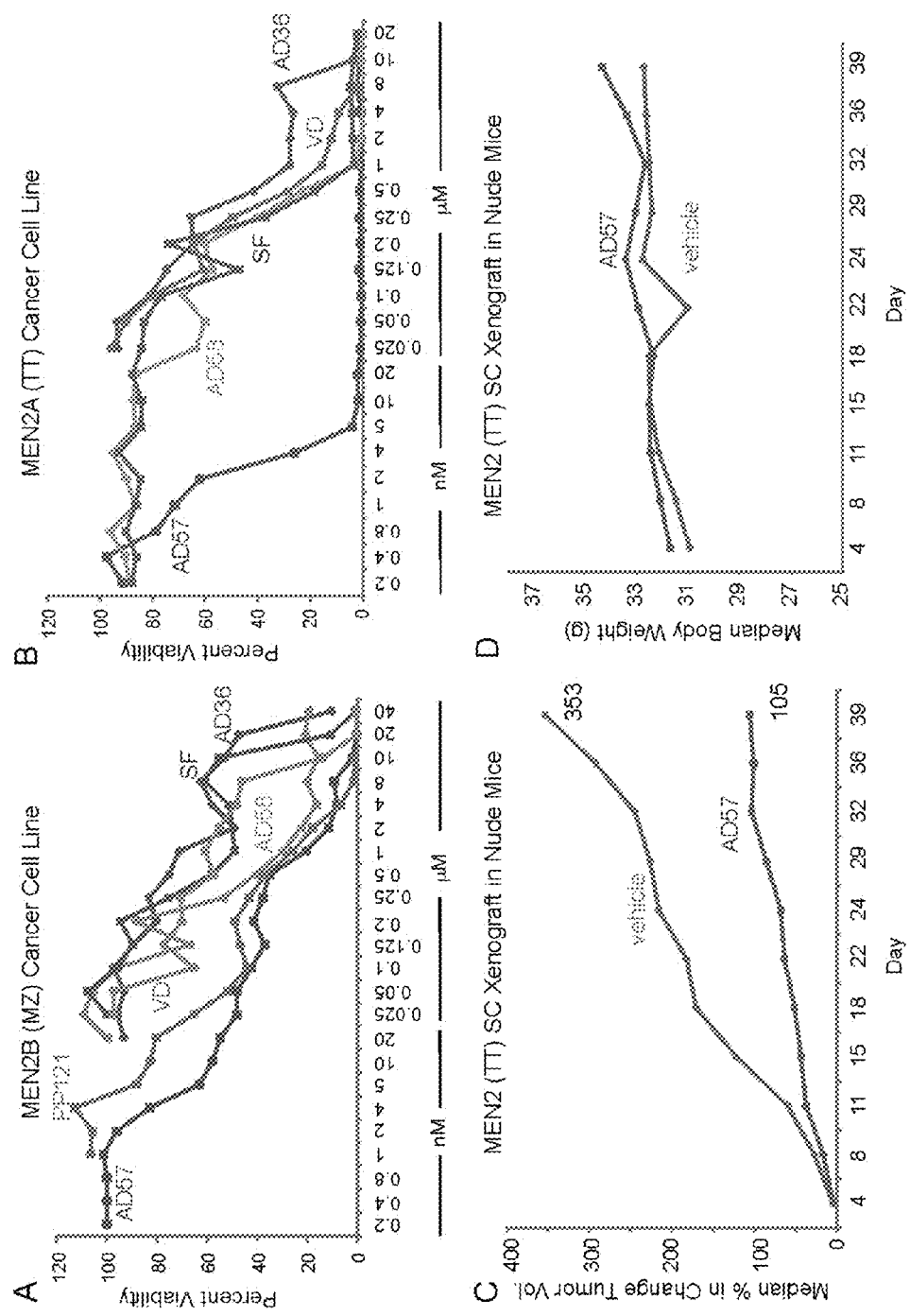

FIG. 2: AD57 rescues MEN2B phenotypes.

A. Among several kinase inhibitors, AD57 showed the most potent inhibition of viability of an MZ-CRC-1 (MEN2B) cancer cell line (SF=Sorafenib, VD=Vandetanib).

B. AD57 also showed the most potent inhibition of TT (MEN2) cell line viability.

C. AD57 reduced tumor progression nearly 3-fold compared to vehicle treated nude mice transplanted with TT cells. Values shown are the median of 10 animals.

D. Body weight measurements of AD57 and vehicle treated nude mice transplanted with TT cells. Values shown are the median of 10 animals.

Figure 3:
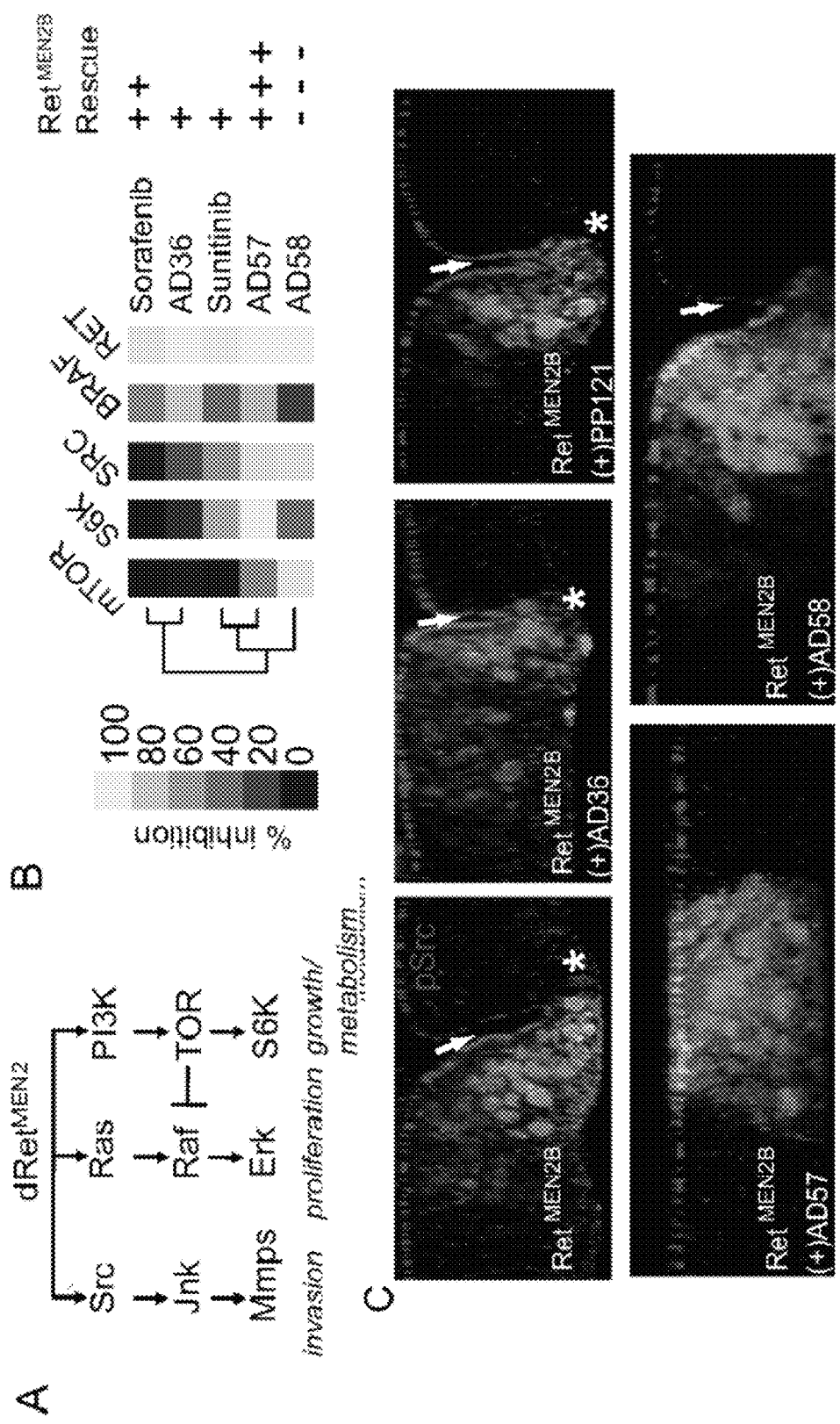
Figure 3:
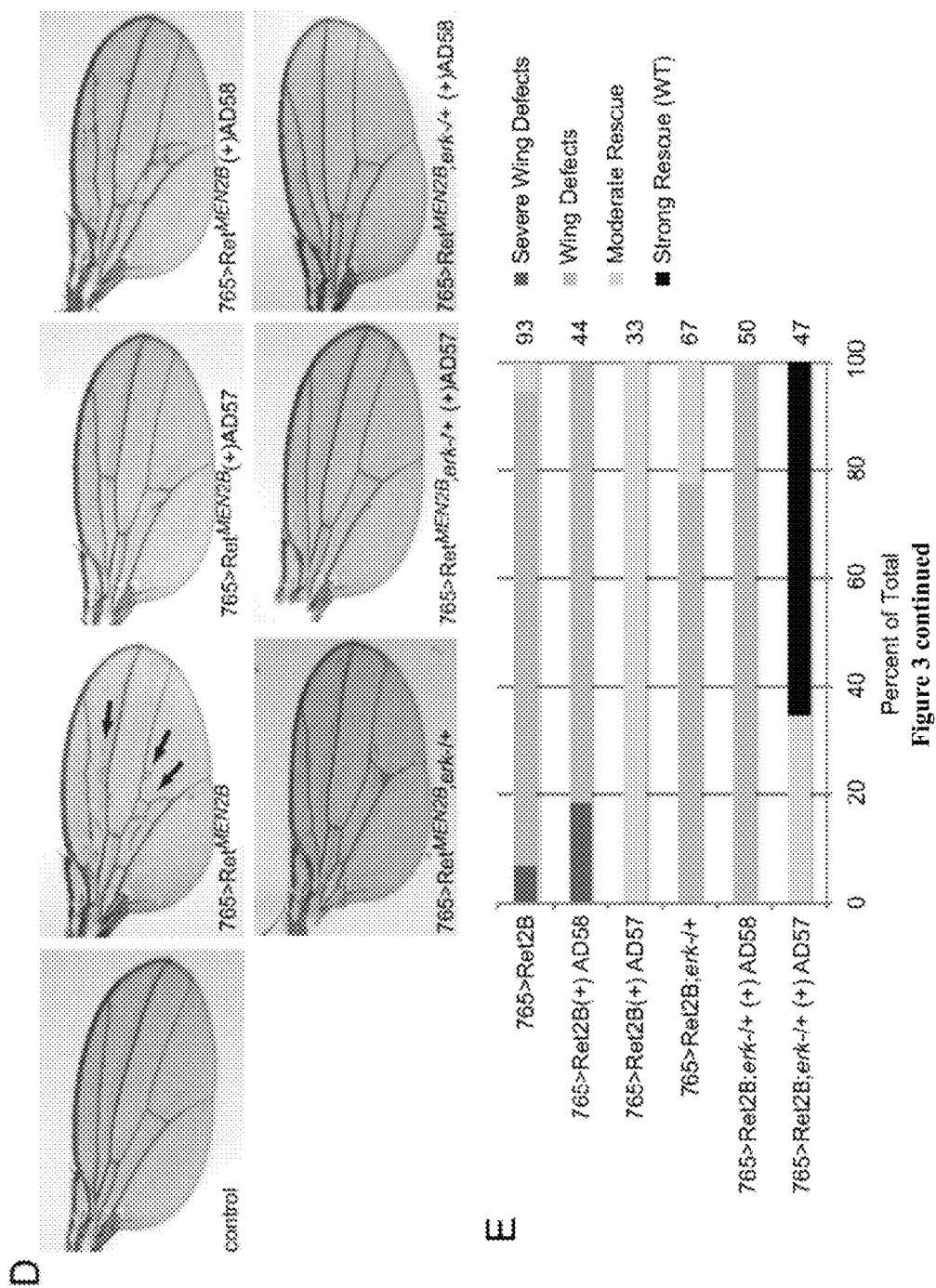

FIG. 3: Multi-pathway inhibition by AD57 mitigates dRet-driven phenotypes in the fly.

A. Partial list of signaling pathways activated by oncogenic $Ret^{MEN2B}$.

B. Percent in vitro kinase inhibition profiles (left) and levels of *Drosophila* rescue (right) are show for several inhibitors. Only AD57 significantly inhibits all three pathways. Tree indicates similarity of compounds based on hierarchical clustering of percent kinase inhibition.

C. ptc>$dRet^{MEN2B}$ wing cells (GFP+) dived basally (arrows) and invaded into adjacent wild type tissue; phospho-Src (gray spots near top edge matching gray of pSrc label) emerged at the basal invading front (asterisks). These phenotypes were strongly suppressed by AD57 but not by AD36, PP121, or AD58.

D. Broad $Ret^{MEN2B}$ expression led to ectopic wing veins (arrows), reflective of hyperactive Ras pathway signaling. The wing defects were suppressed by AD57 and enhanced by AD58. Removal of one functional copy of erk/rolled (erk−/+) enhanced rescue by AD57 and AD58.

E. Quantification of the data shown in panel C. Note that the vein phenotype was enhanced by AD58 and suppressed by AD57; reducing erk suppressed both. The number of wings analyzed under each treatment is indicated to the right of the graph.

Figure 4:
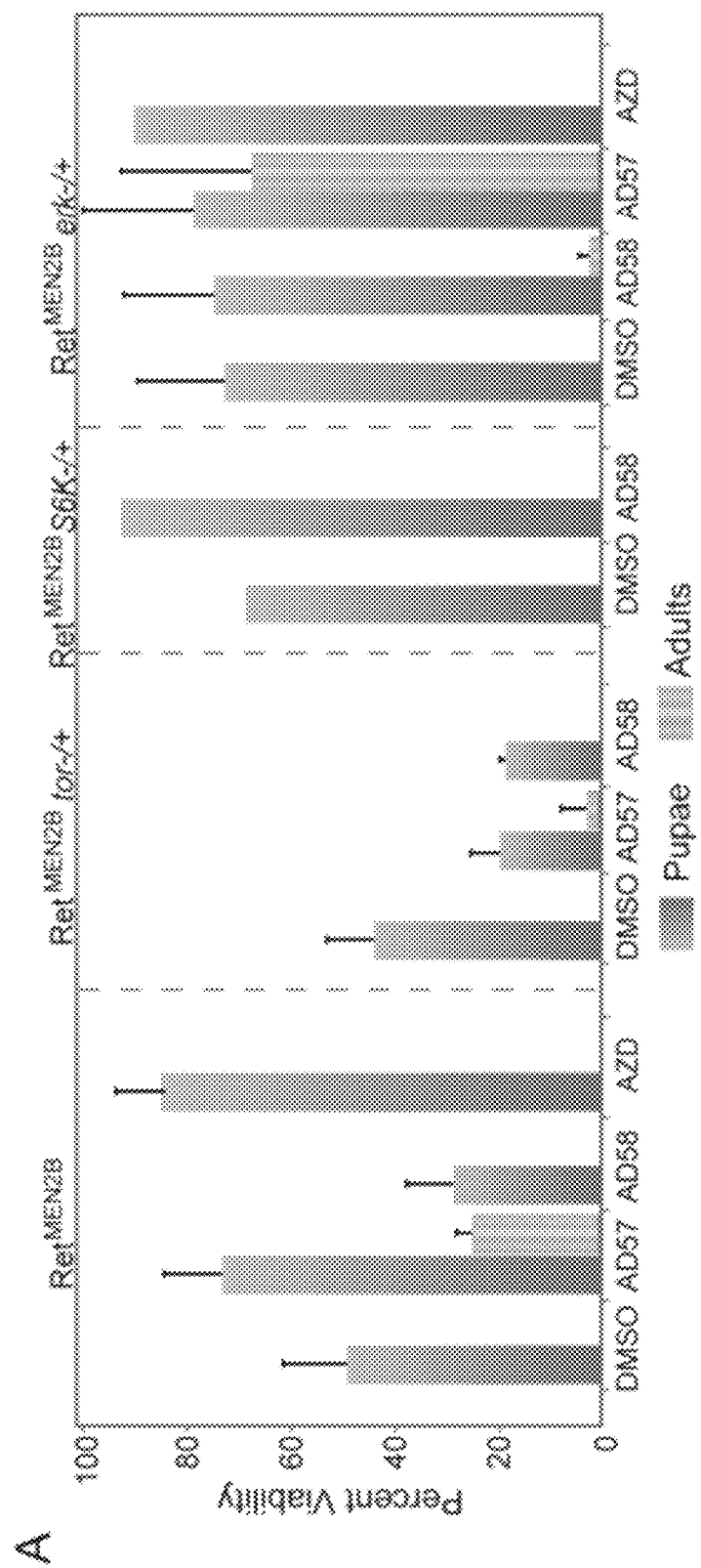
Figure 4:
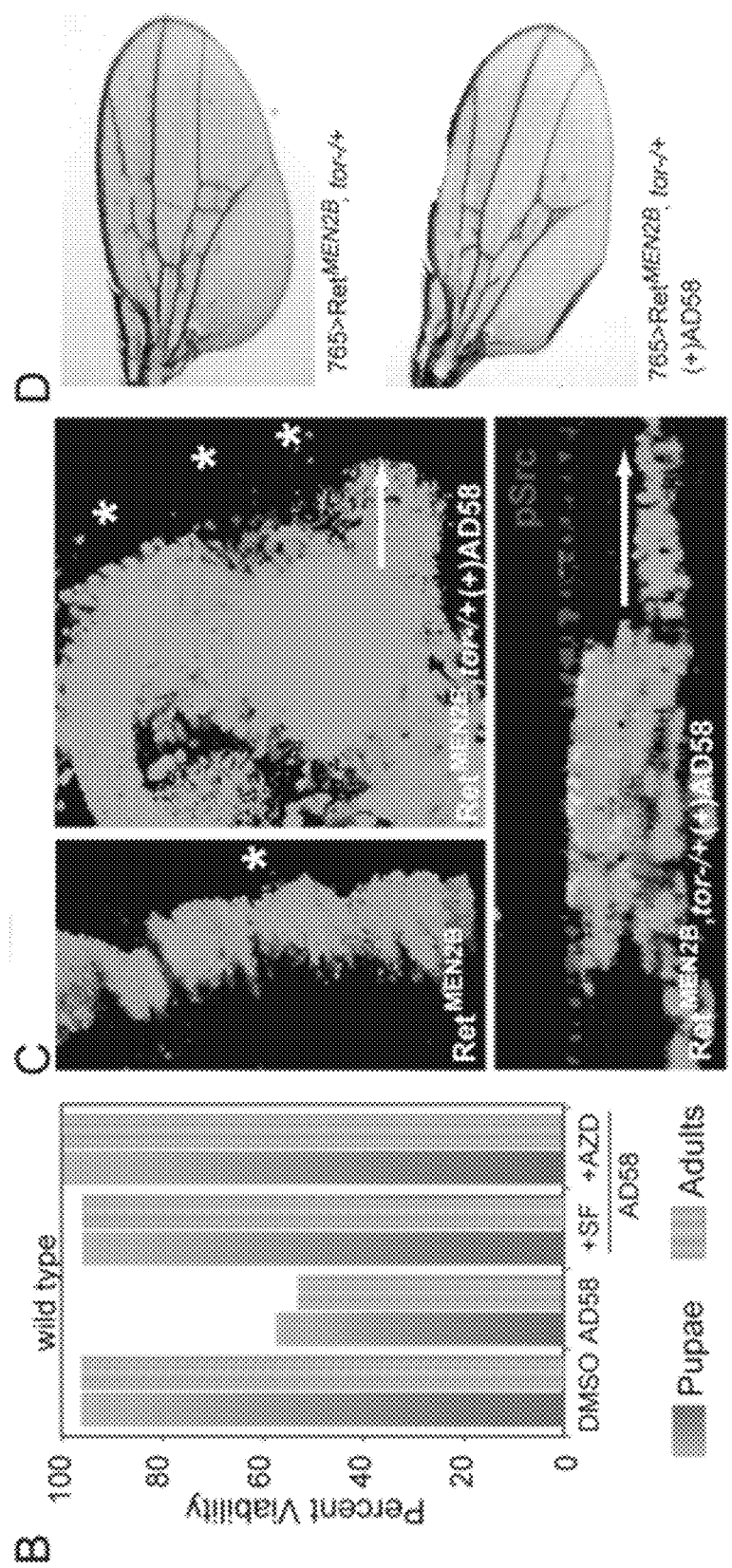
Figure 4:
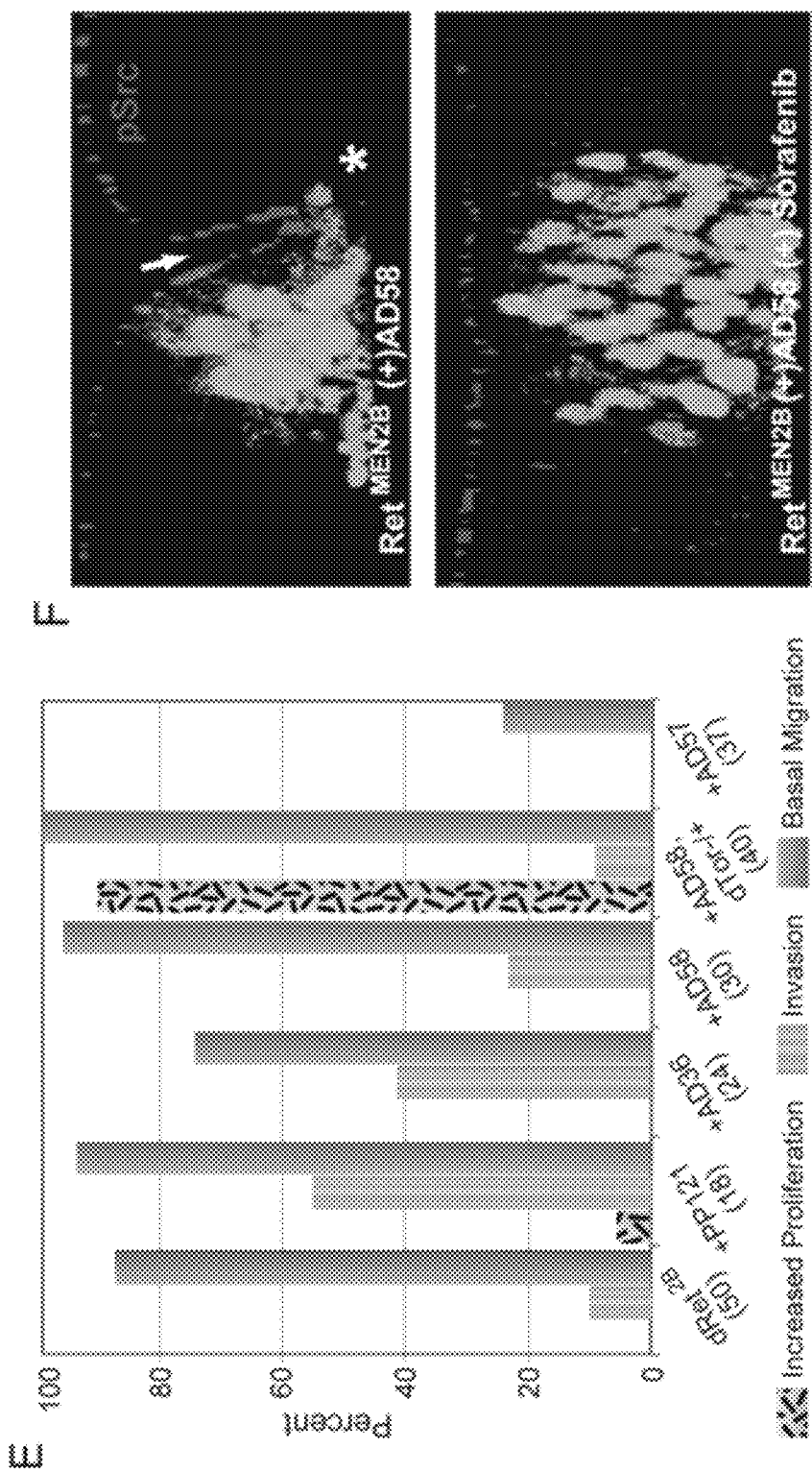

FIG. 4: Feedback up-regulation of the Ras pathway through the anti-target Tor.

A. Reducing for gene dosage decreased percent viability of both AD57 and AD58 treated $dRet^{MEN2B}$ flies. Conversely, reducing erk gene dosage (erk−/+) enhanced survival of both. Treatment with a specific MEK inhibitor alone, AZD6244, in control (ptc>$dRet^{MEN2B}$) or erk−/+ flies did not rescue viability compared to AD57 treated flies, suggesting its level of Ras pathway suppression is close to optimal. Reducing S6K−/+ partially mitigated toxicity from AD58 treatment.

B. Decreased viability of wild type flies by AD58 was mitigated by co-administration of Sorafenib or AZD6244.

C. Reducing for strongly enhanced AD58-mediated invasion (asterisks, arrow) and excess proliferation (compare to FIG. 2A). Upper images represent Z-series overlay of confocal images spanning the full depth of the wing disc epithelia; bottom panel presents a lateral reconstruction.

D. Wing defects in ptc>$dRet^{MEN2B}$, tor−/+ adults were further enhanced by AD58.

E. Quantification of ptc>$dRet^{MEN2B}$ phenotypes. Invasion was established by scoring for single/groups of GFP-labeled cells that relocated away from the ptc boundary (FIG. 4C, asterisks). Basal migration was scored as indentation of the apical surface (see FIG. 2B, arrows). Proliferation was scored as significant widening of the ptc boundary. The number of wings analyzed under each condition is indicated in brackets.

F. Migration of dRetMEN2B-transformed cells was blocked by co-treatment with AD58 plus Sorafenib. Treatment with similar doses of AD58 (FIG. 2B) or Sorafenib alone did not suppress migration.

Figure 5:
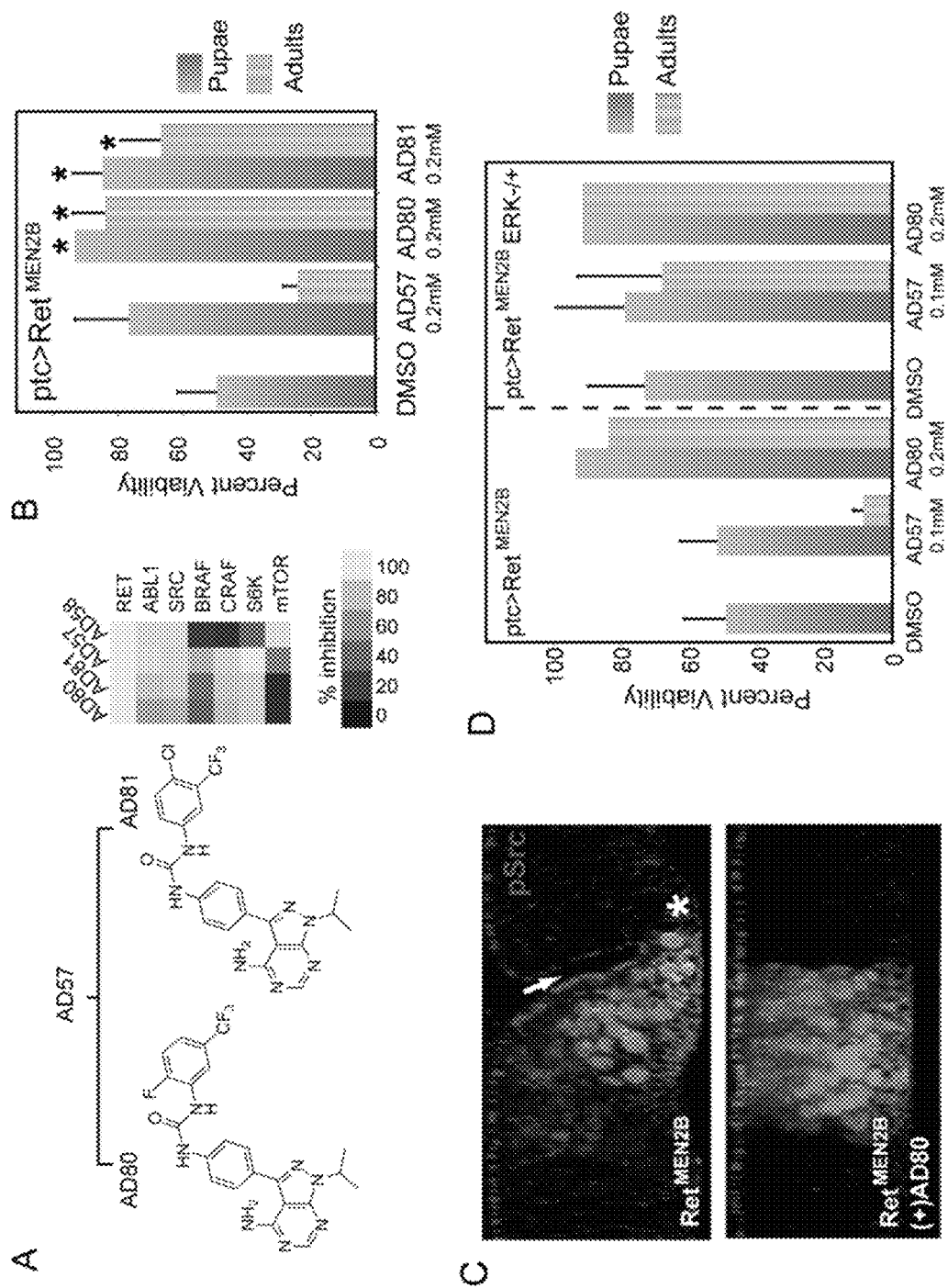
Figure 5:
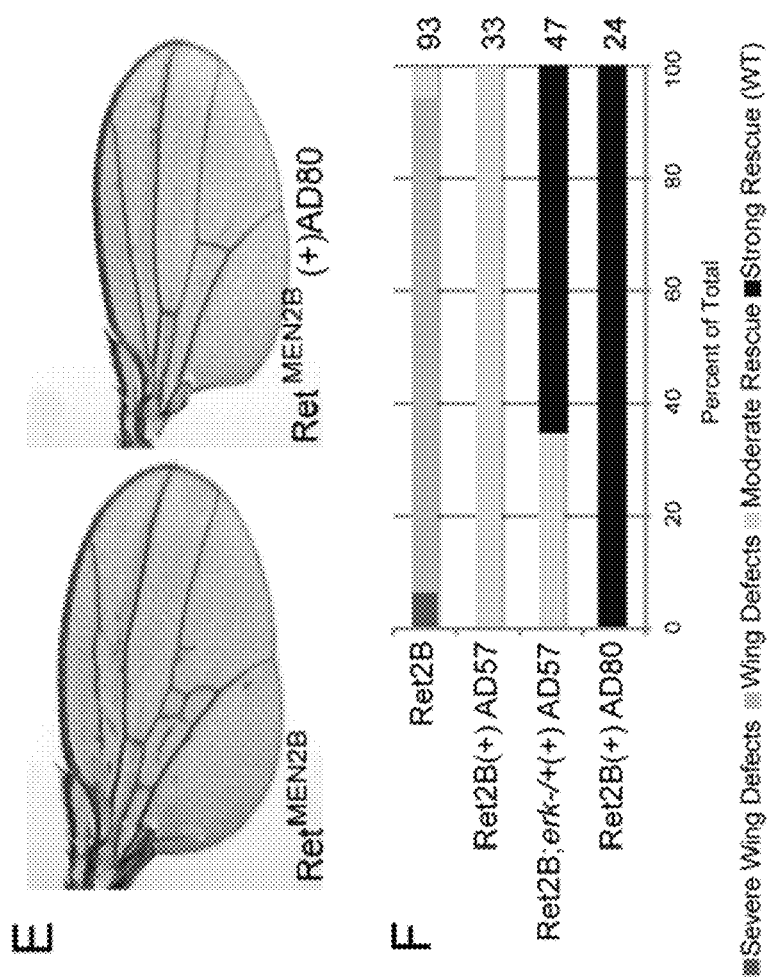
Figure 5:
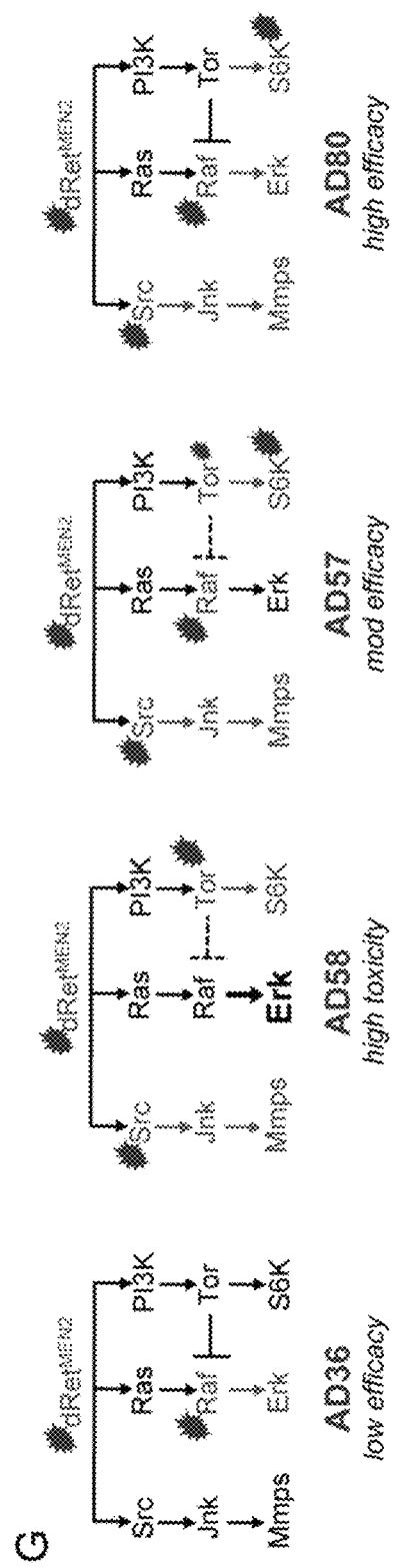

FIG. 5: Balanced kinase polypharmacology provides optimal efficacy and toxicity.

A. Chemical structures of the AD57 derivatives AD80 and AD81 and at 1 microM their percent inhibition of relevant targets. Unlike AD57 and AD58, both inhibitors lack significant inhibitory activity against mTOR.

B. AD80 and AD81 displayed improved rescue relative to AD57.

C. Basal migration (arrow) of dRet$^{MEN2}$ cells and basal phospho-Src (asterisk) were potently blocked by AD80.

D. Reducing erk gene dosage (erk-/+) enhanced survival of AD57 but not AD80, suggesting that an ERK feedback loop was not altered by AD80 and that Erk was optimally suppressed.

E. 765>dRet$^{MEN2B}$-dependent extra wing vein phenotype was potently rescued by AD80.

F. Quantification of wing defects demonstrate the improved efficacy provided by AD80. The number of wings analyzed under each treatment is indicated to the right of the graph.

G. Summary and models to explain the differential outcomes of the AD series of compounds in dRet$^{MEN2B}$ transgenic flies. The polypharmacological profile of AD80 best addresses the three key pathways, providing an optimal therapeutic index.

Figure 6:
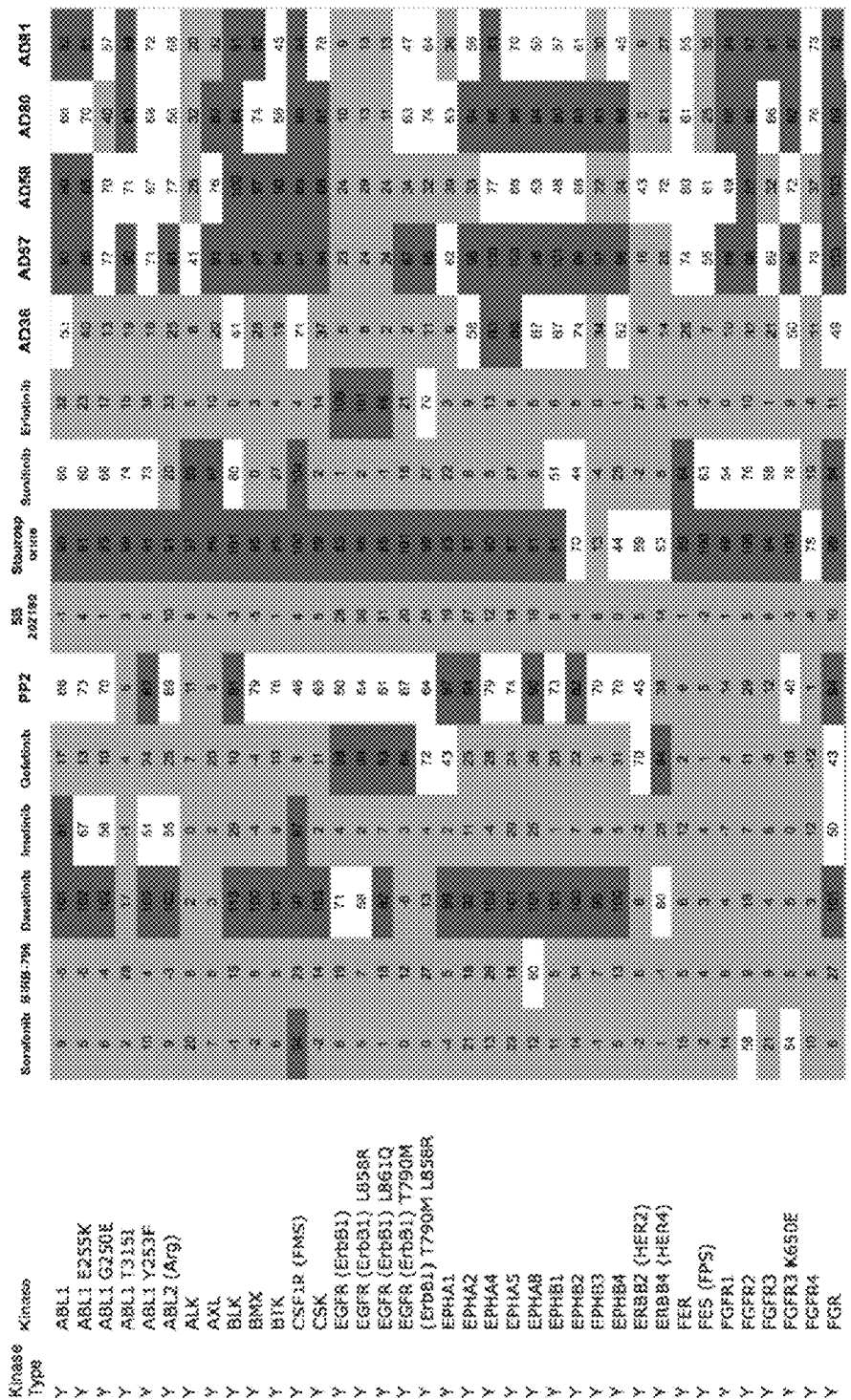
Figure 6:
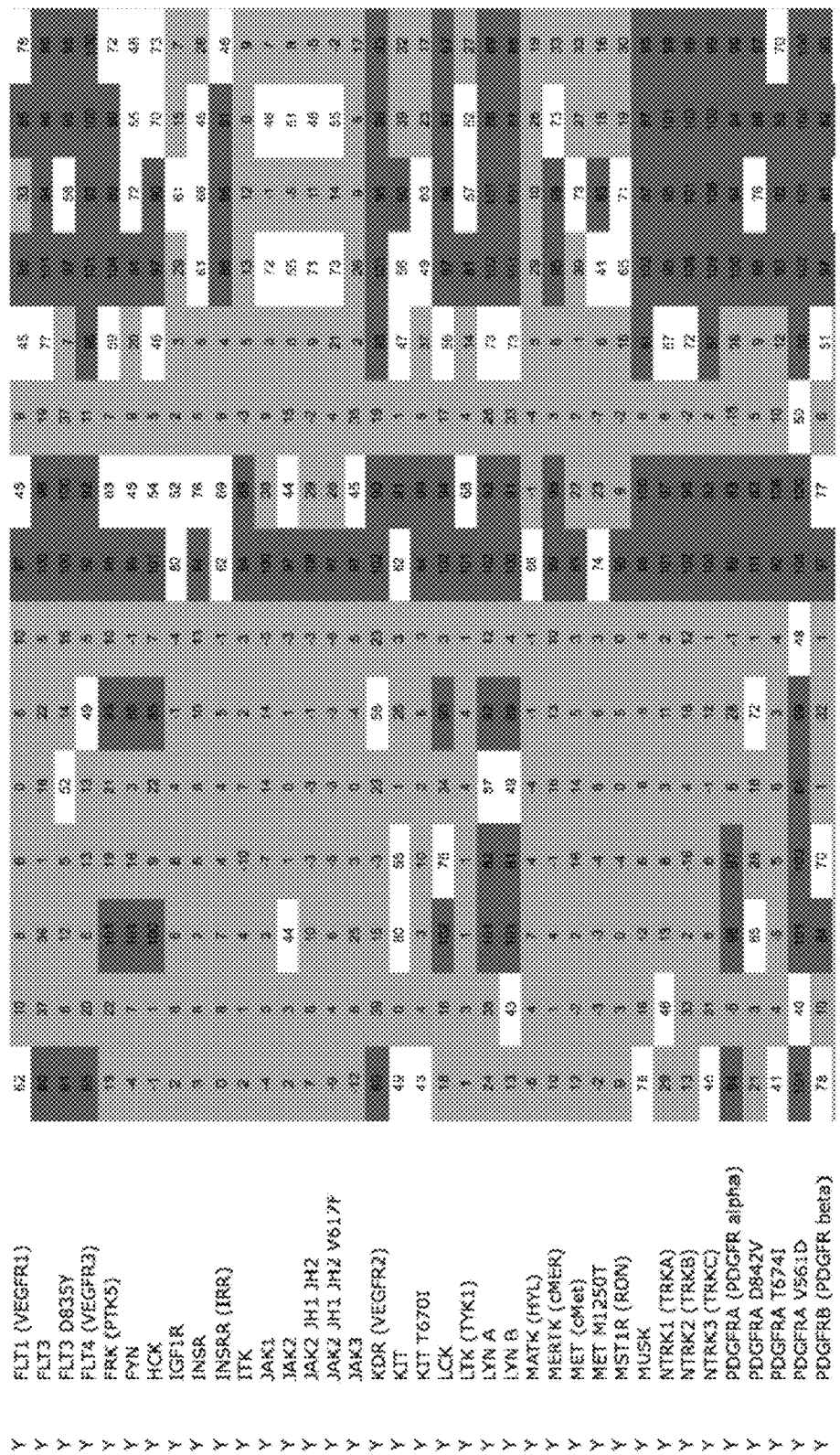
Figure 6:
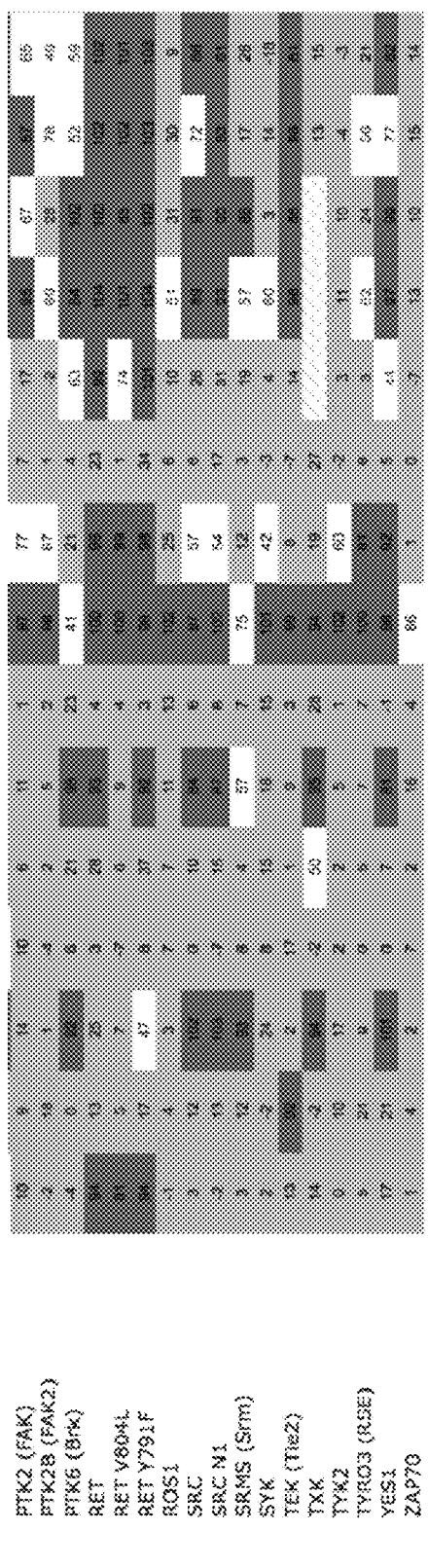

FIG. 6 Select Screen Inhibition Data for Tyrosine Kinases. Percent inhibition of kinase activity. Dark gray is greater than 80% inhibition, white is 40-80% inhibition, and light gray is less than 40% inhibition. Hashed boxes indicate no useful data was obtained. Full assay conditions described at www.invitrogen.com/kinaseprofiling.

Figure 7:
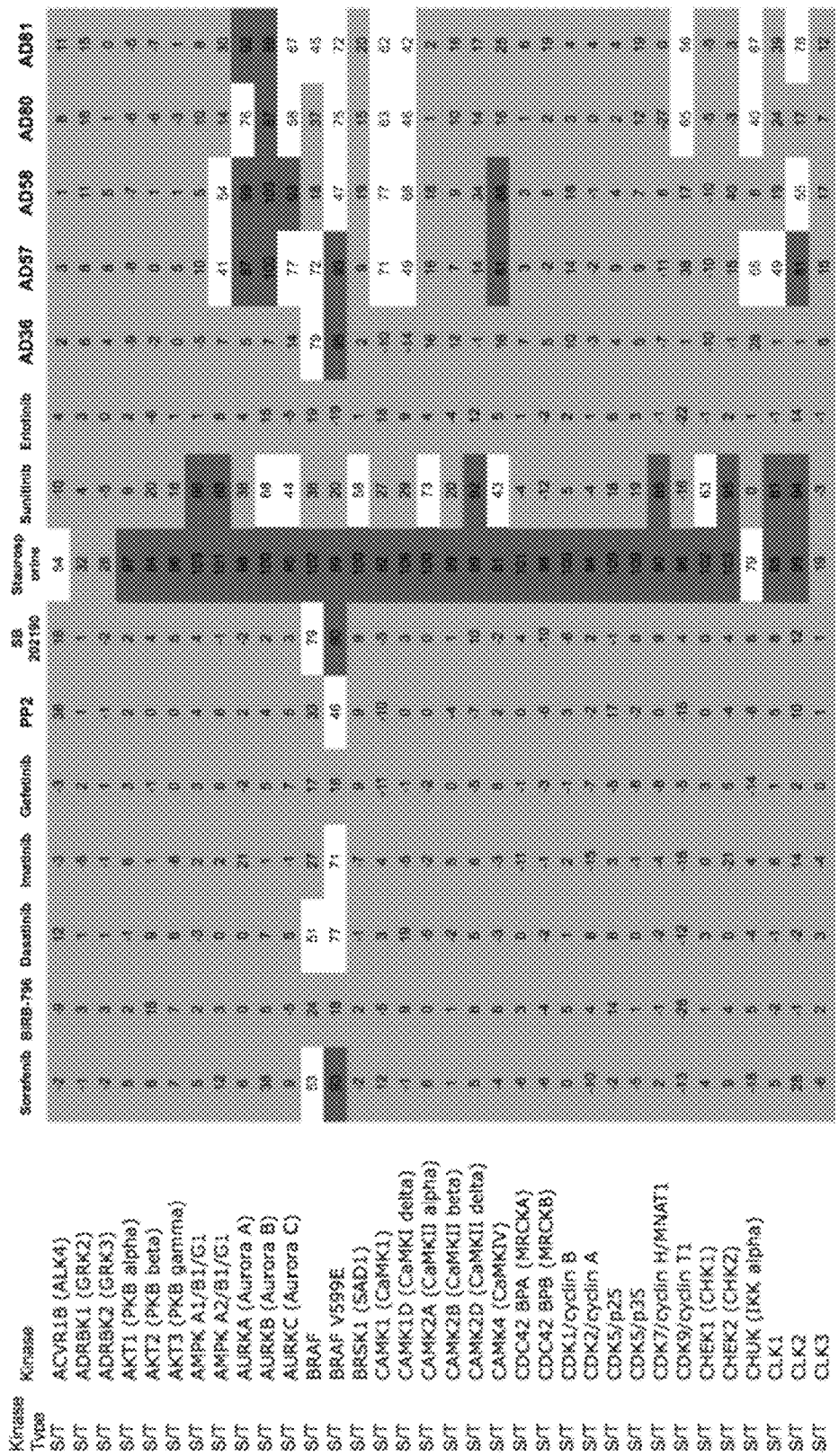
Figure 7:
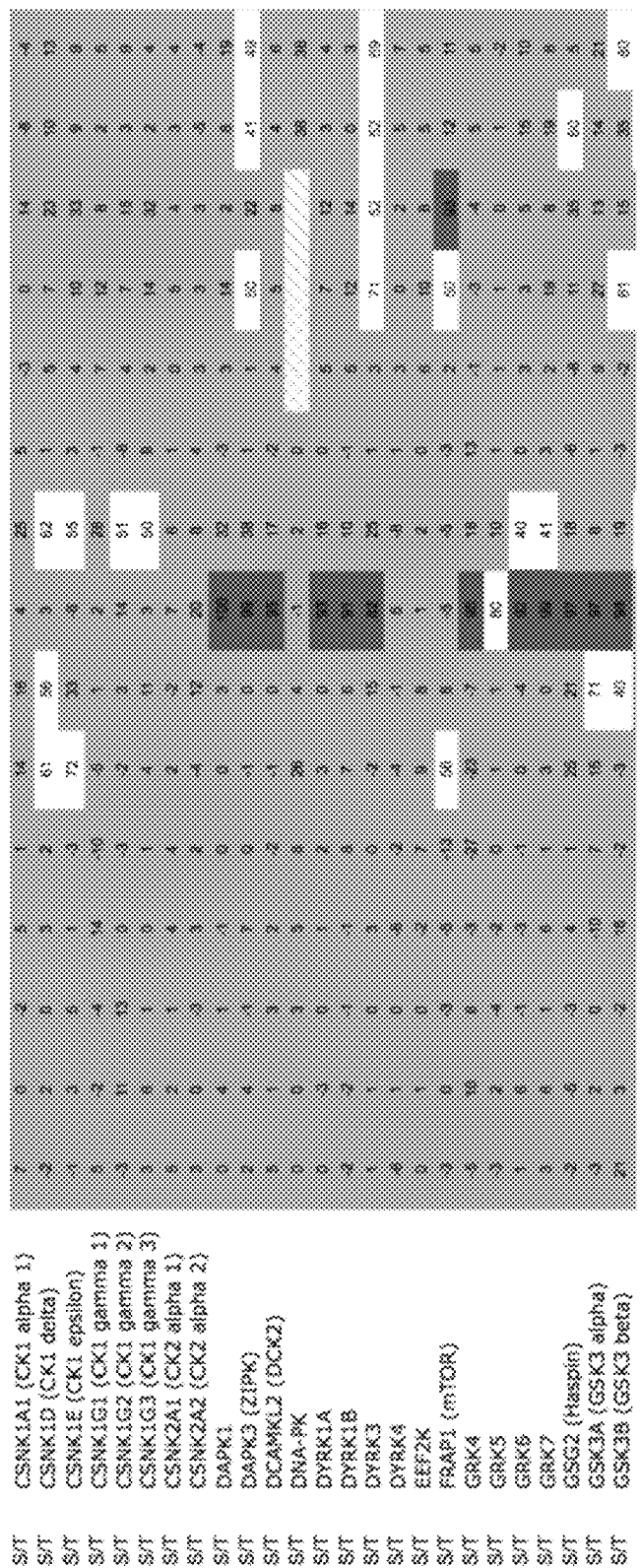
Figure 7:
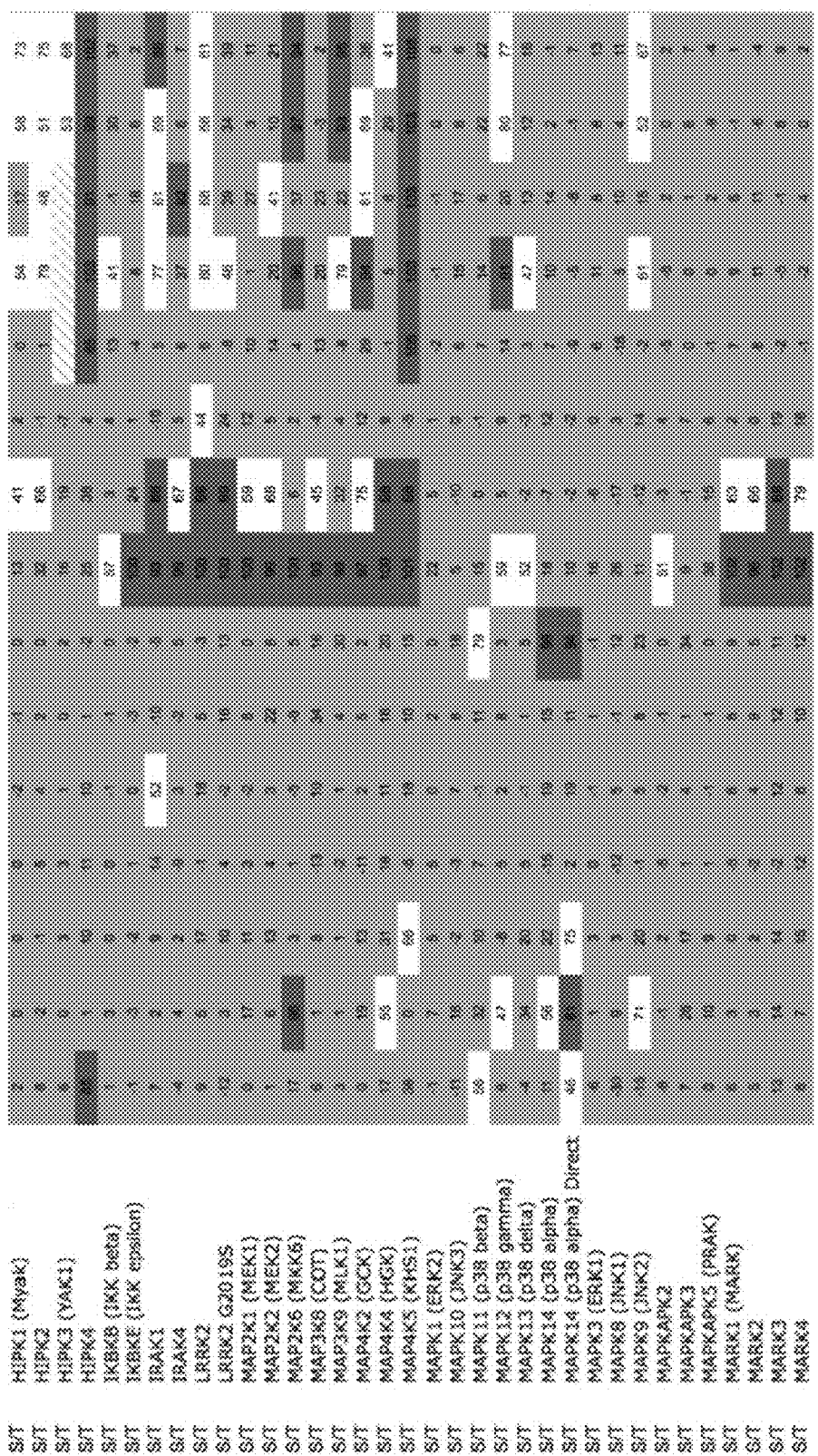
Figure 7:
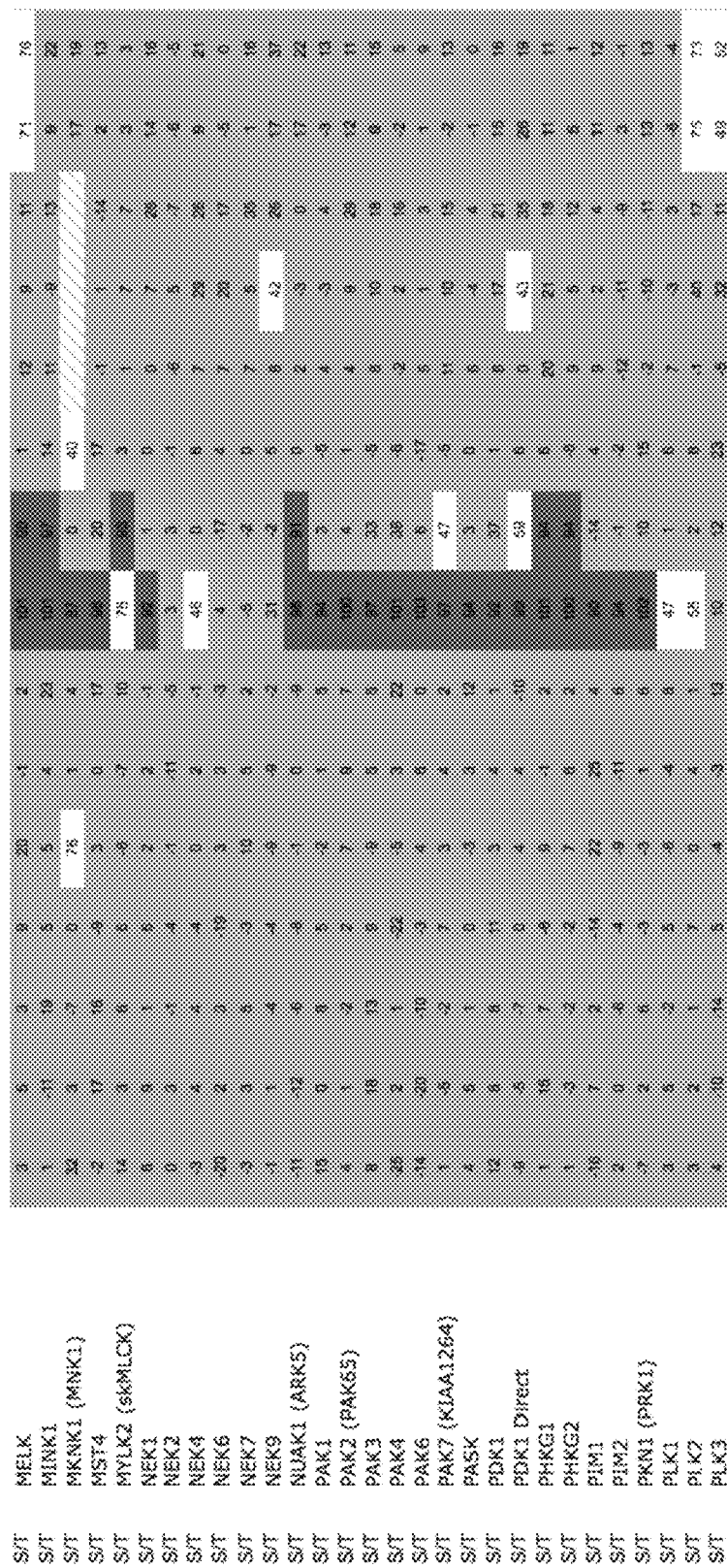
Figure 7:
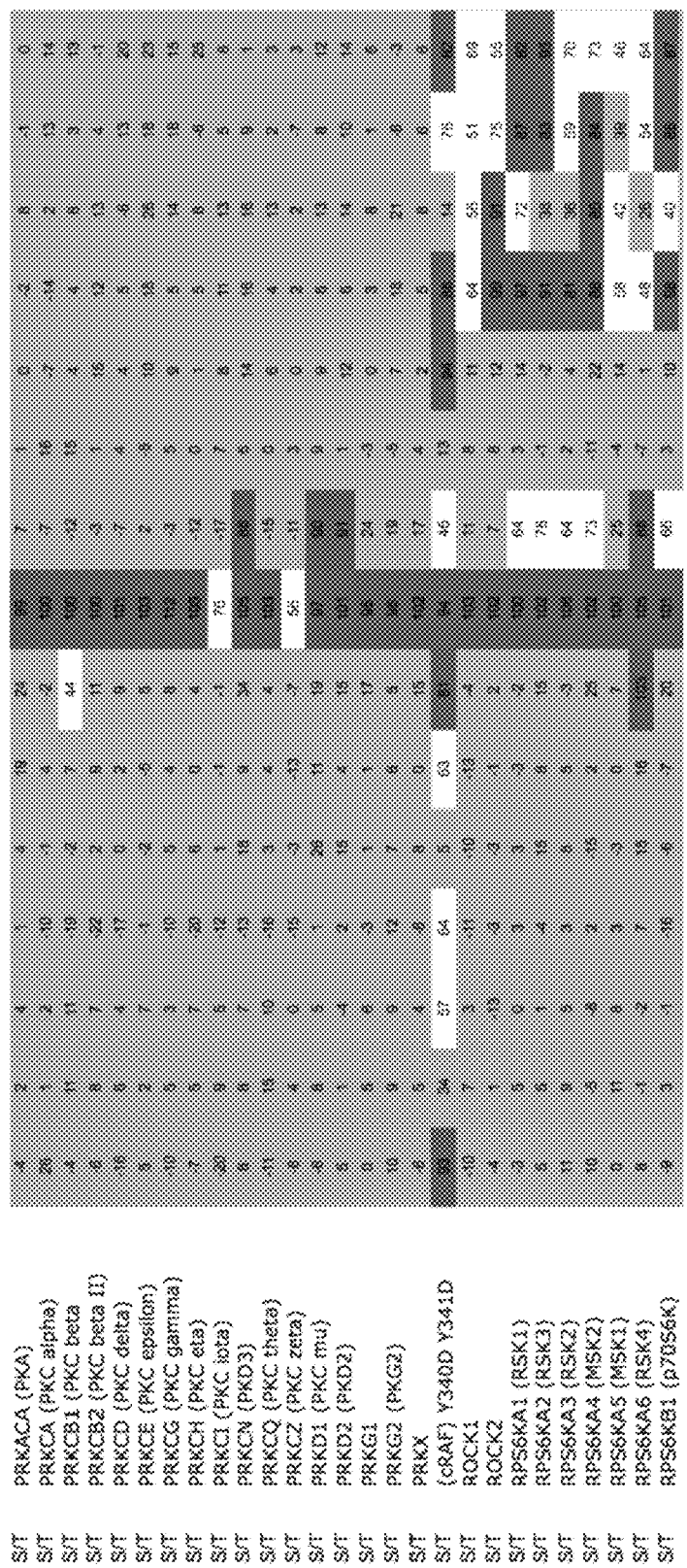
Figure 7:
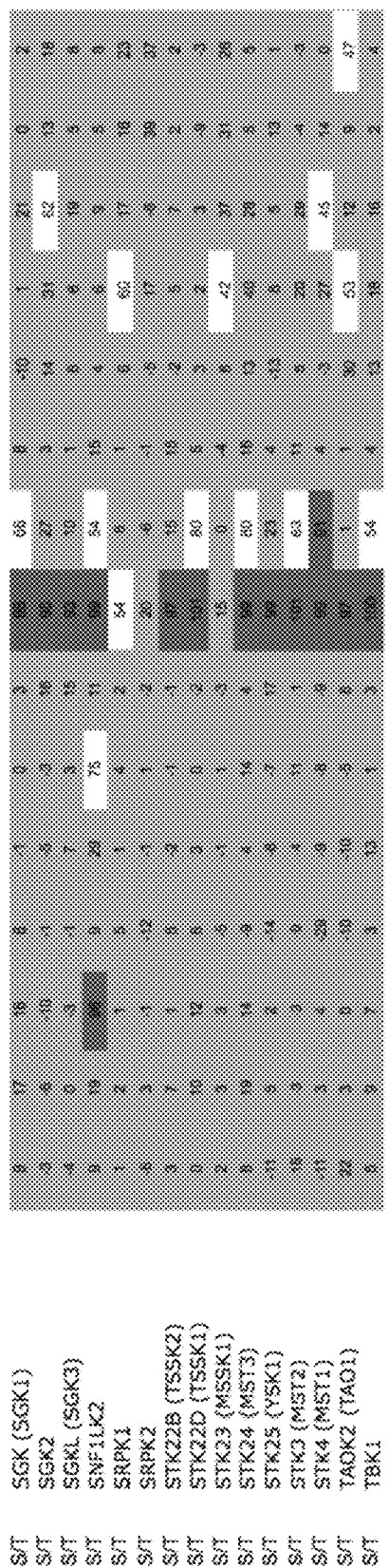

FIG. 7 Select Screen Inhibition Data for Serine/Threonine Kinases. Percent inhibition of kinase activity. Dark gray is greater than 80% inhibition, white is 40-80% inhibition, and light gray is less than 40% inhibition. Hashed boxes indicate no useful data was obtained. Full assay conditions described at www.invitrogen.com/kinaseprofiling.

Figure 8:
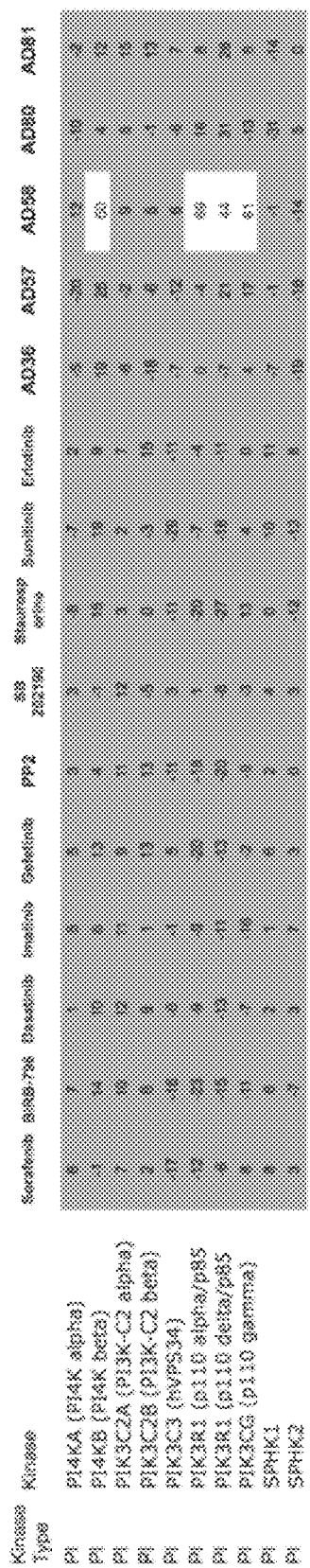

FIG. 8 Select Screen Inhibition Data for Lipid Kinases. Percent inhibition of kinase activity. Dark gray is greater than 80% inhibition, white is 40-80% inhibition, and light gray is less than 40% inhibition. Hashed boxes indicate no useful data was obtained. Full assay conditions described at www.invitrogen.com/kinaseprofiling.

Figure 9:
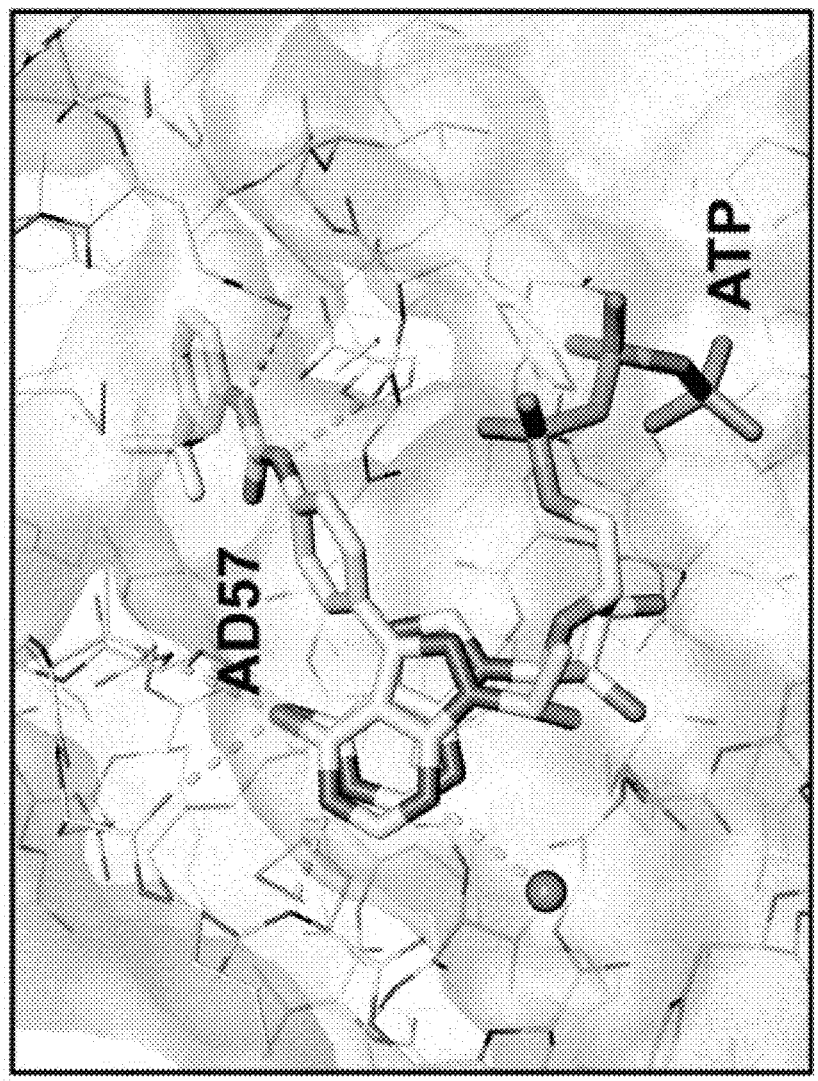
Figure 10A:
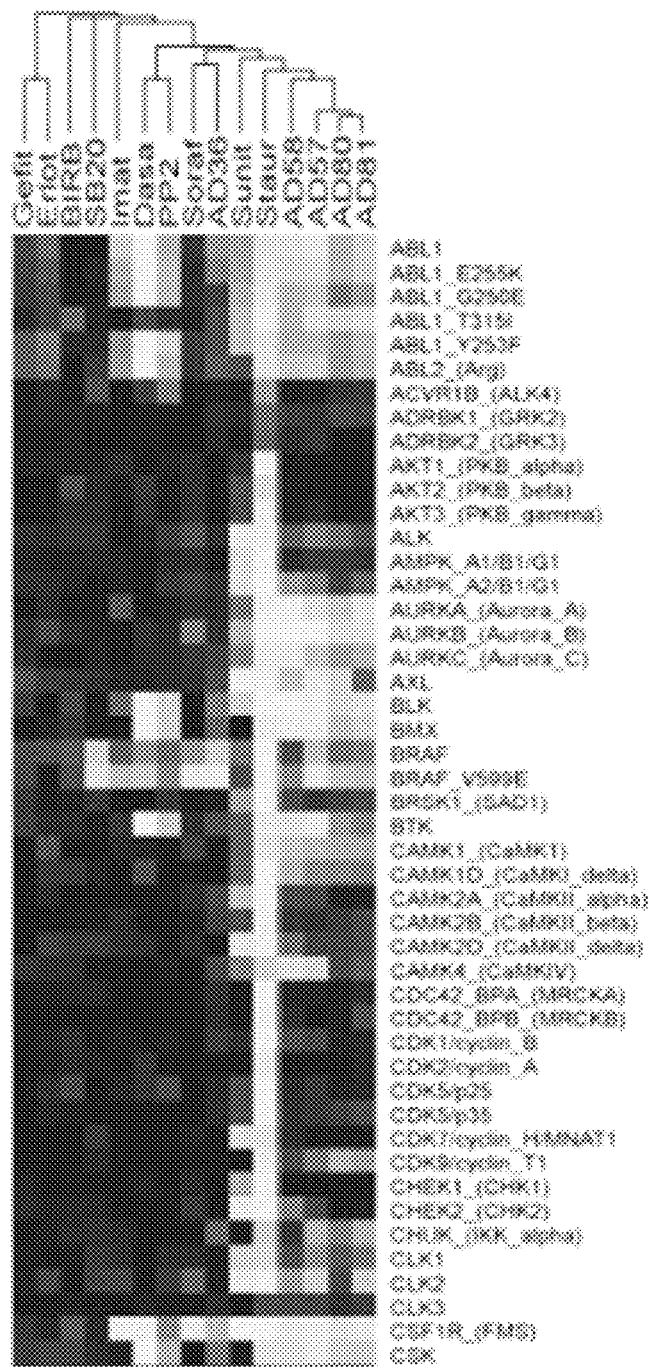
Figure 10A:
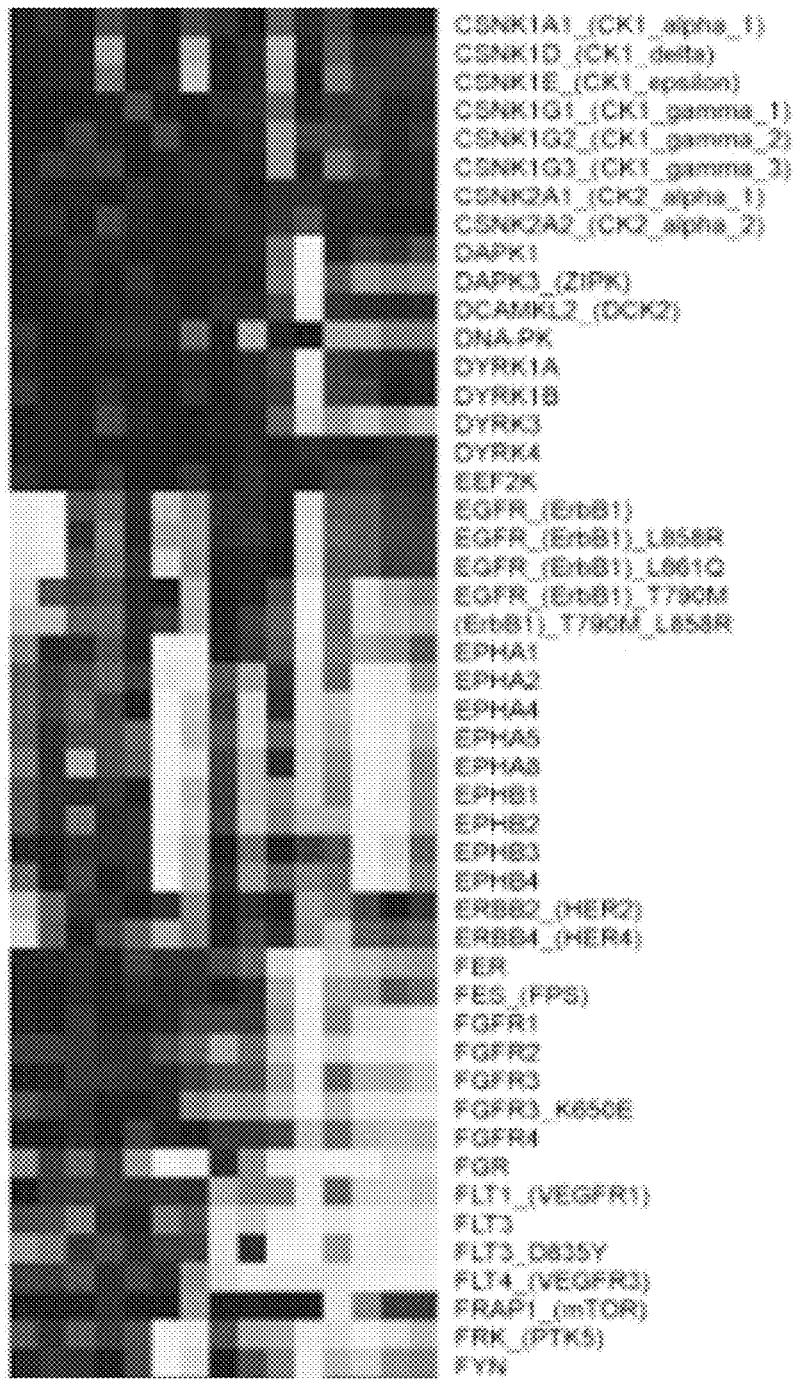
Figure 10A:
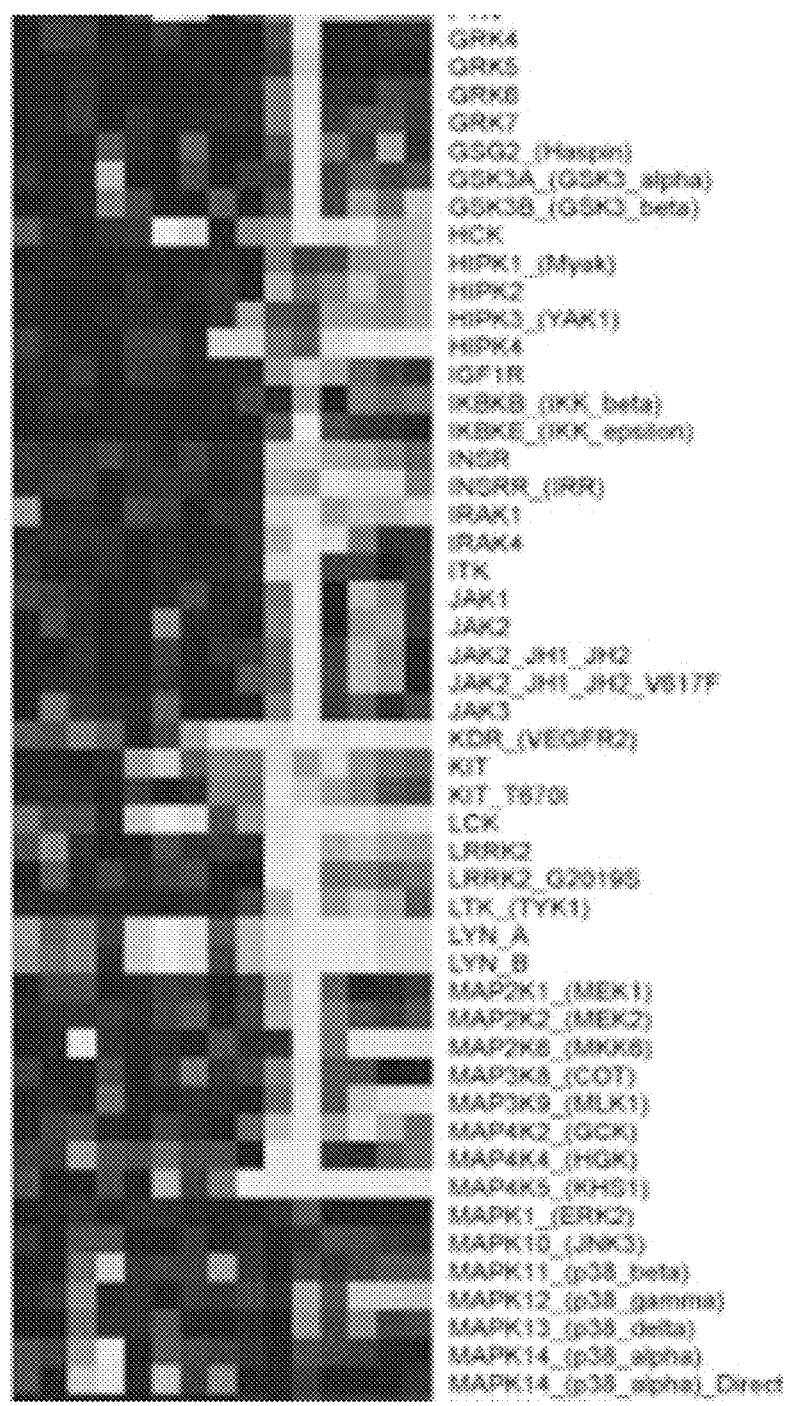
Figure 10A:
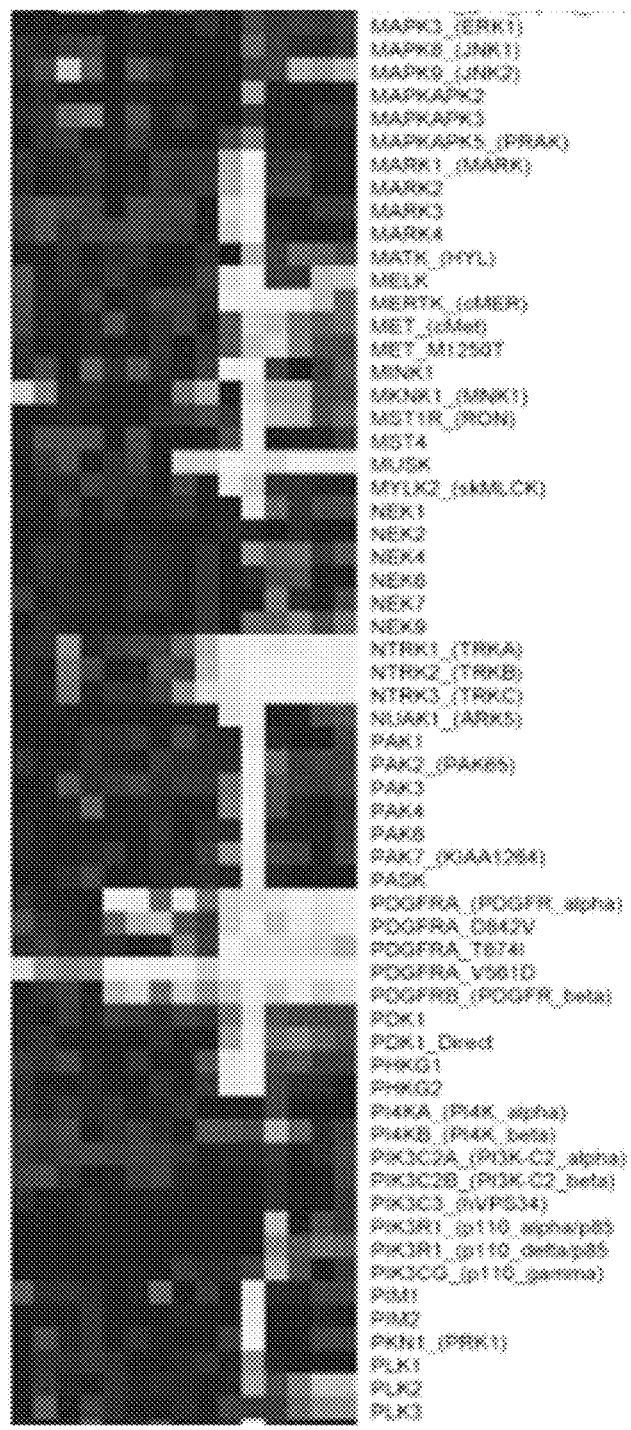
Figure 10A:
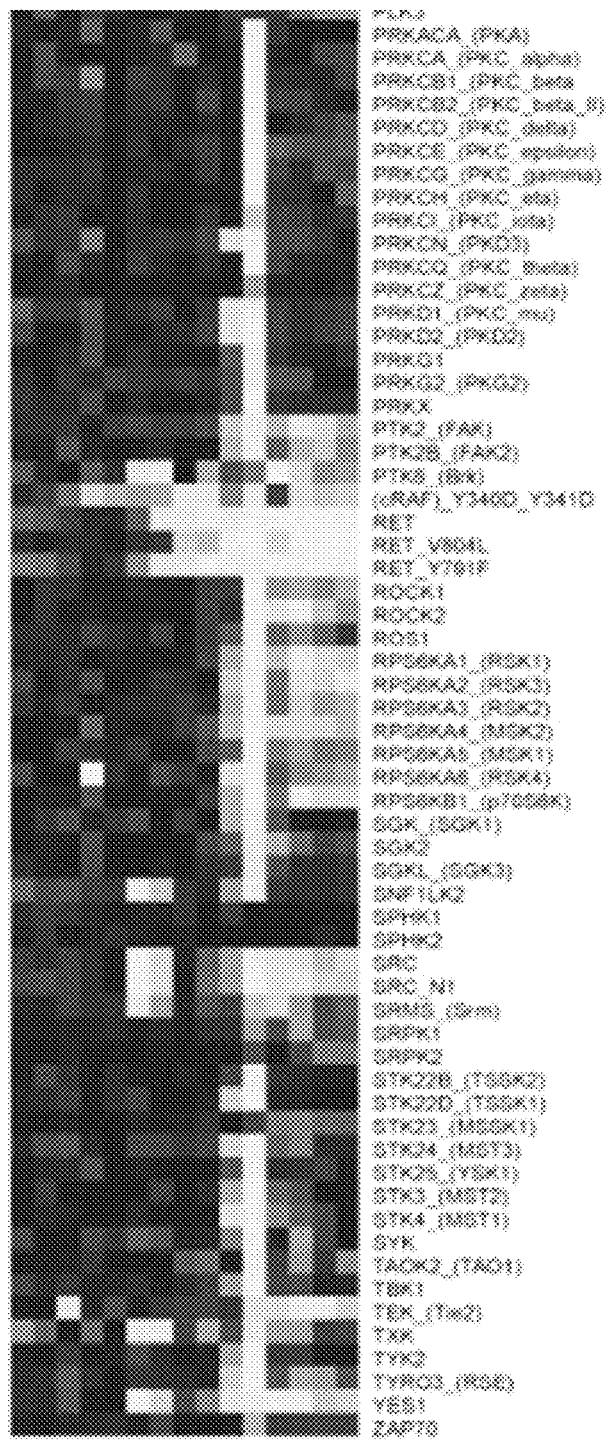
Figure 10B:
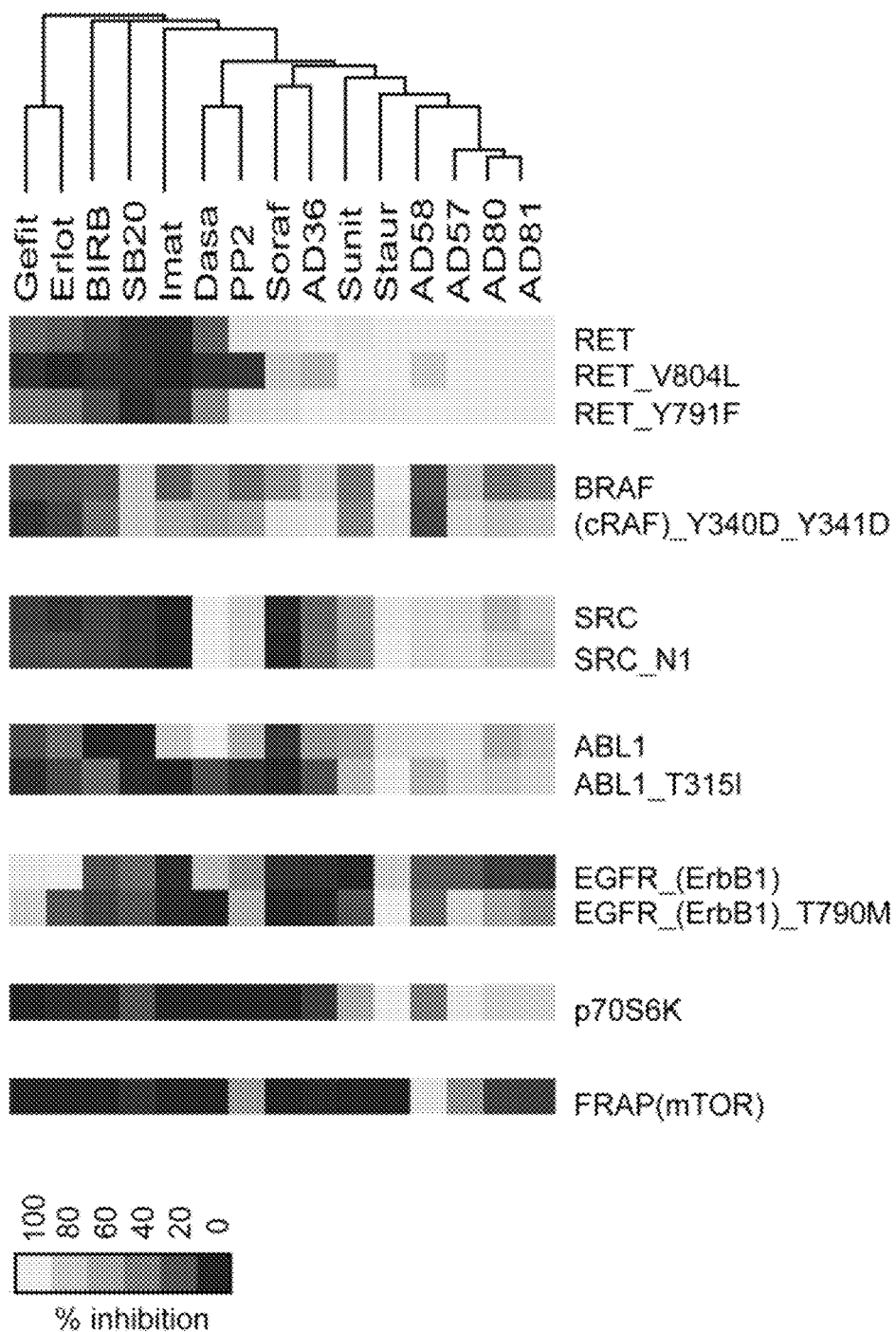

FIG. 9: AD57 is a type II kinase inhibitor.

X-ray crystal structure of AD57 bound to c-SRC (PDB ID: 3EL8). ATP was modeled based on structural overlay.

FIG. 10. Inhibitor Clustering Based on Kinase Profiling Data.

A. The entire data set includes 15 inhibitors (1 μM) tested against 222 kinases, respectively for a total of 3330 data points. Short forms of inhibitor names include Gefit (Gefitinib), Erlot (Erlotinib), BIRB (BIRB-790), Imat (Imatinib), Dasa (Dasatinib), Soraf (Sorafenib), Sunit (Sunitinib), and Staur (Staurosporine). Tree indicates similarity of compounds based on hierarchical clustering of percent kinase inhibition.

B. Selectivity profiles for a subset of kinases. The gatekeeper mutant alleles of RET, ABL1, and EGFR are V804L, T315I and T790M, respectively.

FIG. 11. Summary of the effects of AD57, AD80 and Vandetanib on tumor growth in the MEN2 (TT) xenograft model. TT thyroid cancer cells were implanted into athymic nu/nu mice subcutaneously into the right flank under the conditions listed. Upon establishment of tumors, drugs were administered by oral gavage (5 days ON/2 days OFF schedule). Tumors were measured using digital calipers. Experiment A lists starting and end point data from FIG. 2B. Experiment B lists starting and end point data from FIG. 17. VD=vandetanib.

Figure 12:
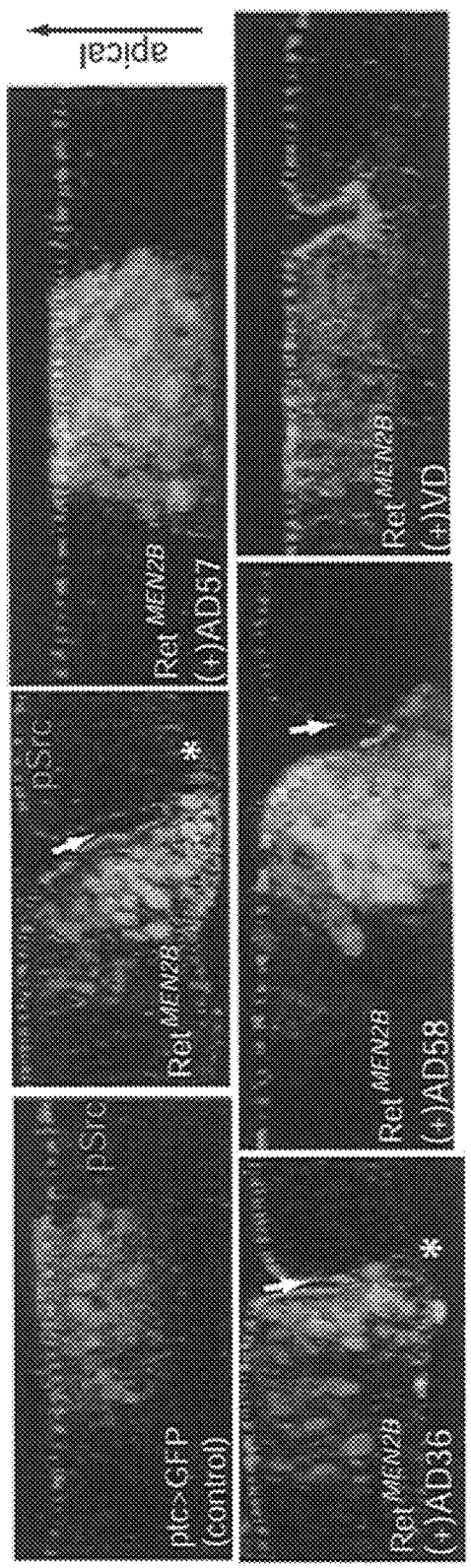

FIG. 12. Multi-pathway inhibition by AD57 mitigates dRet-driven phenotypes in the fly. Z-series confocal images of larval wing epithelia. Control tissue shows apical phospho-Src expression (labeled) in the junctions. ptc>dRet$^{MEN2B}$ wing cells (GFP$^+$) shifted basally (arrows) and invaded into adjacent wild type tissue; phospho-Src emerged at the basal invading front (asterisks). These phenotypes were strongly suppressed by AD57 but not by AD36, AD58, or Vandetanib (VD).

Figure 13:
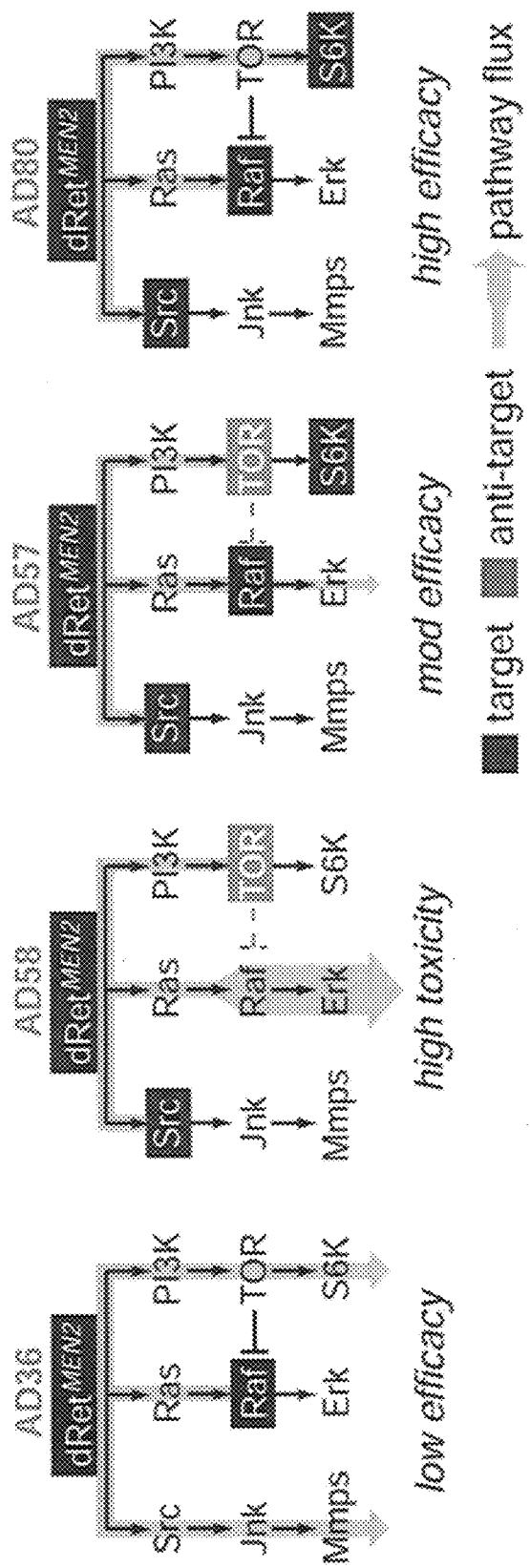

FIG. 13. Balanced kinase polypharmacology provides optimal efficacy and toxicity. Models to explain the differential outcomes of the AD series of compounds in dRet$^{MEN2B}$ transgenic flies. Pathway components blocked by inhibitors have been boxed with resulting flux indicated by light gray lines/arrows. Grey targets contribute to efficacy whereas inhibition of the anti-target dTor (gray box with white letters) leads to hyperactivation of the Ras pathway causing high toxicity in the MEN2 model. The polypharmacological profile of AD80 best addresses the three key pathways, providing high drug efficacy and optimal therapeutic index.

Figure 14:
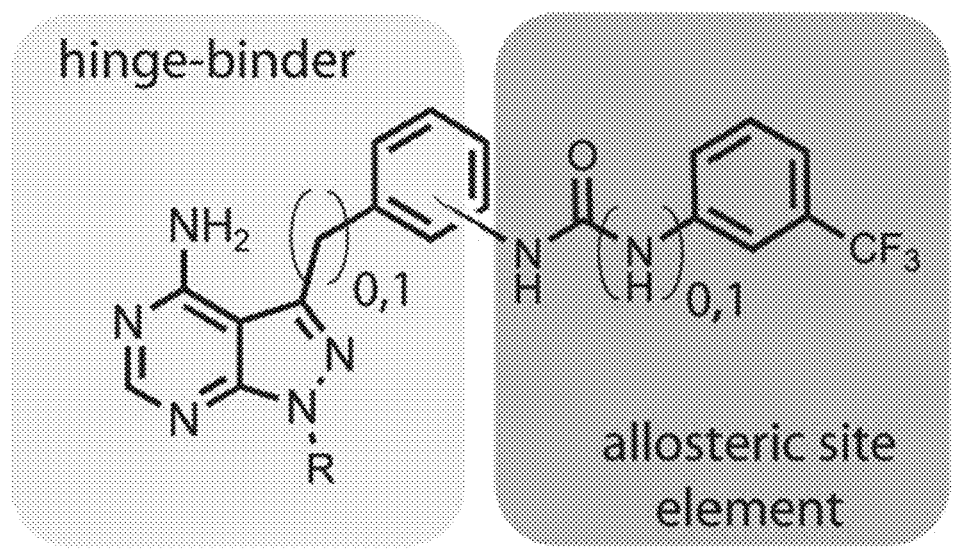

FIG. 14. The general chemical formula of AD57-like small molecules. The hinge binder mimics H-bond interactions at the kinase domain hinge that are analogous to those made by Adenine. The allosteric site element binds within an allosteric pocket formed by movement of the conserved DFG-triad.

Figure 15:
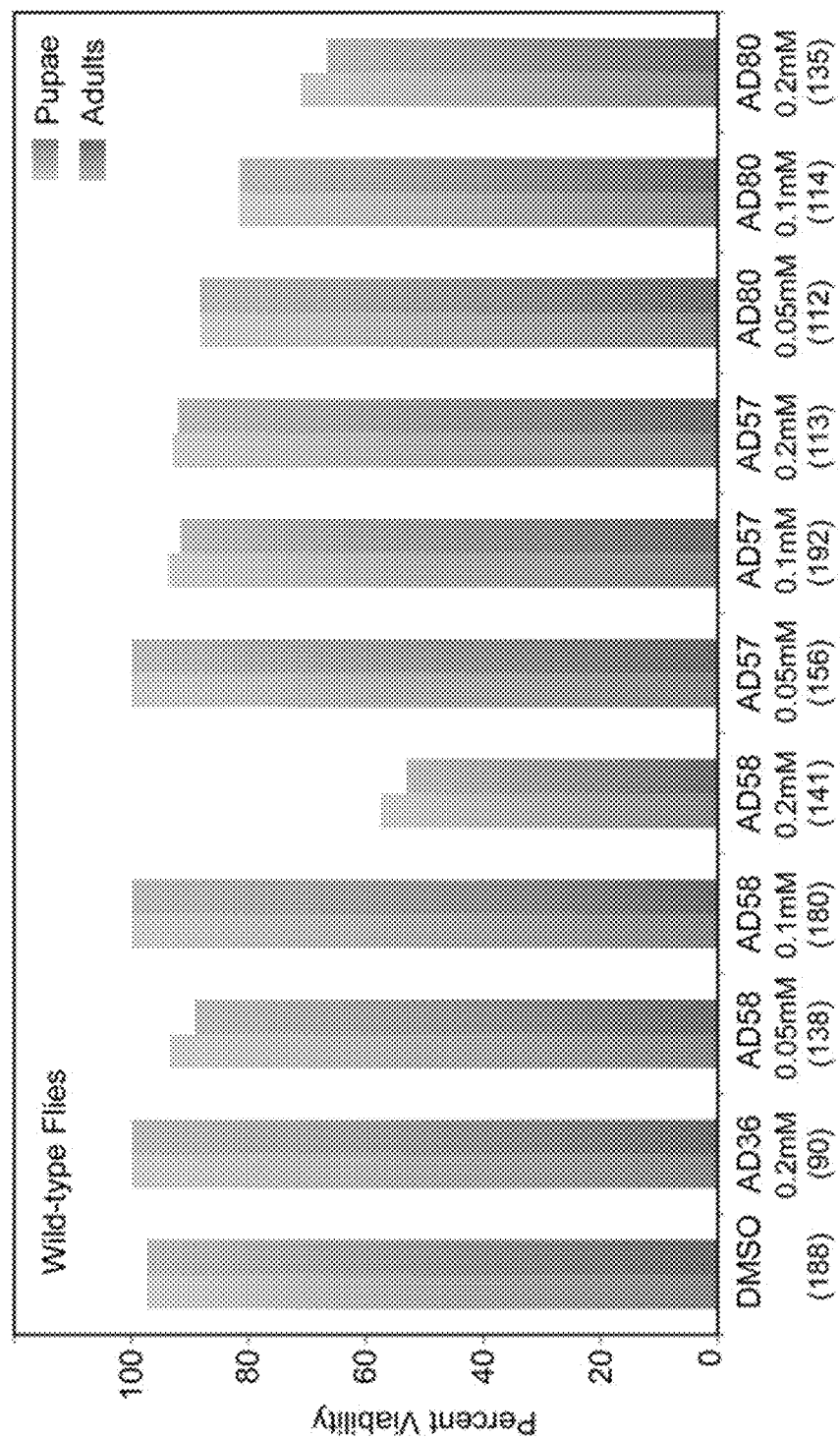

FIG. 15. Percent viability of control and drug treated wild-type flies (WT). The proportion of WT pupae and adults that survived from the total number of embryos (indicated in brackets below) are represented as column graphs. (Pupae left, Adults right)

Figure 16:
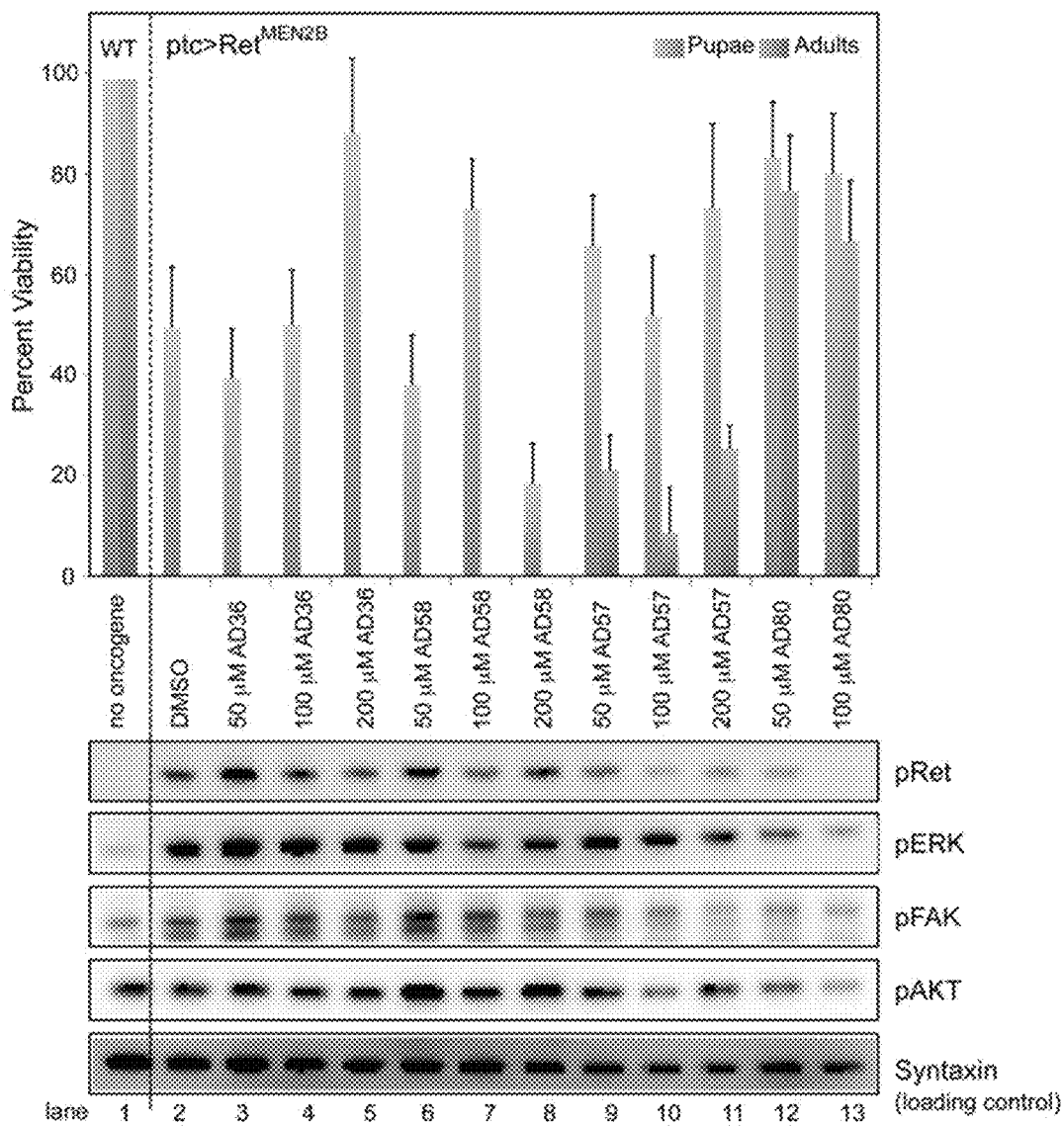

FIG. 16. Rescue and Immunoblot Analysis of Drug-treated Flies. (Above) Percent viability of WT and ptc>Ret$^{MEN2B}$ flies are shown with indicated drug treatments. Drug rescue was scored as the percent viable pupae and adults. (Pupae left, Adults right) (Below) Under identical conditions, flies were harvested at the larvae stage following three days of drug treatment. Approximately 10 imaginal discs per condition were isolated and subjected to cell lysis. Equal protein loading prior to running gel was assessed by Bradford Assay. Cell extracts were immunoblotted to detect the indicated proteins.

Figure 17:
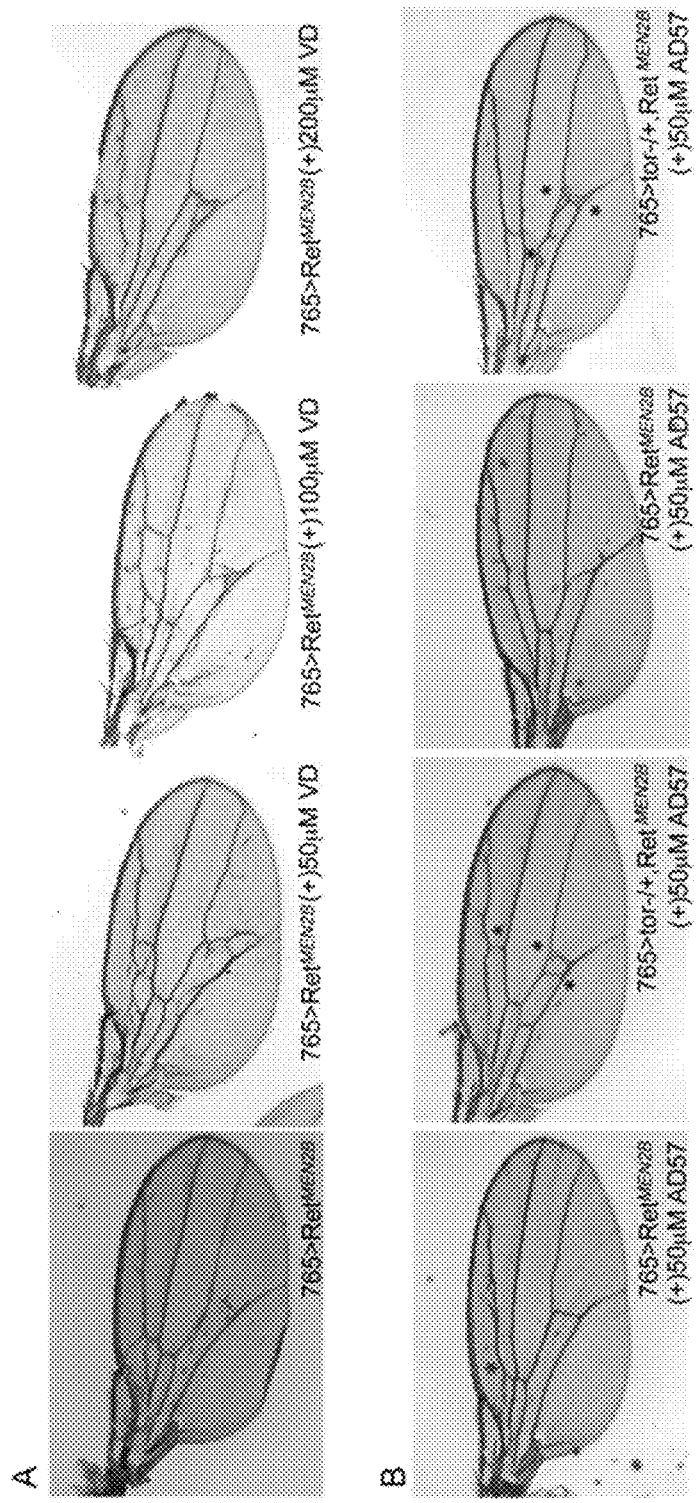

FIG. 17. S Modulation of Ectopic Wing Pattern and Vein Formation in Ret$^{MEN2B}$ Flies. Expression of Ret$^{MEN2B}$ throughout the wing led to ectopic wing defects, which were not suppressed by treatment with increasing amounts of Vandetanib (A). Whereas, wing rescue by AD57 was reversed by reducing gene dosage of dTor (two examples are shown in B). Asterisks indicate ectopic wing-veins as well as increased thickening, both of which are markers of excess erk activity. dRet$^{MEN2B}$-dependent wing phenotypes were suppressed with AD57 treatment (FIG. 3D); by contrast, Vandetanib had little effect (FIG. 17B). Reducing the gene dosage of dTor suppressed efficacy of AD57 on wing vein pattern (FIG. 17B), indicating that reducing dTor increased Erk activity.

Figure 18:
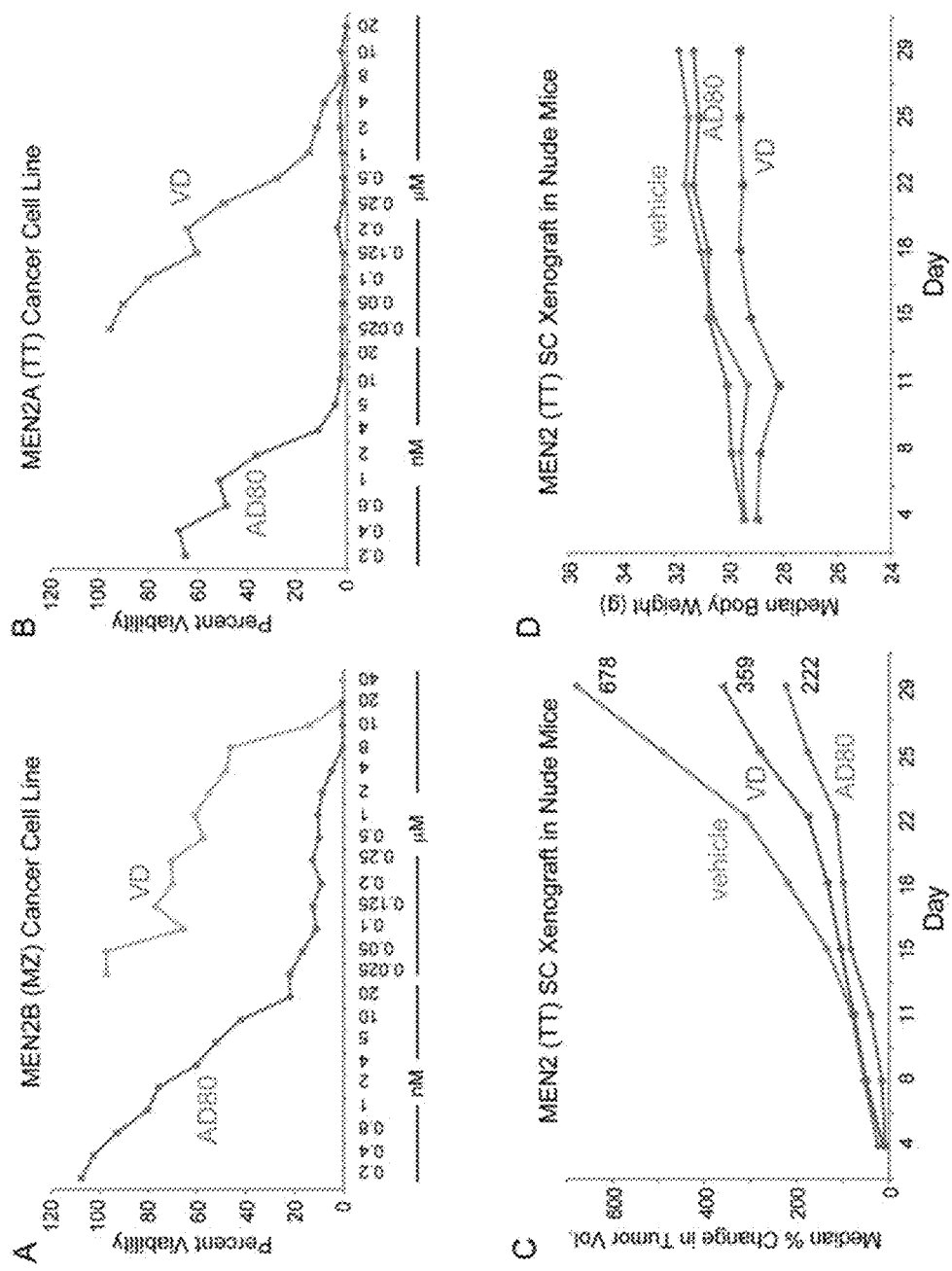

FIG. 18. AD80 inhibits tumor growth in culture and in a mouse xenograft model. A. MEN2B (MZ) thyroid cancer cells were treated with the indicated concentrations of each inhibitor (7 days) and cell viability was quantitated by MTT assay. B. MEN2A (TT) thyroid cancer cells were treated with the indicated concentrations of each inhibitor (7 days)

and cell viability was quantitated by MTT assay. C. AD80 and Vandetanib (VD) reduce tumor progression 3.1- and 1.9-fold, respectively, relative to vehicle treated nude mice transplanted with TT cells. Change in tumor volume was calculated per mouse. Values shown are the median percent change per group. 20 and 10 animals for vehicle and drug treated mice, respectively, were analyzed. D. Body weight measurements of AD80, Vandetanib (VD) and vehicle treated nude mice transplanted with TT cells. Values shown are the median of 20 and 10 animals for vehicle and drug treated mice, respectively.

Figure 19:
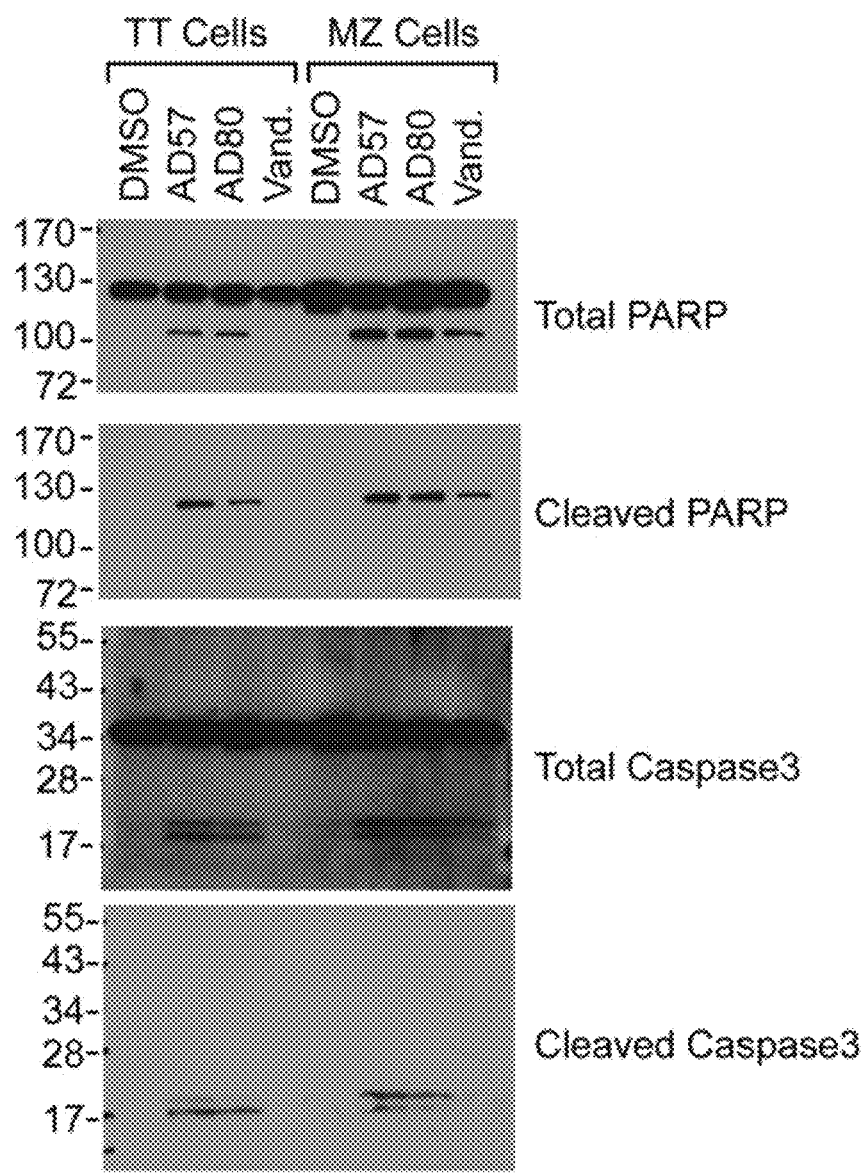

FIGS. 19. AD57 and AD80 induce cell death. MEN2A (TT) and MEN2B (MZ) thyroid cancer cells were treated with the indicated drugs for 3 days at a final concentration of 2 μM. Cell lystates were immunoblotted for protein markers of apoptosis. Vandetanib (vand.) was included for comparison.

Figure 20A:
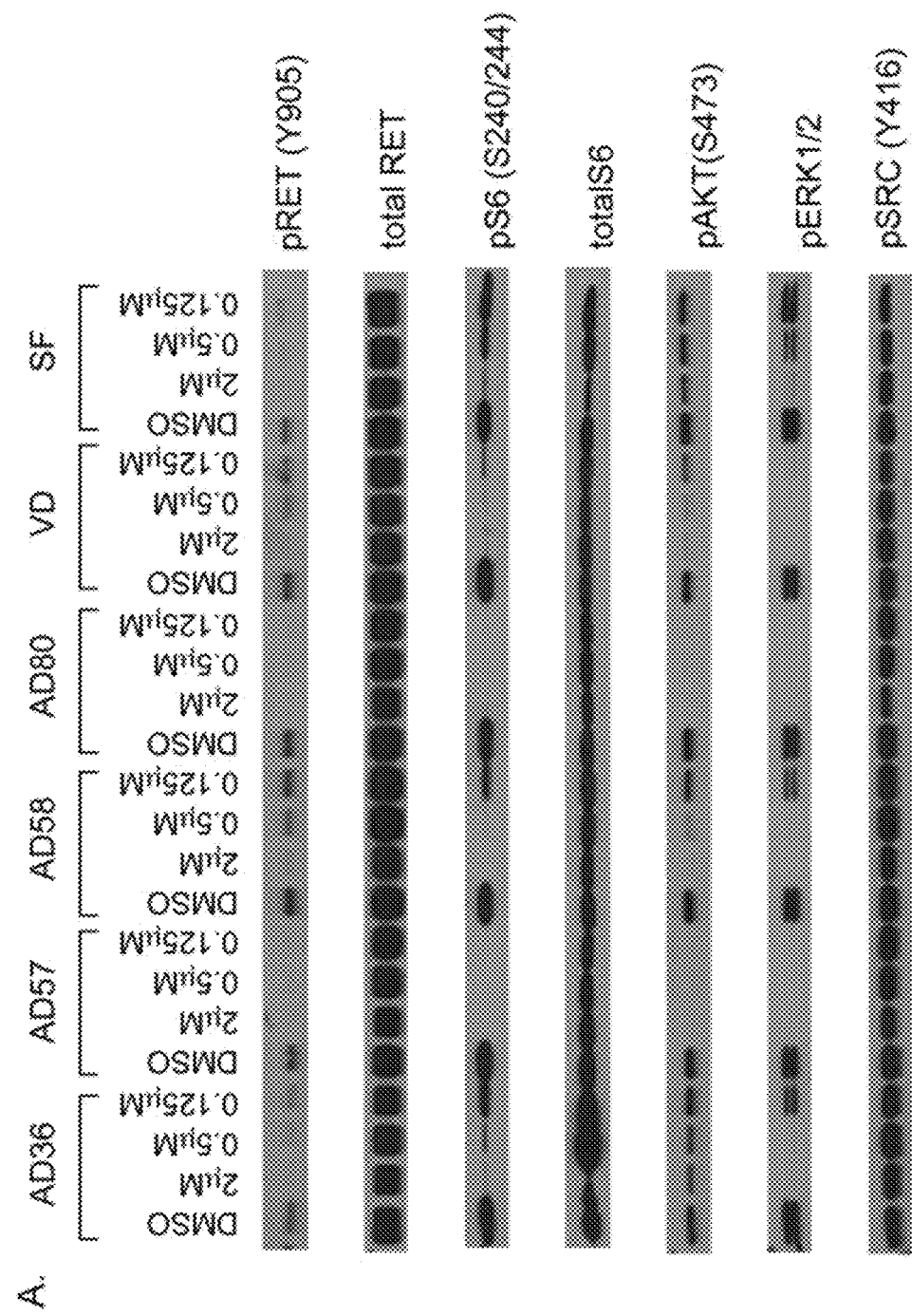
Figure 20B:
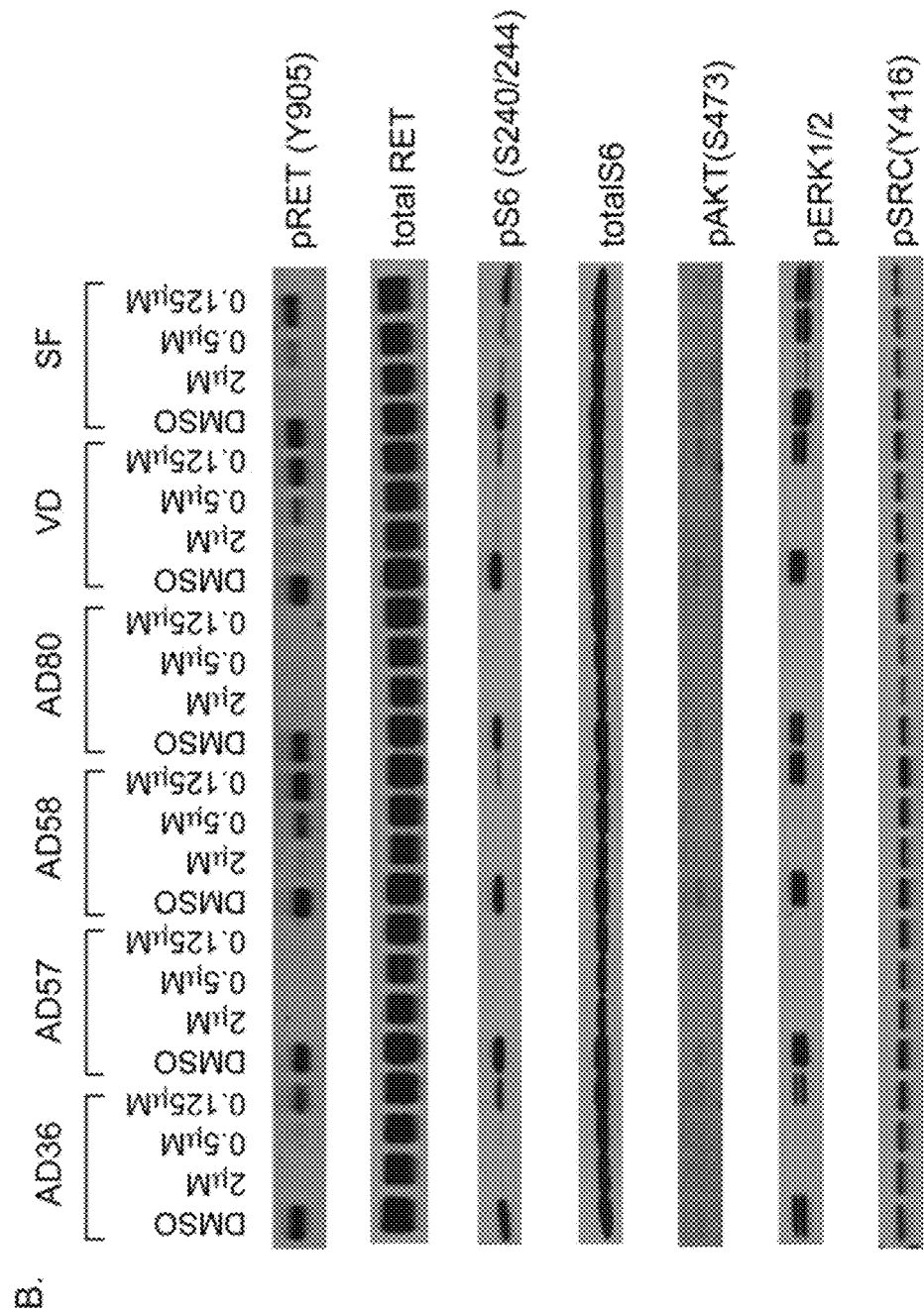

FIGS. 20. AD36, AD57, AD58, and AD80 are potent inhibitors within RET-driven cancer cell lines. A. MEN2B (MZ) and B. MEN2A (TT) thyroid cancer cells were treated with the indicated concentrations of drug. Following 1 hour of treatment, cells were harvested and lysates prepared for immunoblotting to detect the indicated proteins. VD=vandetanib; SF=sorafenib.

Figure 21:
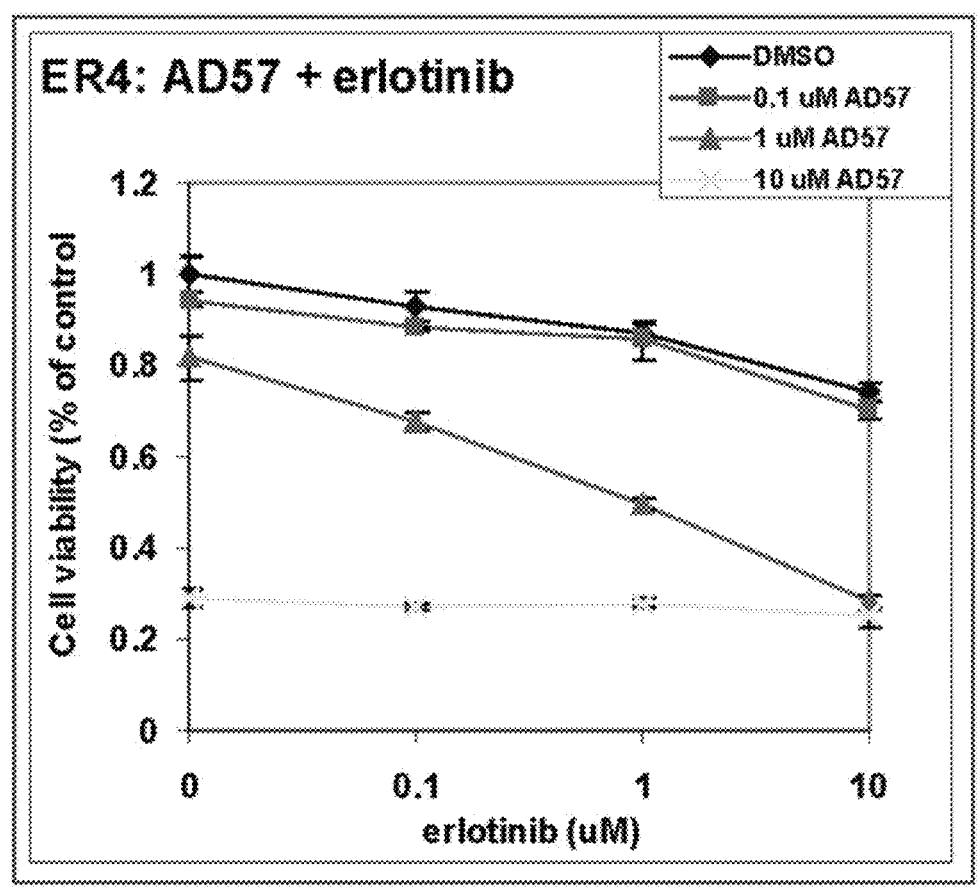
Figure 21:
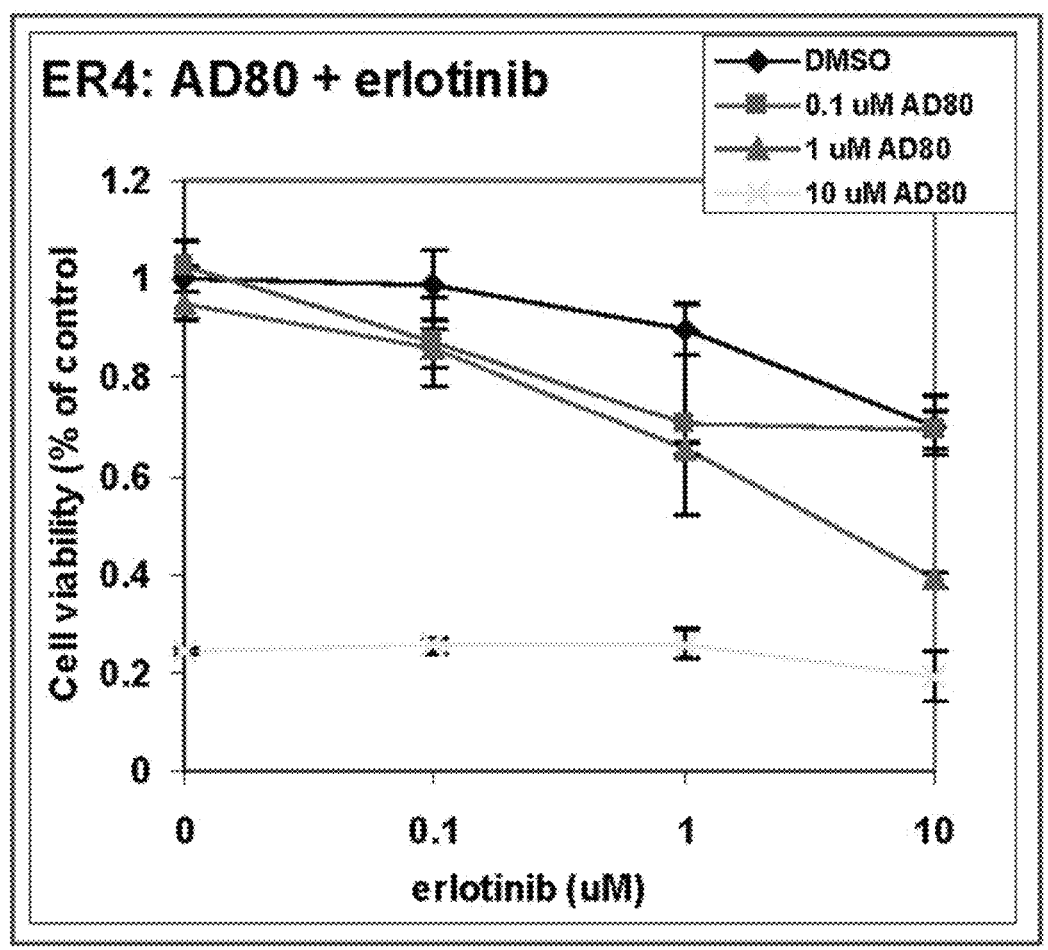

FIG. 21. Overcoming acquired resistance through AXL inhibitor treatment. Erlotinib plus AD57, AD80, or AD81 in ER4 cells (ER4 subline of HCC827 cells that are resistant to erlotinib treatment). Legend: diamond symbols are DMSO control, square symbols are 0.1 micromolar of compound, triangle symbols are 1 micromolar of compound, x symbol are 10 micromolar of compound, all in combination with erlotinib. AD57 and AD80 confer dose-dependent sensitivity to erlotinib in ER4 cells.

Figure 22:
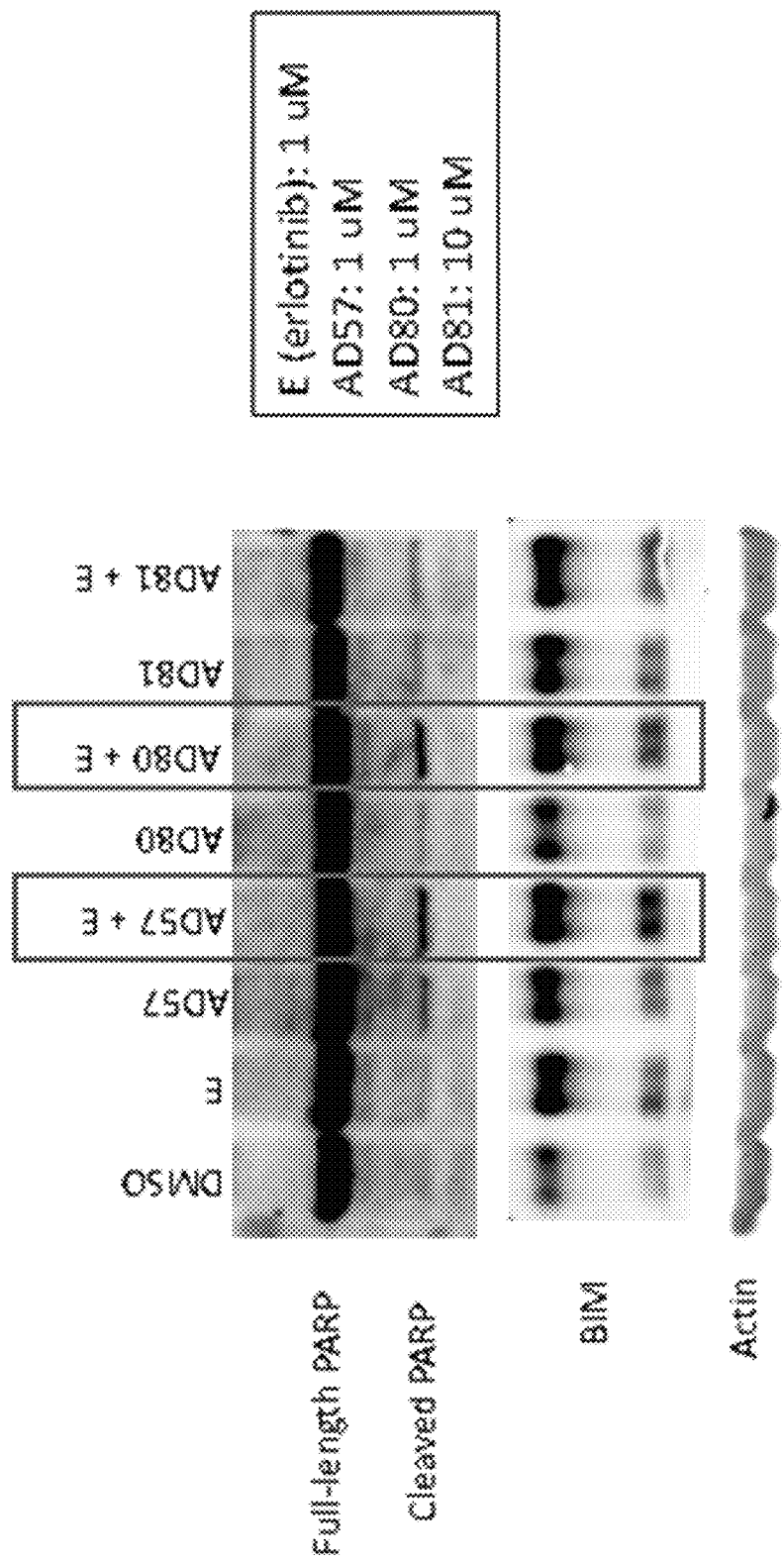

FIG. 22. Induction of apoptosis by combined EGFR and AXL inhibition. ER4 cells (ER4 subline of HCC827 cells that are resistant to erlotinib treatment) plated at $0.5 \times 10^6$ cells/condition. 24-hour drug exposure. Apoptosis measured by induction of PARP cleavage and BIM induction. E is erlotinib, AD57 at 1 micromolar, AD80 at 1 micromolar, AD81 at 10 micromolar. 24 hour exposure to AD57 or AD80 combined with erlotinib enhances apoptosis in ER4 cells.

Figure 23:
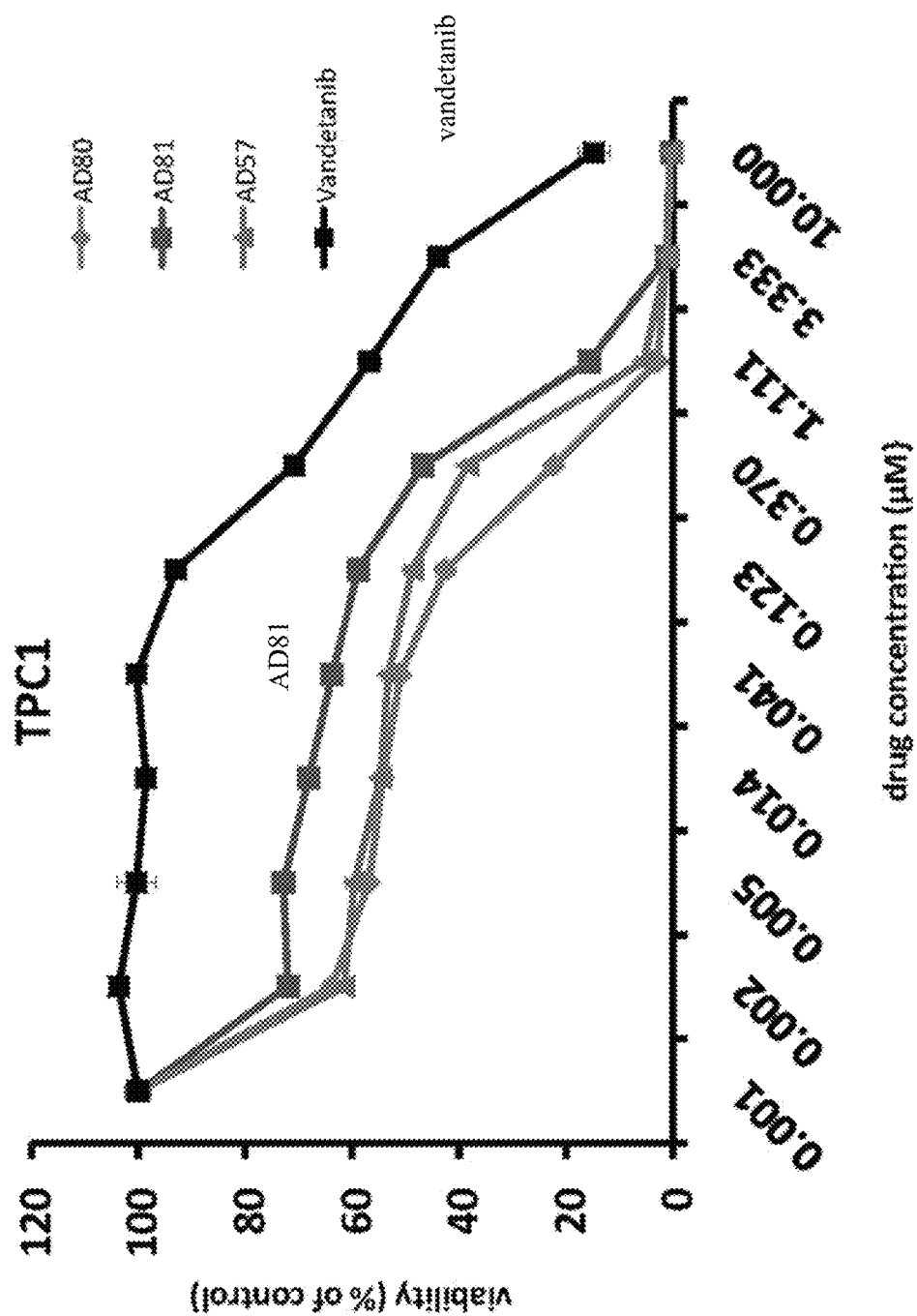

FIG. 23. CellTiterGlo-based proliferation assay measuring ATP content of cells after 96 h treatment with indicated compounds. TPC1 cells were plated at 1000 cells/well in 96 well plates and grown in growth media supplemented with 10% FBS. TPC1 cells are patient-derived thyroid cancer cells expressing the RET fusion protein CCDC6-RET. The IC50-values for AD80, AD81 and AD57 are in the range of 0.1-0.5 μM. AD80 diamonds, AD81 gray squares, AD57 triangles, vandetanib black squares.

Figure 24:
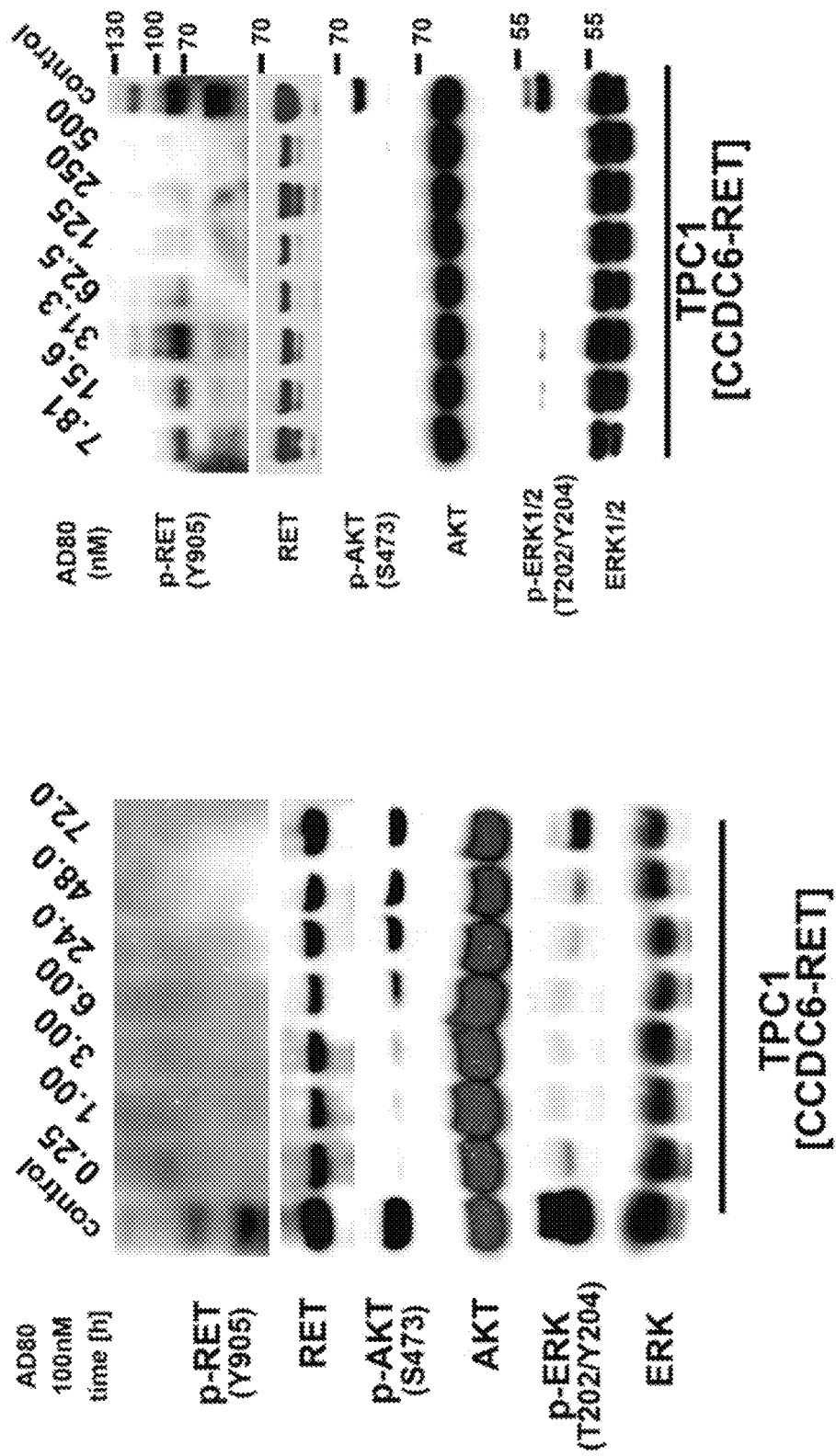

FIG. 24. Whole cell lysates of TPC1 cells were extracted after treatment with AD80 at indicated concentrations and given time points. TPC1 cells were grown in 6 cm dishes at 70-80% confluence in growth media supplemented with 10% FBS. AD80 treatment leads to dephosphorylation of the RET fusion protein at low nanomolar concentrations <10 nM. The inhibition of RET results in dephosphorylation of downstream signaling (PI3K, MAPK).

Figure 25:
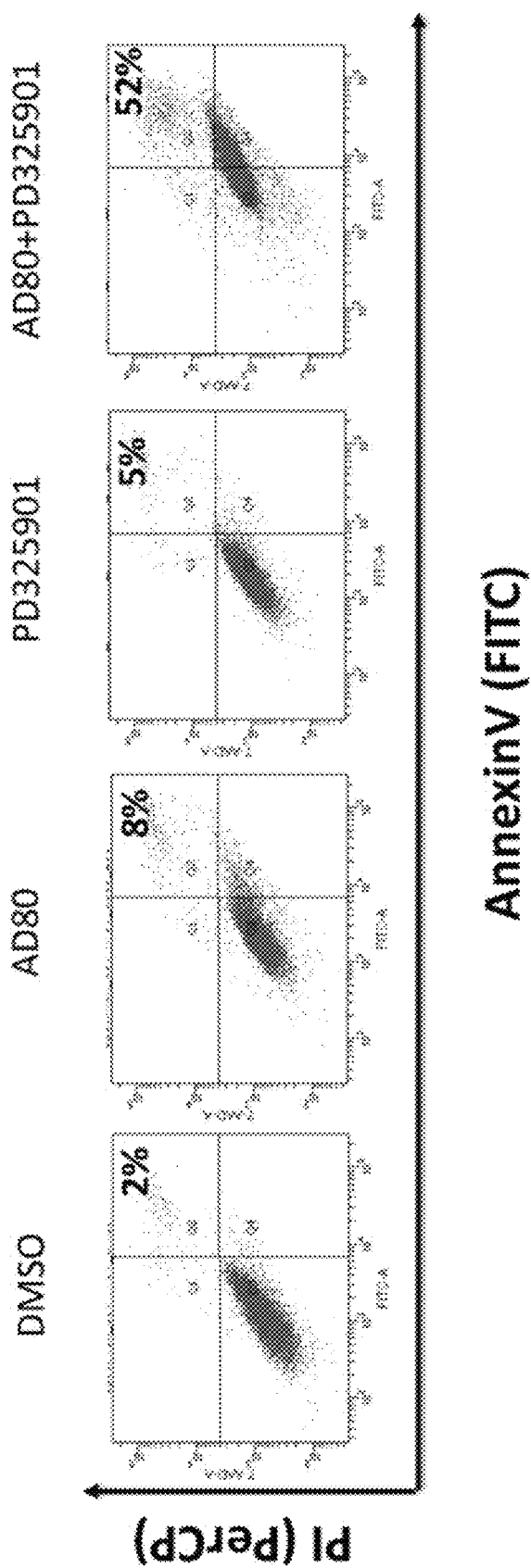

FIG. 25. TPC1 cells were grown in 6 well dishes at 70-80% confluence in growth media supplemented with 10% FBS. TPC1 cells were treated with either AD80, the MEK inhibitor PD325901 or a combination of both inhibitors at indicated concentrations for 72 h. Induction of apoptosis was measured using flow cytometry based counting of AnnexinV/PI positive cells. AD80 treatment alone does not lead to induction of apoptosis but a combination of AD80 and the MEK inhibitor PD325901 leads to robust induction of apoptosis.

DETAILED DESCRIPTION OF THE INVENTION

A. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —$S(O_2)$—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2R'$, —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

A heteroaryl group substituent may be a —O$^-$ bonded to a ring heteroatom nitrogen.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) —OH, —SH, —CN, —CF$_3$, —NO$_2$, oxo, —COOH, —CONH$_2$, —NO, —C(O)H, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, —COOH, —CONH$_2$, —NO, —C(O)H, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, —COOH, —CONH$_2$, —NO, —C(O)H, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, —COOH, —CONH$_2$, —NO, —C(O)H, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl, and each substituted or unsubstituted aryl is a substituted or unsubstituted 6 to 14 membered aryl (e.g. 6 membered aryl), and each substituted or unsubstituted heteroaryl is a substituted or unsubstituted 5 to 14 membered heteroaryl (e.g. 5 or 6 membered heteroaryl).

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl, and each substituted or unsubstituted aryl is a substituted or unsubstituted 6 to 10 membered aryl (e.g. 6 membered aryl), and each substituted or unsubstituted heteroaryl is a substituted or unsubstituted 5 to 10 membered heteroaryl (e.g. 5 or 6 membered heteroaryl).

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl, and/or each substituted or unsubstituted aryl is a substituted or unsubstituted 6 to 14 membered aryl (e.g. 6 membered aryl), and/or each substituted or unsubstituted heteroaryl is a substituted or unsubstituted 5 to 14 membered heteroaryl (e.g. 5 or 6 membered heteroaryl). In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene, and/or each substituted or unsubstituted arylene is a substituted or unsubstituted 6 to 14 membered arylene (e.g. 6 membered arylene), and/or each substituted or unsubstituted heteroarylene is a substituted or unsubstituted 5 to 14 membered heteroarylene (e.g. 5 or 6 membered heteroarylene).

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl, and/or each substituted or unsubstituted aryl is a substituted or unsubstituted 6 to 10 membered aryl (e.g. 6 membered aryl), and/or each substituted or unsubstituted heteroaryl is a substituted or unsubstituted 5 to 10 membered heteroaryl (e.g. 5 or 6 membered heteroaryl). In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene, and/or each substituted or unsubstituted aryl is a substituted or unsubstituted 6 to 10 membered arylene (e.g. 6 membered arylene), and/or each substituted or unsubstituted heteroaryl is a substituted or unsubstituted 5 to 10 membered heteroarylene (e.g. 5 or 6 membered heteroarylene). In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:

1520-1522 (1996) and U.S. Pat. No. 5,593,853). The methods above may be used to synthesize single molecular species.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. The term "treating," and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, reduce one or more symptoms of a disease or condition, reduce kinase activity in a cell, reduce the activity of RET, Raf, Src, and S6K kinase in a cell, reduce the activity of RET, Raf, Src, and S6K, but not mTOR in a cell, reduce the activity, levels or function of AXL, reduce the activity, levels or function of GAS6). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of a composition (e.g. antagonist) required to decrease the activity of an enzyme relative to the absence of the composition (e.g. antagonist). A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. kinase). In some embodiments, the protein may be RET kinase. In some embodiments, the protein may be Raf kinase. In some embodiments, the protein may be Src kinase. In some embodiments, the protein may be S6K kinase. In some embodiments, the protein may be AXL kinase. In some embodiments, the protein may be GAS6. In some embodiments contacting includes allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g. decreasing) the activity or function of the protein (e.g. decreasing the phosphorylation of another protein by a kinase) relative to the activity or function of the protein (e.g. kinase) in the absence of the inhibitor (e.g. kinase inhibitor or kinase inhibitor compound). In some embodiments inhibition refers to reduction of a disease or symptoms of disease. In some embodiments, inhibition refers to a reduction in the activity of a signal transduction pathway or signaling pathway (e.g. reduction of a pathway involving kinases, pathways involving Ret, Raf, Src, S6K, AXL, and/or GAS6). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. RET, Raf, Src, S6K, EGFR, MEK, AXL, and/or GAS6). In some embodiments, inhibition refers to inhibition of a kinase, such as Ret (e.g. NM_020630.4 or NP_065681.1), B-Raf (e.g. NM_004333.4 or NP_004324.2), Raf1 (e.g. NM 002880.3 or NP_002871.1), A-Raf (e.g. NM 001654.3 or NP 001645.1), Src (e.g. NM 005417.3 or NP_005408.1), S6K1, which may also be called S6K kinase (e.g. NM_003161.2 or NP 003152.1), S6K2 (e.g. NM_003952.2 or NP 003943.2), mTOR (NM_004958.3 or NP 004949.1), or AXL (NM_001699.4, AAH32229.1 or NP_001690.2). As used herein, the term "Raf" refers to a Raf kinase family member, including for example A-Raf, B-Raf, and/or C-Raf (aka Raf1). In some embodiments, the Raf is a human Raf kinase. In some embodiments, inhibition refers to inhibition of a protein-protein interaction (e.g. GAS6 binding to AXL). In some embodiments, inhibition refers to inhibition of a protein function (e.g. GAS6 (AAA58494.1) interactions with another protein or receptor binding).

The term "modulator" refers to a composition that increases or decreases the level of a target molecule or the function of a target molecule (e.g. a target may be a kinase and the function may be to phosphorylate a molecule). In some embodiments, a kinase modulator is a compound that reduces the activity of a kinase in a cell. A kinase modulator may reduce the activity of one kinase but cause an increase in enzyme activity of another kinase that results in a reduction or increase, respectively, of cell growth and proliferation. In some embodiments, a kinase disease modulator is a compound that reduces the severity of one or more symptoms of a disease associated with the kinase (e.g. cancer). A RET modulator is a compound that increases or decreases the activity or level of RET kinase. A Raf modulator is a compound that increases or decreases the activity or level of Raf kinase(s). A B-Raf modulator is a compound that increases or decreases the activity or level of B-Raf kinase. A Src modulator is a compound that increases or decreases the activity or level of Src kinase. A S6K modulator is a compound that increases or decreases the activity or level of S6K kinase. A MEN2 modulator is a compound that decreases the symptoms of multiple endocrine neoplasia 2. A S6K2 modulator is a compound that increases or decreases the activity or level of S6K2 kinase. An mTOR modulator is a compound that increases or decreases the activity level of mTOR kinase. An AXL modulator is a compound that increases or decreases the activity or level of AXL kinase. A GAS6 modulator is a compound that increases or decreases the level or function (e.g. activation or deactivation of a signaling pathway through binding to a receptor or interacting with another protein) of GAS6. An EGFR modulator is a compound that increases or decreases the activity or level of EGFR kinase. A MEK modulator is a compound that increases or decreases the activity or level of MEK kinase (e.g. MEK1, MEK2, MEK1 and MEK2).

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g. caused by) an activated or overactive kinase or aberrant kinase activity (e.g. multiple endocrine neoplasia 2, multiple endocrine neoplasia 2A, multiple endocrine neoplasia 2B, familial medullary thyroid cancer, medullary thyroid carcinoma, pheochromocytoma, primary hyperparathyroidism, intestinal ganglioneuromatosis, parathyroid hyperplasia, or mucosal neuromas). In some embodiments, the disease is a disease related to (e.g. caused by) an activated or overactive kinase (e.g. AXL) or aberrant kinase (e.g. AXL) activity (e.g. cancer, lung cancer, non-small cell lung cancer, erlotinib resistant cancer, erlotinib resistant lung cancer, erlotinib resistant non-small cell lung cancer, gefitinib resistant cancer, gefitinib resistant lung cancer, gefitinib resistant non-small cell lung cancer, breast cancer, pancreatic cancer, metastatic non-small cell lung cancer, metastatic pancreatic cancer, erlotinib resistant pancreatic cancer, chronic myelogenous leukemia, glioblastoma, melanoma, osteosarcoma, erythroid and megakaryocytic leukemias, uterine cancer, colon cancer, prostate cancer, thyroid cancer, ovarian cancer, liver cancer, gastrointestinal stromal tumors, renal cell carcinoma, acute myeloid leukemia, or gastric cancer). In some embodiments, the disease is a disease related to (e.g. caused by) an activated or overactive kinase (e.g. AXL) or aberrant kinase (e.g. AXL) activity (e.g. cancer, lung cancer, non-small cell lung cancer, erlotinib resistant cancer, erlotinib resistant lung cancer, erlotinib resistant non-small cell lung cancer, gefitinib resistant cancer, gefitinib resistant lung cancer, gefitinib resistant non-small cell lung cancer, breast cancer, pancreatic cancer, metastatic non-small cell lung cancer, metastatic pancreatic cancer, or erlotinib resistant pancreatic cancer. Examples of diseases, disorders, or conditions include, but are not limited to, multiple endocrine neoplasia 2, multiple endocrine neoplasia 2A, multiple endocrine neoplasia 2B, familial medullary thyroid cancer (also known as familial medullary thyroid carcinoma), medullary thyroid carcinoma, pheochromocytoma, primary hyperparathyroidism, intestinal ganglioneuromatosis, parathyroid hyperplasia, mucosal neuromas, melanoma, colorectal cancer, papillary thyroid cancer, breast cancer, hepatocellular carcinoma, lung cancer, Alzheimer's disease, Parkinson's disease, Huntington's Disease, frontotemporal dementia, Bovine spongiform encephalopathy (BSE), Creutzfeldt-Jakob disease, Gerstmann-Sträussler-Scheinker syndrome, kuru, prion disease, neurodegenerative diseases, frontotemporal dementia, cancer, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, migraine headaches, stroke, aneurysm, brain aneurysm, cerebral aneurysm, brain attack, cerebrovascular accident, ischemia, thrombosis, arterial embolism, hemorrhage, transient ischemic attack, anemia, embolism, systemic hypoperfusion, venous thrombosis, arthritis, reperfusion injury, skin diseases or conditions, acne, acne vulgaris, keratosis pilaris, acute, promyelocytic leukemia, baldness, acne rosacea, harlequin ichthyosis, xeroderma pigmentosum, keratoses, neuroblastoma, fibrodysplasia ossificans progressive, eczema, rosacea, sun damage, wrinkles, or cosmetic conditions. In some instances, "disease" or "condition" refer to cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff s disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

As used herein, the term "autoimmune disease" refers to a disease or condition in which a subject's immune system irregularly responds to one or more components (e.g. biomolecule, protein, cell, tissue, organ, etc.) of the subject. In some embodiments, an autoimmune disease is a condition in which the subject's immune system irregularly reacts to one or more components of the subject as if such components were not self. Exemplary autoimmune diseases that may be treated with a compound or method provided herein include Acute Disseminated Encephalomyelitis (ADEM), Acute necrotizing hemorrhagic leukoencephalitis, Addison's disease, Agammaglobulinemia, Asthma, Allergic asthma, Allergic rhinitis, Alopecia areata, Amyloidosis, Ankylosing spondylitis, Anti-GBM/Anti-TBM nephritis, Antiphospholipid syndrome (APS), Arthritis, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Axonal & neuronal neuropathies, Balo disease, Behcet's disease, Bullous pemphigoid, Cardiomyopathy, Castleman disease, Celiac sprue, Chagas disease, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic fasciitis, Erythema nodosum, Experimental allergic encephalomyelitis, Evans syndrome, Fibrosing alveolitis, Giant cell arteritis (temporal arteritis), Glomerulonephritis, Goodpasture's syndrome, Graves' disease, Grave's ophthalmopathy, Guillain-Barre syndrome, Hashimoto's encephalitis, Hashimoto's thyroiditis, Hemolytic anemia, Henoch-Schonlein purpura, Herpes gestationis, Hypogammaglobulinemia, Ichthyosis, Idiopathic thrombocytopenic purpura (ITP), IgA nephropathy, IgG4-related sclerosing disease, Immunoregulatory lipoproteins, Inclusion body myositis, Inflammatory bowel disease, Insulin-dependent diabetes (type1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic, arthritis, Idiopathic pulmonary fibrosis, Pyoderma gangrenous, Pure red cell aplasia, Raynauds phenomenon, Reflex sympathetic dystrophy, Reiter's syndrome, Relapsing polychondritis, Restless legs syndrome, Retroperitoneal Fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, or Wegener's granulomatosis.

As used herein, the term "inflammatory disease" refers to any disease characterized by abnormal inflammation. Exemplary inflammatory diseases that may be treated with a compound or method provided herein include arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, or allergic asthma.

As used herein, the term "cardiovascular disease" refers to a disease or condition affecting the heart or blood vessels. In embodiments, cardiovascular disease includes diseases caused by or exacerbated by atherosclerosis. Exemplary cardiovascular diseases that may be treated with a compound or method provided herein include Alcoholic cardiomyopathy, Coronary artery disease, Congenital heart disease, Arrhythmogenic right ventricular cardiomyopathy, Restrictive cardiomyopathy, Noncompaction Cardiomyopathy, diabetes mellitus, hypertension, hyperhomocysteinemia, hypercholesterolemia, Atherosclerosis, Ischemic heart disease, Heart failure, Cor pulmonale, Hypertensive heart disease, Left ventricular hypertrophy, Coronary heart disease, (Congestive) heart failure, Hypertensive cardiomyopathy, Cardiac arrhythmias, Inflammatory heart disease, Endocarditis, Inflammatory cardiomegaly, Myocarditis, Valvular heart disease, stroke, or myocardial infarction. In some embodiments, treating a cardiovascular disease includes treating a condition or symptom caused by a cardiovascular disease. A non-limiting example of such a treatment is treating complications due to a myocardial infarction, after the myocardial infarction has occurred.

As used herein, the term "cancer" refers to all types of cancer, neoplasm or malignant tumors found in mammals, including leukemia, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, pancreas, sarcoma, stomach, uterus or Medulloblastoma. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

"MEN2 associated cancer" (also referred to herein as "MEN2 related cancer") refers to a cancer caused by a MEN2 syndrome. MEN2A and MEN2B are subtypes of MEN2, which are well known in the art. A "cancer associated with aberrant Ret activity" (also referred to herein as "Ret related cancer") is a cancer caused by aberrant Ret activity (e.g. a mutated Ret gene, Ret fusion for example CCDC6-RET fusion or KIF5B-RET fusion). Ret related cancers may include medullary thyroid carcinoma, pheochromocytoma, primary hyperparathyroidism, intestinal ganglioneuromatosis, parathyroid hyperplasia, or mucosal neuromas. A "cancer associated with aberrant Raf activity" (also referred to herein as "Raf related cancer") is a cancer caused by aberrant Raf activity (e.g. a mutated Raf gene or aberrant amount of Raf protein). A "cancer associated with aberrant B-Raf activity" (also referred to herein as "B-Raf related cancer") is a cancer caused by aberrant B-Raf activity (e.g. a mutated B-Raf gene or aberrant amount of B-Raf protein). Raf related cancers may include lung cancer, melanoma, colorectal cancer, or papillary thyroid cancer. A "cancer associated with aberrant Src activity" (also referred to herein as "Src related cancer") is a cancer caused by aberrant Src activity (e.g. a mutated Src gene). Src related cancers may include breast cancer. A "cancer associated with aberrant S6K kinase activity" (also referred to herein as "S6K kinase related cancer") is a cancer caused by aberrant S6K kinase activity (e.g. a mutated S6K gene). S6K kinase related cancers may include hepatocellular carcinoma or lung cancer. A "cancer associated with aberrant AXL kinase activity" (also referred to herein as "AXL kinase related cancer") is a cancer caused by aberrant AXL kinase activity (e.g. a mutated AXL gene or aberrant amount of AXL protein or aberrant amount of AXL protein ligand such as GAS6). AXL kinase related cancers may include lung cancer, non-small cell lung cancer, EGFR-targeted therapy or therapeutic resistant cancer (e.g. lung cancer, non-small cell lung cancer), erlotinib resistant lung cancer, gefitinib resistant lung cancer, pancreatic cancer, metastatic cancer, chronic myelogenous leukemia, glioblastoma, melanoma, osteosarcoma, erythroid and megakaryocytic leukemias, uterine cancer, colon cancer, prostate cancer, thyroid cancer, ovarian cancer, liver cancer, gastrointestinal stromal tumors, renal cell carcinoma, acute myeloid leukemia, gastric cancer, or breast cancer. A "cancer associated with aberrant Raf kinase activity and S6K kinase activity" (also referred to herein as "Raf and S6K kinase related cancer") is a cancer caused by aberrant Raf kinase activity and aberrant S6K kinase activity. A "cancer associated with aberrant B-Raf kinase activity and S6K kinase activity" (also referred to herein as "B-Raf and S6K kinase related cancer") is a cancer caused by aberrant B-Raf kinase activity and aberrant S6K kinase activity. Raf and S6K kinase related cancer may include lung cancer. A "cancer associated with aberrant S6K2 kinase activity" (also referred to herein as "S6K2 kinase related cancer") is a cancer caused by aberrant S6K2 kinase activity (e.g. a mutated S6K2 gene). Other cancers that are associated with aberrant activity of one or more of Ret, Raf, B-Raf, Src, S6K, AXL, or mTOR kinase are well known in the art and determining such cancers are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, parenteral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation, anti-cancer agents). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a kinase inhibitor" means administering a compound that inhibits the activity or level (e.g. amount) of one or more kinase(s) (e.g. a Ret kinase inhibitor, Raf kinase inhibitor, B-Raf kinase inhibitor Src kinase inhibitor, S6K kinase inhibitor, mTOR kinase inhibitor, S6K2 kinase inhibitor, AXL kinase inhibitor, or a multi-kinase inhibitor such as a Ret/Raf/Src/S6K kinase inhibitor or a Ret/Raf/Src/S6K/mTOR kinase inhibitor or a Ret/B-Raf/Src/S6K kinase inhibitor) to a subject and, without being limited by mechanism, allowing sufficient time for the kinase inhibitor to reduce the activity of one or more kinase(s) or for the kinase inhibitor to reduce one or more symptoms of a disease (e.g. cancer, wherein the kinase inhibitor may arrest the cell cycle, slow the cell cycle, reduce DNA replication, reduce cell replication, reduce cell growth, reduce metastasis, overcome resistance to a separate treatment or compound (e.g. an anti-cancer agent, EGFR-targeted therapy, erlotinib, gefitinib, induce or increase apoptosis, or cause cell death).

The term "associated" or "associated with" as used herein to describe a disease (e.g. a protein associated disease, a cancer associated with aberrant Ret activity, Raf associated cancer, B-Raf associated cancer, Src associated cancer, S6K kinase associated cancer, S6K2 kinase associated cancer, AXL kinase associated cancer, EGFR associated cancer or disease, MEK associated cancer or disease) means that the disease (e.g. cancer) is caused by, or a symptom of the disease is caused by, what is described as disease associated or what is described as associated with the disease. For example, a cancer associated with aberrant Ret activity may be a cancer that results (entirely or partially) from aberrant Ret kinase activity or a cancer wherein a particular symptom of the disease is caused (entirely or partially) by aberrant Ret activity. As used herein, what is described as being associated with a disease, if a causative agent, could be a target for treatment of the disease. For example, a cancer associated with aberrant Ret activity or a Ret associated cancer, may be treated with a Ret modulator or Ret inhibitor, in the instance where increased Ret activity causes the cancer. For example, a cancer associated with MEN2 may be a cancer that a subject with MEN2 is at higher risk of developing as compared to a subject without MEN2.

The tem "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer (e.g. lung cancer, non-small cell lung cancer, breast cancer, pancreatic cancer, a MEN2 associated cancer, an AXL kinase associated cancer). In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate;

melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739(Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"EGFR-targeted therapy" or "EGFR-targeted therapeutic" is used in accordance with its plain ordinary meaning and refers to a composition (e.g. compound, protein, nucleic acid, antibody, small molecule) useful in treating a disease, wherein the compound modulates the activity, level, or function of EGFR. In some embodiments, the composition contacts EGFR. In some embodiments, the composition preferentially binds EGFR. In some embodiments, the composition specifically binds EGFR. In some embodiments, the composition is an EGFR modulator. In some embodiments, the composition is an EGFR inhibitor. In some embodiments, the disease is an EGFR associated disease. In some embodiments, the composition is selected from the group consisting of gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, and BMS-599626. In some embodiments, the composition is selected from the group consisting of gefitinib (Iressa™), erlotinib (Tarceva™), cetuximab (Erbitux™), lapatinib (Tykerb™), panitumumab (Vectibix™), vandetanib (Caprelsa™). In some embodiments, the composition is gefitinib (Iressa™). In some embodiments, the composition is erlotinib (Tarceva™). In some embodiments, the composition is cetuximab (Erbitux™). In some embodiments, the composition is lapatinib (Tykerb™), panitumumab (Vectibix™). In some embodiments, the composition is vandetanib (Caprelsa™).

"MEK-targeted therapy" or "MEK-targeted therapeutic" is used in accordance with its plain ordinary meaning and refers to a composition (e.g. compound, protein, nucleic acid, antibody, small molecule) useful in treating a disease, wherein the compound modulates the activity, level, or function of MEK. In some embodiments, the composition contacts MEK. In some embodiments, the composition preferentially binds MEK. In some embodiments, the composition specifically binds MEK. In some embodiments, the composition is an MEK modulator. In some embodiments, the composition is an MEK inhibitor. In some embodiments, the disease is a MEK associated disease. In some embodiments, a MEK-targeted therapy modulates the activity, level, or function of MEK1. In some embodiments, a MEK-targeted therapy modulates the activity, level, or function of MEK2. In some embodiments, a MEK-targeted therapy modulates the activity, level, or function of MEK1 and MEK2. In some embodiments, a MEK inhibitor includes a composition selected from the group consisting of XL518, CI-1040, PD035901, selumetinib/AZD6244, GSK1120212/trametinib, GDC-0973, ARRY-162, ARRY-300, AZD8330, PD0325901/PD325901, U0126, PD98059, TAK-733, PD318088, AS703026, and BAY 869766. In some embodiments, the composition is selumetinib/AZD6244.

B. Compounds

In a first aspect is a compound having the formula:

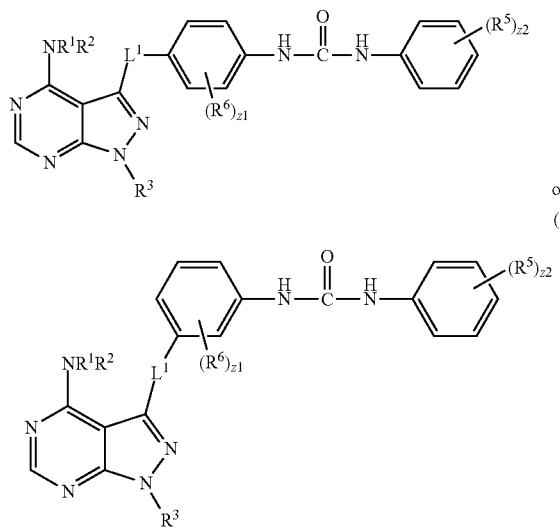

$R^1$ and $R^2$ are independently hydrogen or substituted or unsubstituted alkyl. $R^3$ is independently substituted or unsubstituted alkyl. $R^5$ is independently hydrogen, halogen, —$CX^a_3$, —CN, —OH, —COOH, —$CONH_2$, —NO, —$NO_2$, —C(O)H, —SH, —$SO_2Cl$, —$SO_3H$, —$SO_4H$, —$SO_2NH_2$, —$NHNH_2$, —$ONH_2$, —NHC═(O)$NHNH_2$, —C(O)$CH_3$, —NHC═(O)$NH_2$, —$NHSO_2H$, —NHC═(O)H, —NHC(O)—OH, —NHOH, —$OCF_3$, —$OCHF_2$, or substituted or unsubstituted alkyl. $R^6$ is independently hydrogen, halogen, —$CX^b_3$, —CN, —OH, —COOH, —$CONH_2$, —NO, —$NO_2$, —C(O)H, —SH, —$SO_2Cl$, —$SO_3H$, —$SO_4H$, —$SO_2NH_2$, —$NHNH_2$, —$ONH_2$, —NHC═(O)$NHNH_2$, —C(O)$CH_3$, —NHC═(O)$NH_2$, —$NHSO_2H$, —NHC═(O)H, —NHC(O)—OH, —NHOH, —$OCF_3$, or —$OCHF_2$. $L^1$ is independently a bond or substituted or unsubstituted alkylene. The symbol z1 is independently an integer from 0 to 4. The symbol z2 is independently an integer from 0 to 5. The symbols $X^a$ and $X^b$ are independently —F, —Cl, —Br, or —I.

In some embodiments of a compound having formula (I) or (II), the compound has a formula:

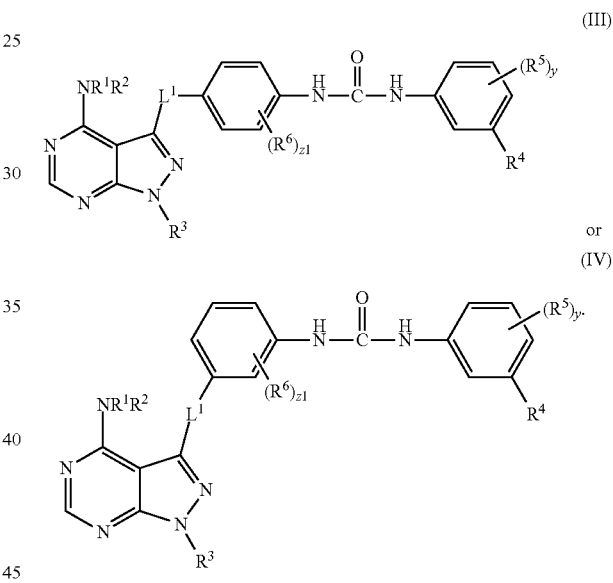

In a compound of formula (III) or (IV), $R^1$, $R^2$, $R^3$, $R^5$, $R^6$, $L^1$, z1, $X^a$, and $X^b$ are as described herein, including embodiments (e.g. formula (I) or (II) or any embodiments). $R^4$ is independently hydrogen, halogen, —$CX_3$, —CN, —OH, —COOH, —$CONH_2$, —NO, —$NO_2$, —C(O)H, —SH, —$SO_2Cl$, —$SO_3H$, —$SO_4H$, —$SO_2NH_2$, —$ONH_2$, —NHC═(O)$NHNH_2$, —C(O)$CH_3$, —NHC═(O)$NH_2$, —$NHSO_2H$, —NHC═(O)H, —NHC(O)—OH, —NHOH, —$OCF_3$, —$OCHF_2$, or substituted or unsubstituted alkyl. The symbol y is independently an integer from 0 to 4. The symbol X is independently —F, —Cl, —Br, or —I.

In some embodiments of the compound having formula (I), (II), (III), or (IV), $R^1$ is hydrogen. In some embodiments, $R^1$ is substituted or unsubstituted alkyl. In some embodiments, le is unsubstituted alkyl. In some embodiments, $R^1$ is unsubstituted ($C_1$-$C_6$) alkyl. In some embodiments, $R^1$ is unsubstituted ($C_1$-$C_4$) alkyl. In some embodiments, $R^1$ is methyl. In some embodiments, $R^1$ is ethyl. In some embodiments, $R^1$ is n-propyl. In some embodiments, $R^1$ is isopropyl. In some embodiments, $R^1$ is n-butyl. In some embodiments, $R^1$ is t-butyl. In some embodiments, $R^1$ is n-pentyl.

In some embodiments, $R^1$ is substituted alkyl. In some embodiments, $R^1$ is substituted ($C_1$-$C_6$) alkyl. In some embodiments, $R^1$ is substituted ($C_1$-$C_4$) alkyl.

In some embodiments of the compound having formula (I), (II), (III), or (IV), $R^2$ is hydrogen. In some embodiments, $R^2$ is substituted or unsubstituted alkyl. In some embodiments, $R^2$ is unsubstituted alkyl. In some embodiments, $R^2$ is unsubstituted ($C_1$-$C_6$) alkyl. In some embodiments, $R^2$ is unsubstituted ($C_1$-$C_4$) alkyl. In some embodiments, $R^2$ is methyl. In some embodiments, $R^1$ is ethyl. In some embodiments, $R^2$ is n-propyl. In some embodiments, $R^2$ is isopropyl. In some embodiments, $R^2$ is n-butyl. In some embodiments, $R^2$ is t-butyl. In some embodiments, $R^2$ is n-pentyl. In some embodiments, $R^2$ is substituted alkyl. In some embodiments, $R^2$ is substituted ($C_1$-$C_6$) alkyl. In some embodiments, $R^2$ is substituted ($C_1$-$C_4$) alkyl.

In some embodiments of the compound having formula (I), (II), (III), or (IV), $L^1$ is a bond. In some embodiments, $L^1$ is substituted or unsubstituted alkylene. In some embodiments, $L^1$ is unsubstituted alkylene. In some embodiments, $L^1$ is unsubstituted ($C_1$-$C_6$) alkylene. In some embodiments, $L^1$ is unsubstituted ($C_1$-$C_4$) alkylene. In some embodiments, $L^1$ is methylene. In some embodiments, $L^1$ is ethylene. In some embodiments, $L^1$ is n-propylene. In some embodiments, $L^1$ is isopropylene. In some embodiments, $L^1$ is n-butylene. In some embodiments, $L^1$ is t-butylene. In some embodiments, $L^1$ is n-pentylene. In some embodiments, $L^1$ is substituted alkylene. In some embodiments, $L^1$ is substituted ($C_1$-$C_6$) alkylene. In some embodiments, $L^1$ is substituted ($C_1$-$C_4$) alkylene.

In some embodiments of the compound having formula (I), (II), (III), or (IV), $R^3$ is substituted or unsubstituted alkyl. In some embodiments, $R^3$ is unsubstituted alkyl. In some embodiments, $R^3$ is unsubstituted ($C_1$-$C_6$) alkyl. In some embodiments, $R^3$ is unsubstituted ($C_1$-$C_4$) alkyl. In some embodiments, $R^3$ is methyl. In some embodiments, $R^3$ is ethyl. In some embodiments, $R^3$ is n-propyl. In some embodiments, $R^3$ is isopropyl. In some embodiments, $R^3$ is n-butyl. In some embodiments, $R^3$ is t-butyl. In some embodiments, $R^3$ is n-pentyl. In some embodiments, $R^3$ is substituted alkyl. In some embodiments, $R^3$ is substituted ($C_1$-$C_6$) alkyl. In some embodiments, $R^3$ is substituted ($C_1$-$C_4$) alkyl.

In some embodiments of the compound having formula (III), or (IV), $R^4$ is independently hydrogen, halogen, $-CX_3$, $-CN$, $-OH$, $-COOH$, $-CONH_2$, $-NO$, $-NO_2$, $-C(O)H$, $-SH$, $-SO_2Cl$, $-SO_3H$, $-SO_4H$, $-SO_2NH_2$, $-NHNH_2$, $-ONH_2$, $-NHC=(O)NHNH_2$, $-C(O)CH_3$, $-NHC=(O)NH_2$, $-NHSO_2H$, $-NHC=(O)H$, $-NHC(O)-OH$, $-NHOH$, $-OCF_3$, $-OCHF_2$, or substituted or unsubstituted alkyl. In some embodiments, $R^4$ is independently halogen, $-CN$, $-CX_3$, $-NO$, $-NO_2$, $-C(O)H$, or $-CO_2H$. In some embodiments, $R^4$ is halogen. In some embodiments, $R^4$ is $-CN$. In some embodiments, $R^4$ is $-NO$. In some embodiments, $R^4$ is $-NO_2$. In some embodiments, $R^4$ is $-C(O)H$. In some embodiments, $R^4$ is $-CO_2H$. In some embodiments, $R^4$ is halogen or $-CX_3$. In some embodiments, $R^4$ is $-CX_3$. In some embodiments, X is $-F$. In some embodiments, X is $-Cl$. In some embodiments, X is $-Br$. In some embodiments, X is $-I$. In some embodiments, $R^4$ is $-F$. In some embodiments, $R^4$ is $-Cl$. In some embodiments, $R^4$ is $-Br$. In some embodiments, $R^4$ is $-I$. In some embodiments, $R^4$ is substituted or unsubstituted alkyl. In some embodiments, $R^4$ is unsubstituted alkyl. In some embodiments, $R^4$ is unsubstituted ($C_1$-$C_6$) alkyl. In some embodiments, $R^4$ is unsubstituted ($C_1$-$C_4$) alkyl. In some embodiments, $R^4$ is methyl. In some embodiments, $R^4$ is ethyl. In some embodiments, $R^4$ is n-propyl. In some embodiments, $R^4$ is isopropyl. In some embodiments, $R^4$ is n-butyl. In some embodiments, $R^4$ is t-butyl. In some embodiments, $R^4$ is n-pentyl. In some embodiments, $R^4$ is substituted alkyl. In some embodiments, $R^4$ is substituted ($C_1$-$C_6$) alkyl. In some embodiments, $R^4$ is substituted ($C_1$-$C_4$) alkyl.

In some embodiments of the compound having formula (I), (II), (III), or (IV), $R^5$ is independently hydrogen, halogen, $-CX^a_3$, $-CN$, $-OH$, $-COOH$, $-CONH_2$, $-NO$, $-NO_2$, $-C(O)H$, $-SH$, $-SO_2Cl$, $-SO_3H$, $-SO_4H$, $-SO_2NH_2$, $-NHNH_2$, $-ONH_2$, $-NHC=(O)NHNH_2$, $-C(O)CH_3$, $-NHC=(O)NH_2$, $-NHSO_2H$, $-NHC=(O)H$, $-NHC(O)-OH$, $-NHOH$, $-OCF_3$, $-OCHF_2$, or substituted or unsubstituted alkyl. In some embodiments, $R^5$ is independently halogen, $-CN$, $-CX^a_3$, $-NO$, $-NO_2$, $-C(O)H$, or $-CO_2H$. In some embodiments, $R^5$ is halogen. In some embodiments, $R^5$ is $-CN$. In some embodiments, $R^5$ is $-NO$. In some embodiments, $R^5$ is $-NO_2$. In some embodiments, $R^5$ is $-C(O)H$. In some embodiments, $R^5$ is $-CO_2H$. In some embodiments, $R^5$ is halogen or $-CX^a_3$. In some embodiments, $R^5$ is $-CX^a_3$. In some embodiments, $X^a$ is $-F$ (i.e. $R^5$ is $-CF_3$). In some embodiments, $X^a$ is $-Cl$. In some embodiments, $X^a$ is $-Br$. In some embodiments, $X^a$ is $-I$. In some embodiments, $R^5$ is $-F$. In some embodiments, $R^5$ is $-Cl$. In some embodiments, $R^5$ is $-Br$. In some embodiments, $R^5$ is $-I$. In some embodiments, $R^5$ is substituted or unsubstituted alkyl. In some embodiments, $R^5$ is unsubstituted alkyl. In some embodiments, $R^5$ is unsubstituted ($C_1$-$C_6$) alkyl. In some embodiments, $R^5$ is unsubstituted ($C_1$-$C_4$) alkyl. In some embodiments, $R^5$ is methyl. In some embodiments, $R^5$ is ethyl. In some embodiments, $R^5$ is n-propyl. In some embodiments, $R^5$ is isopropyl. In some embodiments, $R^5$ is n-butyl. In some embodiments, $R^5$ is t-butyl. In some embodiments, $R^5$ is n-pentyl. In some embodiments, $R^5$ is substituted alkyl. In some embodiments, $R^5$ is substituted ($C_1$-$C_6$) alkyl. In some embodiments, $R^5$ is substituted ($C_1$-$C_4$) alkyl.

In some embodiments of the compound having formula (I), (II), (III), or (IV), $R^6$ is independently hydrogen, halogen, $-CX^b_3$, $-CN$, $-OH$, $-COOH$, $-CONH_2$, $-NO$, $-NO_2$, $-C(O)H$, $-SH$, $-SO_2Cl$, $-SO_3H$, $-SO_4H$, $-SO_2NH_2$, $-NHNH_2$, $-ONH_2$, $-NHC=(O)NHNH_2$, $-C(O)CH_3$, $-NHC=(O)NH_2$, $-NHSO_2H$, $-NHC=(O)H$, $-NHC(O)-OH$, $-NHOH$, $-OCF_3$, or $-OCHF_2$. In some embodiments, $R^6$ is halogen, $-CN$, $-CX^b_3$, $-NO$, $-NO_2$, $-C(O)H$, or $-CO_2H$. In some embodiments, $R^6$ is halogen. In some embodiments, $R^6$ is $-CN$. In some embodiments, $R^6$ is $-NO$. In some embodiments, $R^6$ is $-NO_2$. In some embodiments, $R^6$ is $-C(O)H$. In some embodiments, $R^6$ is $-CO_2H$. In some embodiments, $R^6$ is halogen or $-CX^b_3$. In some embodiments, $R^6$ is $-CX^b_3$. In some embodiments, $X^b$ is $-F$ (i.e. $R^6$ is $-CF_3$). In some embodiments, $X^b$ is $-Cl$. In some embodiments, $X^b$ is $-Br$. In some embodiments, $X^b$ is $-I$. In some embodiments, $R^6$ is $-F$. In some embodiments, $R^6$ is $-Cl$. In some embodiments, $R^6$ is $-Br$. In some embodiments, $R^6$ is $-I$.

In some embodiments of the compound having formula (I), (II), (III), or (IV), y is 1 to 4. In some embodiments, y is 1 to 3. In some embodiments, y is 1 to 2. In some embodiments, y is 0 to 4. In some embodiments, y is 0 to 3. In some embodiments, y is 0 to 2. In some embodiments, y is 0 to 1. In some embodiments, y is 0. In some embodiments, y is 1. In some embodiments, y is 2. In some embodiments, y is 3. In some embodiments, y is 4.

In some embodiments of the compound having formula (I), (II), (III), or (IV), z1 is 1 to 4. In some embodiments, z1 is 1 to 3. In some embodiments, z1 is 1 to 2. In some embodiments, z1 is 0 to 4. In some embodiments, z1 is 0 to 3. In some embodiments, z1 is 0 to 2. In some embodiments, z1 is 0 to 1. In some embodiments, z1 is 0. In some embodiments, z1 is 1. In some embodiments, z1 is 2. In some embodiments, z1 is 3. In some embodiments, z1 is 4.

In some embodiments of the compound having formula (I), (II), (III), or (IV), z2 is 1 to 5. In some embodiments, z2 is 1 to 4. In some embodiments, z2 is 1 to 3. In some embodiments, z2 is 1 to 2. In some embodiments, z2 is 0 to 5. In some embodiments, z2 is 0 to 4. In some embodiments, z2 is 0 to 3. In some embodiments, z2 is 0 to 2. In some embodiments, z2 is 0 to 1. In some embodiments, z2 is 0. In some embodiments, z2 is 1. In some embodiments, z2 is 2. In some embodiments, z2 is 3. In some embodiments, z2 is 4. In some embodiments, z2 is 5.

In some embodiments, where an alkyl or alkylene is substituted, the alkyl or alkylene is substituted with a substituent group. In other embodiments, where an alkyl or alkylene is substituted, the alkyl or alkylene is substituted with a size-limited substituent group. In other embodiments, where an alkyl or alkylene is substituted, the alkyl or alkylene is substituted with a lower substituent group. In other embodiments, the alkyl or alkylene is a $C_1$-$C_{10}$ alkyl or $C_1$-$C_{10}$ alkylene (e.g. a $C_1$-$C_5$ alkyl or $C_1$-$C_5$ alkylene).

In some embodiments, is a compound having the formula:

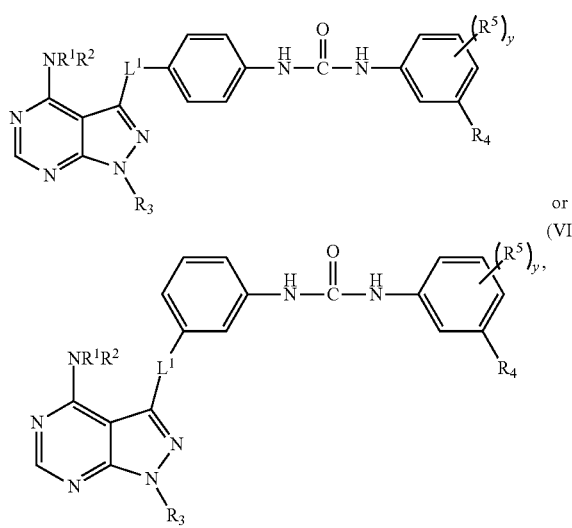

wherein $R^1$ and $R^2$ are independently hydrogen or substituted or unsubstituted alkyl; $R^3$ is independently substituted or unsubstituted alkyl; $R^4$ is independently halogen, —CN, —$CX_3$, —S(O)$_2$H, —NO, —NO$_2$, —C(O)H, —C(O)NH$_2$, —S(O)$_2$NH$_2$, or —CO$_2$H; $R^5$ is independently halogen, —CN, —$CX^a_3$, —S(O)$_2$H, —NO, —NO$_2$, —C(O)H, —C(O)NH$_2$, —S(O)$_2$NH$_2$, or —CO$_2$H; $L^1$ is independently a bond or substituted or unsubstituted alkylene; the symbol y is independently an integer from 0 to 4; and the symbols X and $X^a$ are independently —F, —Cl, —Br, or —I. In some embodiments of the compounds having formula (V) or (VI), $R^1$, $R^2$, $R^3$, $R^4$, $R^5$, $L^1$, X, $X^a$, and y are as described herein for any other formula or compound (including embodiments).

In some embodiments of the compound having formula (I) or (III) or (V), the compound has a formula selected from the group including formulas:

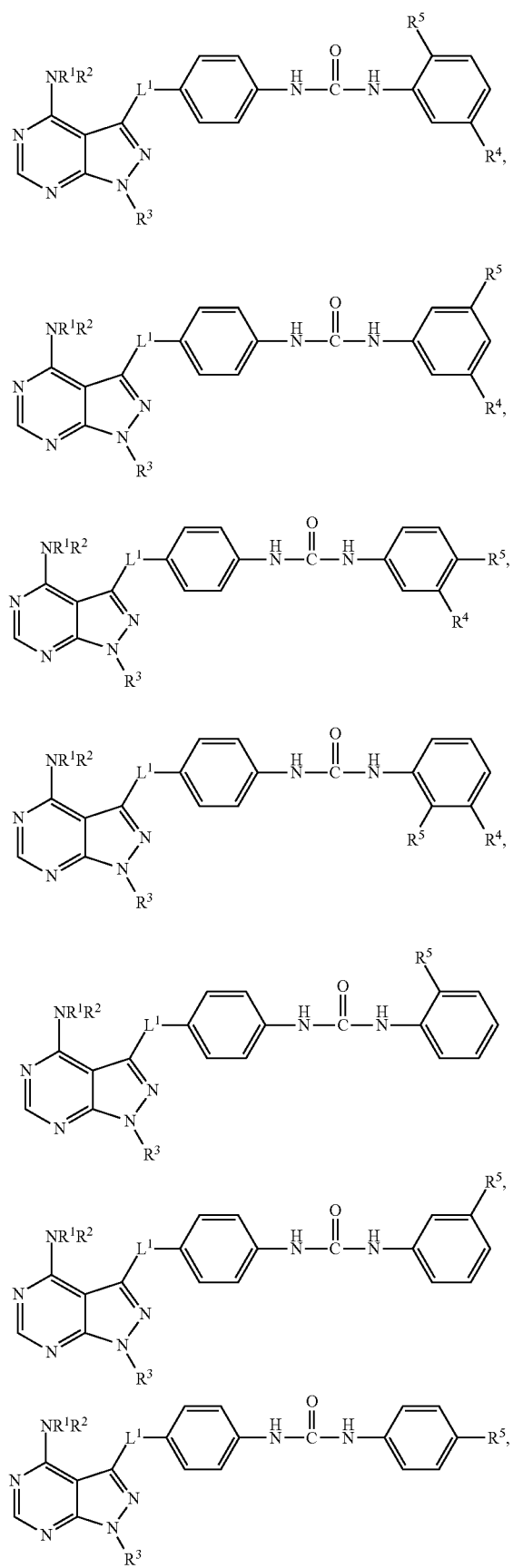

39
-continued
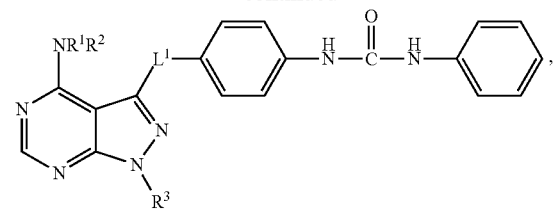
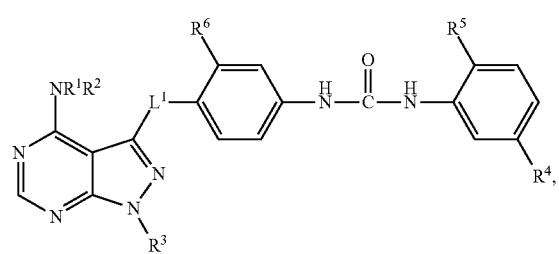
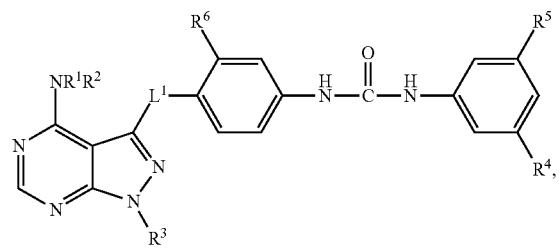
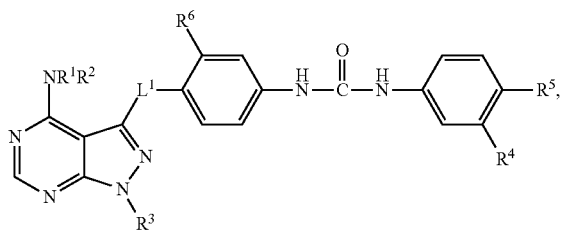
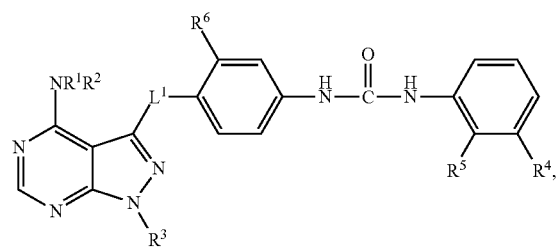
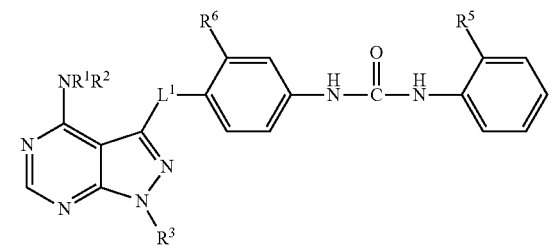
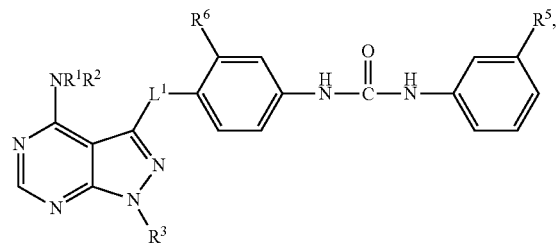
40
-continued
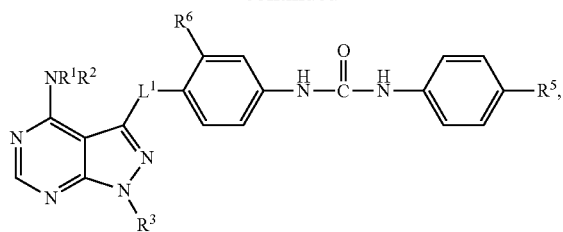
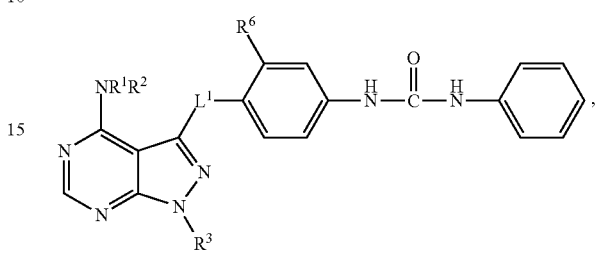
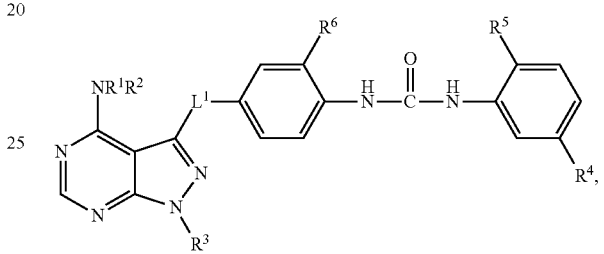
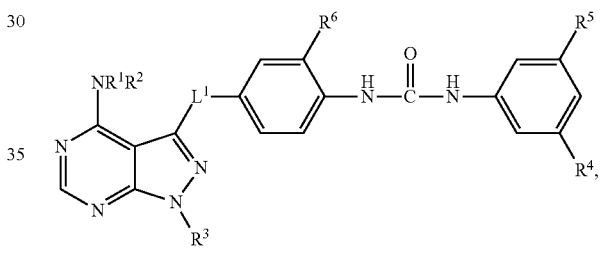
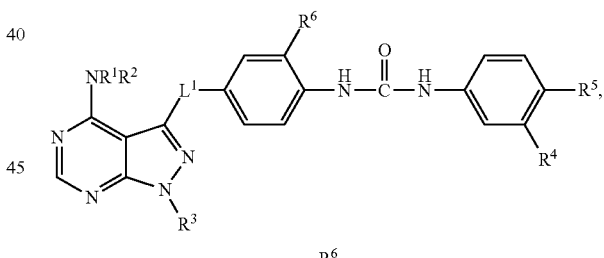
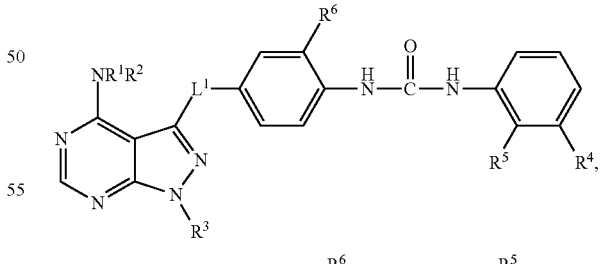
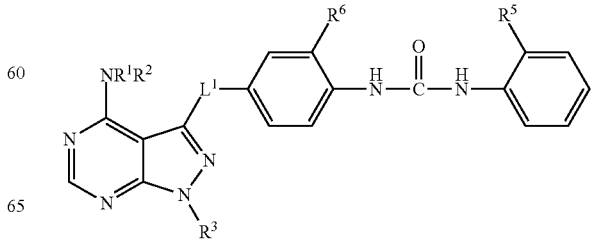

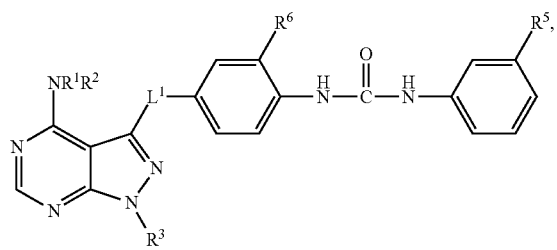

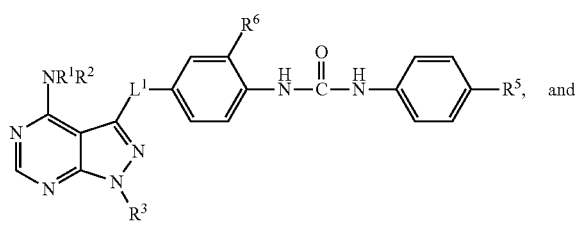

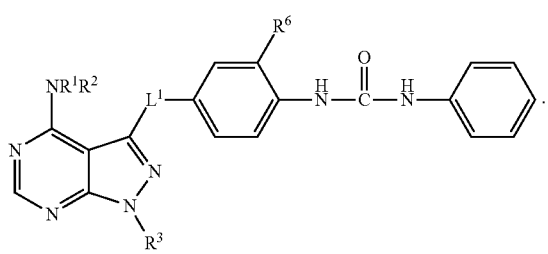

In the compounds above, $R^1$, $R^2$, $R^3$, $R^4$, $R^5$, $R^6$, $L^1$, X, $X^a$, $X^b$, y, z1, and z2 are as described herein (e.g. formula (I), (II), (III), (IV), (V), and (VI), including embodiments). In some embodiments, $R^4$ is —$CF_3$. In some embodiments, $R^5$ is —$CF_3$ or halogen (e.g. —F). In some embodiments, $R^6$ is hydrogen or halogen (e.g. —F). In some embodiments, $R^3$ is unsubstituted alkyl (e.g. $C_1$-$C_6$ alkyl). In some embodiments, $R^1$ and $R^2$ are hydrogen. In some embodiments, $L^1$ is a bond or methylene.

In some embodiments of the compound having formula (I), the compound has the formula (V). In some embodiments of the compound having formula (II), the compound has the formula (VI). In some embodiments of the compound having formula (I), the compound has the formula (VII). In some embodiments of the compound having formula (I), the compound has the formula (VIII). In some embodiments of the compound having formula (I), the compound has the formula (IX). In some embodiments of the compound having formula (II), the compound has the formula (X). In some embodiments of the compound having formula (I), the compound has the formula (XI). In some embodiments of the compound having formula (I), the compound has the formula (XII). In some embodiments of the compound having formula (I), the compound has the formula (XIII) In some embodiments of the compound having formula (I), the compound has the formula (XIV). In some embodiments of the compound having formula (I), the compound has the formula (XV). In some embodiments of the compound having formula (I), the compound has the formula (XVI). In some embodiments of the compound having formula (I), the compound has the formula (XVII). In some embodiments of the compound having formula (I), the compound has the formula (XVIII).

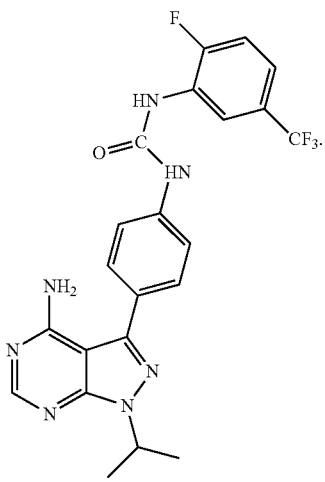

(VII) or (AD80)

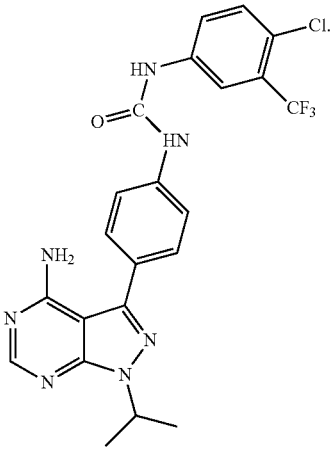

(VIII) or (AD81)

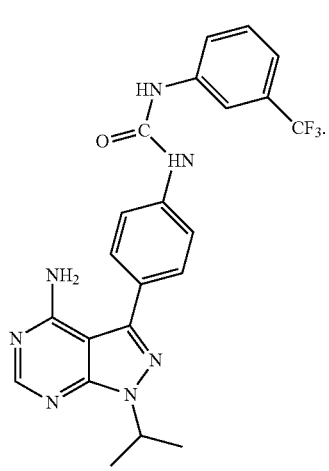

(IX) or (AD57)

(X) or (AD36)
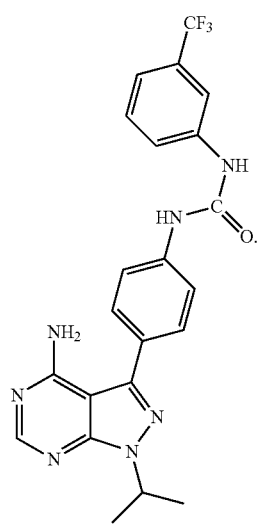
(XIII)
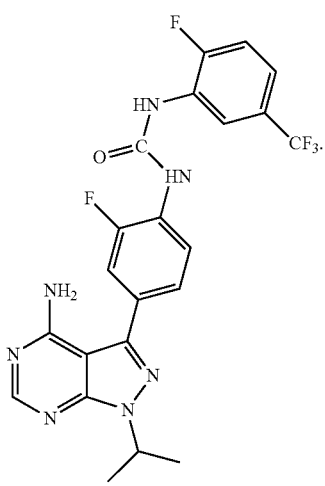
(XI)
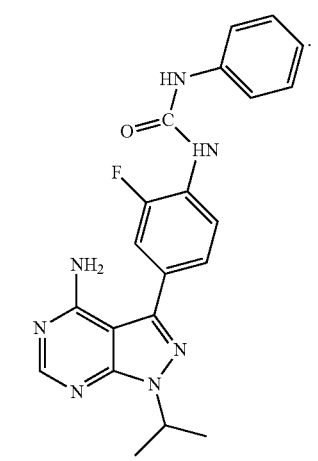
(XV)
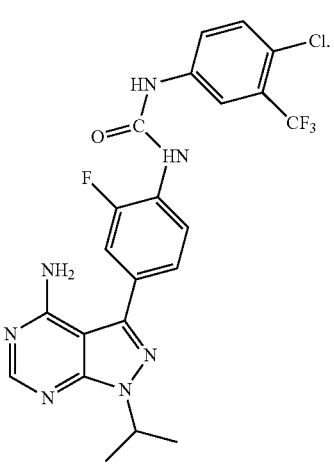 [SMILES: CC(C)n1nc(-c2ccc(NC(=O)Nc3ccc(Cl)c(C(F)(F)F)c3)cc2)c2c(N)ncnc21]
(XII)
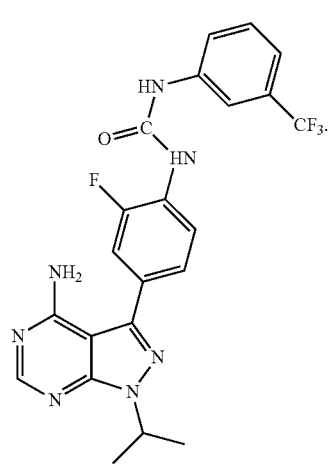
(XV)
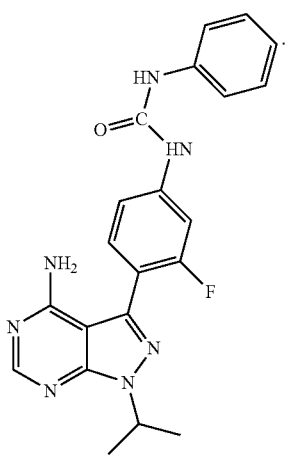

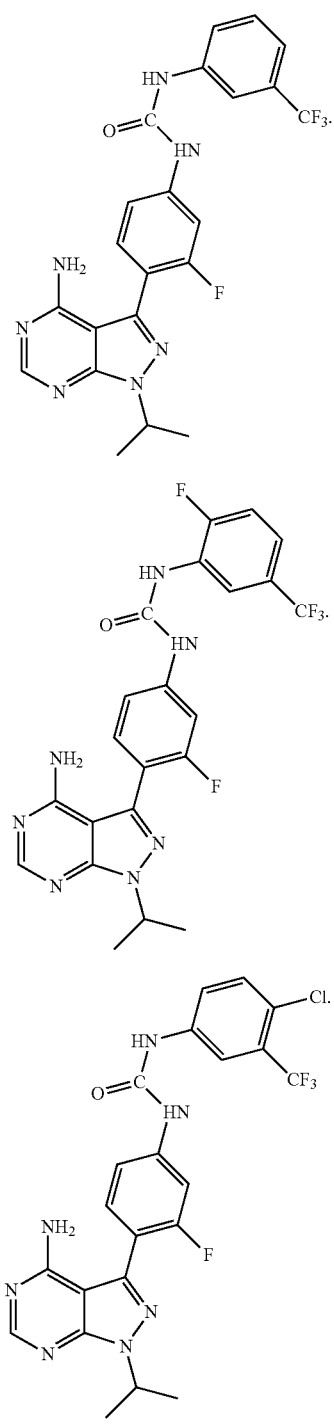

embodiments, the compound is an AXL modulator. In some embodiments, the compound is a GAS6 modulator.

In some embodiments of the compounds provided herein, $R^1$ is hydrogen, or $R^{20}$-substituted or unsubstituted alkyl. In some embodiments of the compounds provided herein, $R^1$ is $R^{20}$-substituted or unsubstituted ($C_1$-$C_6$) alkyl. In some embodiments of the compounds provided herein, $R^1$ is $R^{20}$-substituted or unsubstituted ($C_1$-$C_4$) alkyl.

$R^{20}$ is independently halogen, oxo, —$CF_3$, —CN, —OH, —$NH_2$, —COOH, —$CONH_2$, —NO, —$NO_2$, —C(O)H, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{21}$ is independently halogen, oxo, —$CF_3$, —CN, —OH, —$NH_2$, —COOH, —$CONH_2$, —NO, —$NO_2$, —C(O)H, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In some embodiments of the compounds provided herein, $R^2$ is hydrogen, or $R^{23}$-substituted or unsubstituted alkyl. In some embodiments of the compounds provided herein, $R^2$ is $R^{23}$-substituted or unsubstituted ($C_1$-$C_6$) alkyl. In some embodiments of the compounds provided herein, $R^2$ is $R^{23}$-substituted or unsubstituted ($C_1$-$C_4$) alkyl.

$R^{23}$ is independently halogen, oxo, —$CF_3$, —CN, —OH, —$NH_2$, —COOH, —$CONH_2$, —NO, —$NO_2$, —C(O)H, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{24}$-substituted or unsubstituted ($C_1$-$C_6$) alkyl, $R^{24}$-substituted or unsubstituted 2 to 6 membered heteroalkyl, $R^{24}$-substituted or unsubstituted ($C_3$-$C_6$) cycloalkyl, $R^{24}$-substituted or unsubstituted 3 to 6 membered heterocycloalkyl, $R^{24}$-substituted or unsubstituted ($C_6$-$C_{10}$) aryl, or $R^{24}$-substituted or unsubstituted 5 to 10 membered heteroaryl.

$R^{24}$ is independently halogen, oxo, —$CF_3$, —CN, —OH, —$NH_2$, —COOH, —$CONH_2$, —NO, —$NO_2$, —C(O)H, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{25}$-substituted or unsubstituted ($C_1$-$C_6$) alkyl, $R^{25}$-substituted or unsubstituted 2 to 6 membered heteroalkyl, $R^{25}$-substituted or unsubstituted ($C_3$-$C_6$) cycloalkyl, $R^{25}$-substituted or unsubstituted 3 to 6 membered heterocycloalkyl, $R^{25}$-substituted or unsubstituted ($C_6$-$C_{10}$) aryl, or $R^{25}$-substituted or unsubstituted 5 to 10 membered heteroaryl.

In some embodiments of the compounds provided herein, $R^3$ is $R^{26}$-substituted or unsubstituted alkyl. In some embodiments of the compounds provided herein, $R^3$ is $R^{26}$-substituted or unsubstituted ($C_1$-$C_6$) alkyl. In some embodiments of the compounds provided herein, $R^3$ is $R^{26}$-substituted or unsubstituted ($C_1$-$C_4$) alkyl.

$R^{26}$ is independently halogen, oxo, —$CF_3$, —CN, —OH, —$NH_2$, —COOH, —$CONH_2$, —NO, —$NO_2$, —C(O)H, —SH, —$SO_2O$, —$SO_3H$, —$SO_4H$, —$SO_2NH_2$, —$NHNH_2$, In some embodiments, a compound as described herein (e.g. formula (I) to (XVIII), including embodiments thereof) is a Ret modulator. In some embodiments, the compound is a Raf modulator. In some embodiments, the compound is a B-Raf modulator. In some embodiments, the compound is a Src modulator. In some embodiments, the compound is a S6K kinase modulator. In some embodiments, the compound is a S6K2 kinase modulator. In some embodiments, the compound is an mTOR modulator. In some embodiments, the compound is not an mTOR modulator. In some —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{27}$-substituted or unsubstituted (C$_1$-C$_6$) alkyl, R$^{27}$-substituted or unsubstituted 2 to 6 membered heteroalkyl, R$^{27}$-substituted or unsubstituted (C$_3$-C$_6$) cycloalkyl, R$^{27}$-substituted or unsubstituted 3 to 6 membered heterocycloalkyl, R$^{27}$-substituted or unsubstituted (C$_6$-C$_{10}$) aryl, or R$^{27}$-substituted or unsubstituted 5 to 10 membered heteroaryl.

R$^{27}$ is independently halogen, oxo, —CF$_3$, —CN, —OH, —NH$_2$, —COOH, —CONH$_2$, —NO, —NO$_2$, —C(O)H, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{28}$-substituted or unsubstituted (C$_1$-C$_6$) alkyl, R$^{28}$-substituted or unsubstituted 2 to 6 membered heteroalkyl, R$^{28}$-substituted or unsubstituted (C$_3$-C$_6$) cycloalkyl, R$^{28}$-substituted or unsubstituted 3 to 6 membered heterocycloalkyl, R$^{28}$-substituted or unsubstituted (C$_6$-C$_{10}$) aryl, or R$^{28}$-substituted or unsubstituted 5 to 10 membered heteroaryl.

In some embodiments of the compounds provided herein, R$^4$ is independently hydrogen, halogen, —CF$_3$, —CN, —OH, —COOH, —CONH$_2$, —NO, —NO$_2$, —C(O)H, —SH, —SO$_2$Cl, —SO$_3$H, —SO$_4$H, —SO$_2$NH$_2$, —NHNH$_2$, —ONH$_2$, —NHC=(O)NHNH$_2$, —C(O)CH$_3$, —NHC=(O)NH$_2$, —NHSO$_2$H, —NHC=(O)H, —NHC(O)—OH, —NHOH, —OCF$_3$, —OCHF$_2$, or R$^{29}$-substituted or unsubstituted (C$_1$-C$_6$) alkyl. In some embodiments of the compounds provided herein, R$^4$ is R$^{29}$-substituted or unsubstituted (C$_1$-C$_4$) alkyl.

R$^{29}$ is independently halogen, oxo, —CF$_3$, —CN, —OH, —NH$_2$, —COOH, —CONH$_2$, —NO, —NO$_2$, —C(O)H, —SH, —SO$_2$O, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{30}$-substituted or unsubstituted (C$_1$-C$_6$) alkyl, R$^{30}$-substituted or unsubstituted 2 to 6 membered heteroalkyl, R$^{30}$-substituted or unsubstituted (C$_3$-C$_6$) cycloalkyl, R$^{30}$-substituted or unsubstituted 3 to 6 membered heterocycloalkyl, R$^{30}$-substituted or unsubstituted (C$_6$-C$_{10}$) aryl, or R$^{30}$-substituted or unsubstituted 5 to 10 membered heteroaryl.

R$^{30}$ is independently halogen, oxo, —CF$_3$, —CN, —OH, —NH$_2$, —COOH, —CONH$_2$, —NO, —NO$_2$, —C(O)H, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{31}$-substituted or unsubstituted (C$_1$-C$_6$) alkyl, R$^{31}$-substituted or unsubstituted 2 to 6 membered heteroalkyl, R$^{31}$-substituted or unsubstituted (C$_3$-C$_6$) cycloalkyl, R$^{31}$-substituted or unsubstituted 3 to 6 membered heterocycloalkyl, R$^{31}$-substituted or unsubstituted (C$_6$-C$_{10}$) aryl, or R$^{31}$-substituted or unsubstituted 5 to 10 membered heteroaryl.

In some embodiments of the compounds provided herein, R$^5$ is independently hydrogen, halogen, —CF$_3$, —CN, —OH, —COOH, —CONH$_2$, —NO, —NO$_2$, —C(O)H, —SH, —SO$_2$Cl, —SO$_3$H, —SO$_4$H, —SO$_2$NH$_2$, —NHNH$_2$, —ONH$_2$, —NHC=(O)NHNH$_2$, —C(O)CH$_3$, —NHC=(O)NH$_2$, —NHSO$_2$H, —NHC=(O)H, —NHC(O)—OH, —NHOH, —OCF$_3$, —OCHF$_2$, or R$^{32}$-substituted or unsubstituted (C$_1$-C$_6$) alkyl. In some embodiments of the compounds provided herein, R$^5$ is R$^{32}$-substituted or unsubstituted (C$_1$-C$_4$) alkyl.

R$^{32}$ is independently halogen, oxo, —CF$_3$, —CN, —OH, —NH$_2$, —COOH, —CONH$_2$, —NO, —NO$_2$, —C(O)H, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{33}$-substituted or unsubstituted (C$_1$-C$_6$) alkyl, R$^{33}$-substituted or unsubstituted 2 to 6 membered heteroalkyl, R$^{33}$-substituted or unsubstituted (C$_3$-C$_6$) cycloalkyl, R$^{33}$-substituted or unsubstituted 3 to 6 membered heterocycloalkyl, R$^{33}$-substituted or unsubstituted (C$_6$-C$_{10}$) aryl, or R$^{33}$-substituted or unsubstituted 5 to 10 membered heteroaryl.

R$^{33}$ is independently halogen, oxo, —CF$_3$, —CN, —OH, —NH$_2$, —COOH, —CONH$_2$, —NO, —NO$_2$, —C(O)H, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{34}$-substituted or unsubstituted (C$_1$-C$_6$) alkyl, R$^{34}$-substituted or unsubstituted 2 to 6 membered heteroalkyl, R$^{34}$-substituted or unsubstituted (C$_3$-C$_6$) cycloalkyl, R$^{34}$-substituted or unsubstituted 3 to 6 membered heterocycloalkyl, R$^{34}$-substituted or unsubstituted (C$_6$-C$_{10}$) aryl, or R$^{34}$-substituted or unsubstituted 5 to 10 membered heteroaryl.

In some embodiments of the compounds provided herein, R$^6$ is independently hydrogen, halogen, —CF$_3$, —CN, —OH, —COOH, —CONH$_2$, —NO, —NO$_2$, —C(O)H, —SH, —SO$_2$Cl, —SO$_3$H, —SO$_4$H, —SO$_2$NH$_2$, —NHNH$_2$, —ONH$_2$, —NHC=(O)NHNH$_2$, —C(O)CH$_3$, —NHC=(O)NH$_2$, —NHSO$_2$H, —NHC=(O)H, —NHC(O)—OH, —NHOH, —OCF$_3$, —OCHF$_2$.

In some embodiments of the compounds provided herein, L$^1$ is a bond or R$^{38}$-substituted or unsubstituted alkylene. In some embodiments of the compounds provided herein, L$^1$ is R$^{38}$-substituted or unsubstituted (C$_1$-C$_6$) alkylene. In some embodiments of the compounds provided herein, L$^1$ is R$^{38}$-substituted or unsubstituted (C$_1$-C$_4$) alkylene. In some embodiments of the compounds provided herein, L$^1$ is R$^{38}$-substituted or unsubstituted methylene. In some embodiments of the compounds provided herein, L$^1$ is R$^{38}$-substituted or unsubstituted ethylene. In some embodiments of the compounds provided herein, L$^1$ is R$^{38}$-substituted or unsubstituted propylene. In some embodiments of the compounds provided herein, L$^1$ is R$^{38}$-substituted or unsubstituted n-propylene. In some embodiments of the compounds provided herein, L$^1$ is R$^{38}$-substituted or unsubstituted 2-propylene. In some embodiments of the compounds provided herein, L$^1$ is a bond.

R$^{38}$ is independently halogen, oxo, —CF$_3$, —CN, —OH, —NH$_2$, —COOH, —CONH$_2$, —NO, —NO$_2$, —C(O)H, —SH, —SO$_2$O, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{39}$-substituted or unsubstituted alkyl, R$^{39}$-substituted or unsubstituted heteroalkyl, R$^{39}$-substituted or unsubstituted cycloalkyl, R$^{39}$ substituted or unsubstituted heterocycloalkyl, R$^{39}$-substituted or unsubstituted aryl, or R$^{39}$-substituted or unsubstituted heteroaryl. In some embodiments, R$^{38}$ is R$^{39}$-substituted or unsubstituted (C$_1$-C$_6$) alkyl, R$^{39}$-substituted or unsubstituted 2 to 6 membered heteroalkyl, R$^{39}$-substituted or unsubstituted (C$_3$-C$_6$) cycloalkyl, R$^{39}$-substituted or unsubstituted 3 to 6 membered heterocycloalkyl, R$^{39}$-substituted or unsubstituted (C$_6$-C$_{10}$) aryl, or R$^{39}$-substituted or unsubstituted 5 to 10 membered heteroaryl.

R$^{39}$ is independently halogen, oxo, —CF$_3$, —CN, —OH, —NH$_2$, —COOH, —CONH$_2$, —NO, —NO$_2$, —C(O)H, —SH, —SO$_2$O, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl.

In some embodiments of the compounds provided herein, R$^{22}$, R$^{25}$, R$^{28}$, R$^{31}$, R$^{34}$, and R$^{40}$ re independently hydrogen, halogen, oxo, —CF$_3$, —CN, —OH, —NH$_2$, —COOH, —CONH$_2$, —NO, —NO$_2$, —C(O)H, —SH, —SO$_2$O, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted (C$_1$-C$_6$) alkyl, unsubstituted 2 to 6 membered heteroalkyl, unsubstituted (C$_3$-C$_6$) cycloalkyl, unsubstituted 3 to 6 membered heterocycloalkyl, unsubstituted (C$_6$-C$_{10}$) aryl, or unsubstituted 5 to 10 membered heteroaryl.

C. Pharmaceutical Compositions and Methods

In a second aspect is a pharmaceutical composition including a pharmaceutically acceptable excipient and a compound as described herein (also referred to herein as "compound of the present invention" or "active component") (e.g. formula (I) to (XVIII), including embodiments thereof). In some embodiments, the pharmaceutical composition further includes an anti-cancer agent. In some embodiments, the anti-cancer agent is an EGFR-targeted therapy or therapeutic such as erlotinib or gefitinib. In some embodiments, the anti-cancer agent is a MEK-targeted therapy or therapeutic (e.g. PD325901, trametinib).

In a third aspect is a method of treating cancer in a subject in need thereof, the method including administering to the subject an effective amount of a compound as described herein (e.g. formula (I) to (XVIII), including embodiments thereof). In some embodiments, the compound forms part of the pharmaceutical composition provided herein.

In some embodiments of a method of treating cancer, the cancer is associated with multiple endocrine neoplasm 2. In some embodiments, the cancer is associated with multiple endocrine neoplasm 2A. In some embodiments, the cancer is associated with multiple endocrine neoplasm 2B. In some embodiments, the cancer is associated with aberrant AXL kinase activity (e.g. lung cancer, non-small cell lung cancer, drug resistant lung cancer, breast cancer, pancreatic cancer, metastatic lung, breast, or pancreatic cancer). In some embodiments, the cancer is associated with aberrant GAS6 function (e.g. lung cancer, non-small cell lung cancer, drug resistant lung cancer, breast cancer, pancreatic cancer, metastatic lung, breast, or pancreatic cancer). In some embodiments, the cancer is associated with aberrant Ret kinase activity (e.g. medullary thyroid carcinoma, pheochromocytoma, primary hyperparathyroidism, intestinal ganglioneuromatosis, parathyroid hyperplasia, familial medullary thyroid cancer, or mucosal neuromas). In some embodiments, the cancer is associated with aberrant Ret kinase activity (e.g. non-small cell lung cancer expressing a CCDC6-RET fusion protein, non-small cell lung cancer expressing a KIF5B-RET fusion protein, thyroid cancer expressing a CCDC6-RET fusion protein). In some embodiments, the cancer is associated with aberrant Raf kinase activity (e.g. lung cancer, melanoma, colorectal cancer, or papillary thyroid cancer). In some embodiments, the cancer is associated with aberrant B-Raf kinase activity (e.g. lung cancer, melanoma, colorectal cancer, or papillary thyroid cancer). In some embodiments, the cancer is associated with aberrant Src kinase activity (e.g. breast cancer). In some embodiments, the cancer is associated with aberrant S6K kinase activity (e.g. hepatocellular carcinoma or lung cancer). In some embodiments, the cancer is associated with aberrant mTOR activity. In some embodiments, the cancer is associated with aberrant S6K2 activity. In some embodiments, the cancer is associated with aberrant Ret, Raf, Src, and S6K kinase activity. In some embodiments, the cancer is familial medullary thyroid cancer. In some embodiments, the cancer is medullary thyroid carcinoma, pheochromocytoma, primary hyperparathyroidism, intestinal ganglioneuromatosis, parathyroid hyperplasia, or mucosal neuromas. In some embodiments, the cancer is medullary thyroid carcinoma. In some embodiments, the cancer is pheochromocytoma. In some embodiments, the cancer is primary hyperparathyroidism. In some embodiments, the cancer is intestinal ganglioneuromatosis. In some embodiments, the cancer is parathyroid hyperplasia. In some embodiments, the cancer is mucosal neuromas. In some embodiments, the cancer is lung cancer. In some embodiments, the cancer is melanoma. In some embodiments, the cancer is colorectal cancer. In some embodiments, the cancer is papillary thyroid cancer. In some embodiments, the cancer is breast cancer. In some embodiments, the cancer is hepatocellular carcinoma. In some embodiments, the cancer is melanoma, colorectal cancer, papillary thyroid cancer, breast cancer, hepatocellular carcinoma, or lung cancer. In some embodiments, the cancer is metastatic cancer. In some embodiments, the cancer has metastasized to a different location from the primary tumor. In some embodiments, the cancer is non-small cell lung cancer. In some embodiments, the cancer is resistant to one or more anti-cancer agents such as an EGFR-targeted therapy or therapeutic (e.g. as described herein). In some embodiments, the cancer is erlotinib resistant. In some embodiments, the cancer is gefitinib resistant. In some embodiments, the cancer is erlotinib resistant lung cancer. In some embodiments, the cancer is gefitinib resistant lung cancer. In some embodiments of treating cancer, the method further includes administering an effective amount of an anti-cancer agent. In some embodiments, the anti-cancer agent is an EGFR-targeted therapy or therapeutic. In some embodiments, the anti-cancer agent is erlotinib. In some embodiments, the anti-cancer agent is gefitinib. In some embodiments, the anti-cancer agent is a MEK-targeted therapy or therapeutic. In some embodiments, the cancer is non-small cell lung cancer expressing CCDC6-RET fusion protein. In some embodiments, the cancer is non-small cell lung cancer expressing KIF5B-RET fusion protein. In some embodiments, the cancer is thyroid cancer expressing CCDC6-RET fusion protein. In some embodiments, the cancer is thyroid cancer expressing CCDC6-RET fusion protein and the method further includes administering a MEK inhibitor (e.g. PD325901). In some embodiments, the cancer is non-small cell lung cancer expressing KIF5B-RET fusion protein and the method further includes administering a MEK inhibitor (e.g. PD325901). In some embodiments, the cancer is non-small cell lung cancer expressing CCDC6-RET fusion protein and the method further includes administering a MEK inhibitor (e.g. PD325901). In some embodiments, the cancer expresses a RET fusion protein.

In a fourth aspect is a method of reducing the activity of RET kinase, Raf kinase, Src kinase, and S6K kinase, the method including contacting a RET kinase, a Raf kinase, a Src kinase, and a S6K kinase with an effective amount of a compound as described herein (e.g. formula (I) to (XVIII), including embodiments thereof). In some embodiments, Raf kinase is B-Raf kinase. In some embodiments, the method does not include reducing the activity of mTOR kinase. In some embodiments, the compound forms part of the pharmaceutical composition provided herein. In some embodiments, the compound is AD57. In some embodiments, the compound is AD80. In some embodiments, the compound is AD81. In some embodiments, the compound is selected from any of the compounds described herein, including in any table, figure, or example.

In a fifth aspect is a method of reducing the activity of AXL kinase, the method including contacting an AXL kinase with an effective amount of a compound as described herein (e.g. formula (I) to (XVIII), including embodiments thereof). In some embodiments of the method of reducing the activity of AXL kinase, the compound is AD57. In some embodiments of the method of reducing the activity of AXL kinase, the compound is AD80. In some embodiments of the method of reducing the activity of AXL kinase, the compound is AD81. In some embodiments of the method of reducing the activity of AXL kinase, the compound is selected from any of the compounds described herein, including in any table, figure, or example.

In some embodiments of the methods described herein, the compound is

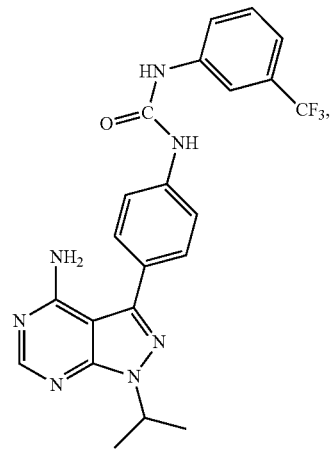

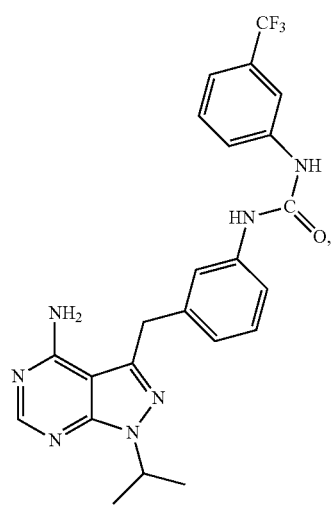

-continued

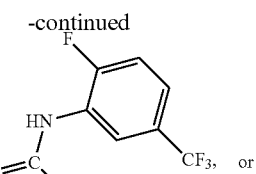

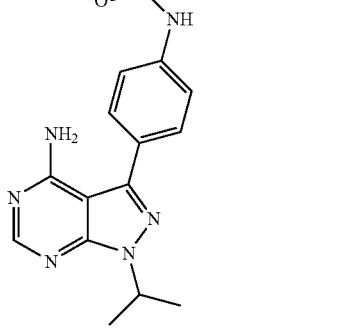

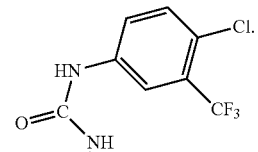

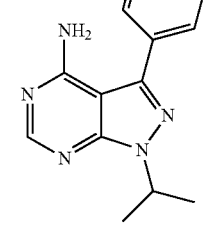

The pharmaceutical compositions include optical isomers, diastereomers, or pharmaceutically acceptable salts of the modulators disclosed herein. The compound included in the pharmaceutical composition may be covalently attached to a carrier moiety, as described above. Alternatively, the compound included in the pharmaceutical composition is not covalently linked to a carrier moiety.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation, anti-cancer agents).

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component (e.g. a compound provided herein). In tablets, the active component (e.g. compound provided herein) is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. a kinase or kinase(s); RET; Raf; B-Raf; Src; S6K kinase; or RET, Raf, Src, and S6K kinase; or RET, B-Raf, Src, and S6K kinase; or AXL kinase and/or GAS6), and/or reducing, eliminating, or slowing the progression of disease symptoms (e.g. cancer growth or metastasis). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. multiple endocrine neoplasia 2, multiple endocrine neoplasia 2A, multiple endocrine neoplasia 2B, familial medullary thyroid cancer, medullary thyroid carcinoma, pheochromocytoma, primary hyperparathyroidism, intestinal ganglioneuromatosis, parathyroid hyperplasia, thyroid cancer, lung cancer, non-small cell lung cancer, breast cancer, pancreatic cancer, glioblastoma, AXL associated cancer, or mucosal neuromas), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

D. Administration

The compositions of the present invention can be delivered by transdermally, by a topical route, formulated as applicator sticks, solutions, suspensions, emulsions, gels, creams, ointments, pastes, jellies, paints, powders, and aerosols. For therapeutic applications, the compounds or drugs of the present invention can be administered alone or co-administered in combination with conventional chemotherapy, radiotherapy, hormonal therapy, and/or immunotherapy.

The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Pharmaceutical compositions described herein may be salts of a compound or composition which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compositions described herein or kinase inhibitor compounds of the present invention can exist in unsolvated forms as well as solvated forms, including hydrated forms. In general, the solvated forms are equivalent to unsolvated forms and are intended to be encompassed within the scope of the present invention. Certain kinase inhibitor compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.*

13:293-306, 1996; Chonn, *Curr. Opin. Biotechnol.* 6:698-708, 1995; Ostro, *Am. J. Hosp. Pharm.* 46:1576-1587, 1989).

The compounds described herein can be used in combination with one another, with other active agents (e.g. anti-cancer agents) known to be useful in treating a disease (e.g. cancer, MEN2 associated cancer, AXL kinase associated cancer, resistant cancer, EGFR-therapy resistant cancer, EGFR-therapeutic resistant cancer), or other active agents known to be useful in treating a disease associated with cells expressing a particular kinase (e.g. Ret kinase, Raf kinase, Src kinase, S6K kinase, AXL kinase, B-Raf kinase), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), other kinase inhibitors, and the like.

The kinase inhibitor compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y $^{90}$Y, $^{105}$Rh, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

As non-limiting examples, the compositions, drugs, and compounds described herein (including compounds any of formulas (I) to (XVIII) and including embodiments thereof) can be co-administered with or used in combination with anti-cancer agents including, but not limited to the anti-cancer agents described herein. In some embodiments, the compounds described herein (including embodiments) may be co-administered with or used in combination with an EGFR-targeted therapy or EGFR-targeted therapeutic (e.g. gefitinib (Iressa™), erlotinib (Tarceva™) cetuximab (Erbitux™), lapatinib (Tykerb™), panitumumab (Vectibix™), vandetanib (Caprelsa™)). In some embodiments, the compounds described herein (including compounds any of formulas (I) to (XVIII) and including embodiments thereof) may be co-administered with or used in combination with a MEK-targeted therapy or MEK-targeted therapeutic.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged kinase inhibitor compound or drug suspended in diluents, e.g., water, saline, or PEG 400; (b) capsules, sachets, or tablets, each containing a predetermined amount of a kinase inhibitor compound or drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise compounds described herein or drug in a flavor, e.g., sucrose, as well as pastilles comprising the compounds described herein in an inert base, such as gelatin and glycerin or sucrose and acacia emulsions, gels, and the like, containing, in addition to the compounds described herein, carriers known in the art.

The compounds described herein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged compound described herein or drug with a suppository base. Suitable suppository bases include natural or synthetic triglycerides or paraffin hydrocarbons. In addition, it is also possible to use gelatin rectal capsules which contain a combination of a compound described herein or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a kinase inhibitor compound. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of cancer, compounds described herein utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compounds or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound described herein in a particular patient. Determination of the proper dosage for a particular situation is within the skill of the practitioner. Generally, treatment is initiated with smaller dosages which are less than the optimum dose of the kinase inhibitor compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent. The compounds and methods described herein include any of the compounds described herein or in any table, figure, or example.

E. Additional Embodiments

1. A compound having the formula:

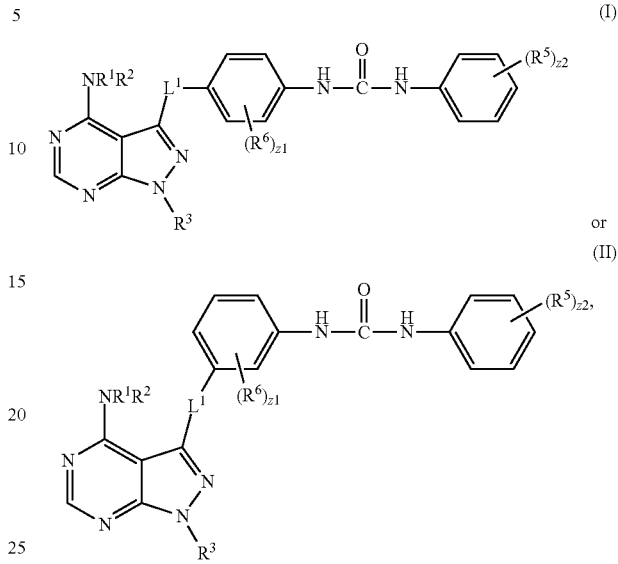

wherein $R^1$ and $R^2$ are independently hydrogen or substituted or unsubstituted alkyl; $R^3$ is independently substituted or unsubstituted alkyl; $R^5$ is independently halogen, —CN, —CX$^a_3$, —S(O)$_2$H, —NO, —NO$_2$, —C(O)H, —C(O)NH$_2$, —S(O)$_2$NH$_2$, —OH, —SH, —SO$_2$Cl, —SO$_3$H, —SO$_4$H, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —CO$_2$H, or substituted or unsubstituted (C$_1$-C$_6$) alkyl; $R^6$ is independently halogen, —CN, —CX$^b_3$, —S(O)$_2$H, —NO, —NO$_2$, —C(O)H, —C(O)NH$_2$, —S(O)$_2$NH$_2$, —OH, —SH, —SO$_2$Cl, —SO$_3$H, —SO$_4$H, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, or —CO$_2$H; $L^1$ is independently a bond or substituted or unsubstituted alkylene; the symbol z1 is independently an integer from 0 to 4; the symbol z2 is independently an integer from 0 to 5; and the symbols $X^a$ and $X^b$ are independently —F, —Cl, —Br, or —I.

2. The compound of embodiment 1, wherein $R^1$ is hydrogen.
3. The compound of embodiment 1, wherein $R^1$ is substituted or unsubstituted alkyl.
4. The compound of embodiment 1, wherein $R^1$ is unsubstituted alkyl.
5. The compound of embodiment 1, wherein $R^1$ is unsubstituted (C$_1$-C$_6$) alkyl.
6. The compound of any one of embodiments 1 to 5, wherein $R^2$ is hydrogen.
7. The compound of any one of embodiments 1 to 5, wherein $R^2$ is substituted or unsubstituted alkyl.
8. The compound of any one of embodiments 1 to 5, wherein $R^2$ is unsubstituted alkyl.
9. The compound of any one of embodiments 1 to 5, wherein $R^2$ is unsubstituted (C$_1$-C$_6$) alkyl.
10. The compound of any one of embodiments 1 to 9, wherein $L^1$ is a bond.
11. The compound of any one of embodiments 1 to 9, wherein $L^1$ is substituted or unsubstituted alkylene.
12. The compound of any one of embodiments 1 to 9, wherein $L^1$ is unsubstituted alkylene.

13. The compound of any one of embodiments 1 to 9, wherein $L^1$ is unsubstituted ($C_1$-$C_6$) alkylene.
14. The compound of any one of embodiments 1 to 9, wherein $L^1$ is unsubstituted methylene.
15. The compound of any one of embodiments 1 to 14, wherein $R^3$ is substituted or unsubstituted alkyl.
16. The compound of any one of embodiments 1 to 14, wherein $R^3$ is unsubstituted alkyl.
17. The compound of any one of embodiments 1 to 14, wherein $R^3$ is unsubstituted ($C_1$-$C_6$) alkyl.
18. The compound of any one of embodiments 1 to 14, wherein $R^3$ is isopropyl.
19. The compound of any one of embodiments 1 to 18, wherein $R^5$ is halogen, —CN, —CX$^a_3$, —NO, —NO$_2$, —C(O)H, or —CO$_2$H.
20. The compound of any one of embodiments 1 to 18, wherein $R^5$ is halogen or —CX$^a_3$.
21. The compound of any one of embodiments 1 to 18, wherein $R^5$ is —CX$^a_3$.
22. The compound of embodiment 21, wherein $X^a$ is —F.
23. The compound of embodiment 21, wherein $X^a$ is —Cl.
24. The compound of embodiment 21, wherein $X^a$ is —Br.
25. The compound of embodiment 21, wherein $X^a$ is —I.
26. The compound of any one of embodiments 1 to 18, wherein $R^5$ is halogen.
27. The compound of embodiment 26, wherein $R^5$ is —F.
28. The compound of embodiment 26, wherein $R^5$ is —Cl.
29. The compound of embodiment 26, wherein $R^5$ is —Br.
30. The compound of embodiment 26, wherein $R^5$ is —I.
31. The compound of any one of embodiments 1 to 30, wherein $R^6$ is halogen, —CN, —CX$^b_3$, —NO, —NO$_2$, —C(O)H, or —CO$_2$H.
32. The compound of any one of embodiments 1 to 30, wherein $R^6$ is halogen or —CX$^b_3$.
33. The compound of any one of embodiments 1 to 30, wherein $R^6$ is —CX$^b_3$.
34. The compound of embodiment 33, wherein $X^b$ is —F.
35. The compound of embodiment 33, wherein $X^b$ is —Cl.
36. The compound of embodiment 33, wherein $X^b$ is —Br.
37. The compound of embodiment 33, wherein $X^b$ is —I.
38. The compound of any one of embodiments 1 to 30, wherein $R^6$ is halogen.
39. The compound of embodiment 38, wherein $R^6$ is —F.
40. The compound of embodiment 38, wherein $R^6$ is —Cl.
41. The compound of embodiment 38, wherein $R^6$ is —Br.
42. The compound of embodiment 38, wherein $R^6$ is —I.
43. The compound of any one of embodiments 1 to 42, wherein z1 is 0.
44. The compound of any one of embodiments 1 to 42, wherein z1 is 1.
45. The compound of any one of embodiments 1 to 42, wherein z1 is 2.
46. The compound of any one of embodiments 1 to 42, wherein z1 is 3.
47. The compound of any one of embodiments 1 to 42, wherein z1 is 4.
48. The compound of any one of embodiments 1 to 47, wherein z2 is 0.
49. The compound of any one of embodiments 1 to 47, wherein z2 is 1.
50. The compound of any one of embodiments 1 to 47, wherein z2 is 2.
51. The compound of any one of embodiments 1 to 47, wherein z2 is 3.
52. The compound of any one of embodiments 1 to 47, wherein z2 is 4.
53. The compound of any one of embodiments 1 to 47, wherein z2 is 5.
54. The compound of any one of embodiments 1 to 47, having the formula

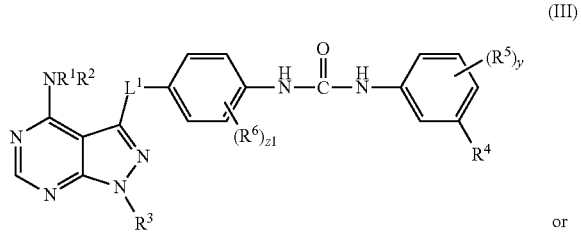

or

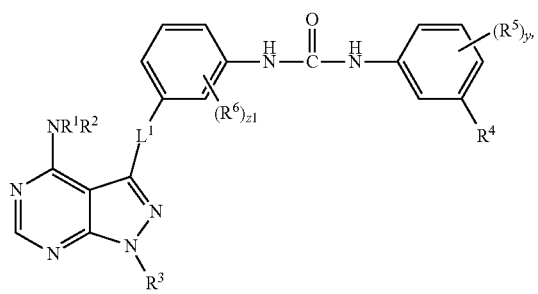

wherein, $R^4$ is independently halogen, —CN, —CX$_3$, —S(O)$_2$H, —NO, —NO$_2$, —C(O)H, —C(O)NH$_2$, —S(O)$_2$NH$_2$, —OH, —SH, —SO$_2$Cl, —SO$_3$H, —SO$_4$H, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —CO$_2$H, or substituted or unsubstituted ($C_1$-$C_6$) alkyl; the symbol y is independently an integer from 0 to 4; and the symbol X is independently —F, —Cl, —Br, or —I.
55. The compound of embodiment 54, wherein $R^4$ is halogen, —CN, —CX$_3$, —NO, —NO$_2$, —C(O)H, or —CO$_2$H.
56. The compound of embodiment 54, wherein $R^4$ is halogen or —CX$_3$.
57. The compound of embodiment 54, wherein $R^4$ is —CX$_3$.
58. The compound of embodiment 57, wherein X is —F.
59. The compound of embodiment 57, wherein X is —Cl.
60. The compound of embodiment 57, wherein X is —Br.
61. The compound of embodiment 57, wherein X is —I.
62. The compound of embodiment 54, wherein $R^4$ is halogen.
63. The compound of embodiment 62, wherein $R^4$ is —F.
64. The compound of embodiment 62, wherein $R^4$ is —Cl.
65. The compound of embodiment 62, wherein $R^4$ is —Br.
66. The compound of embodiment 62, wherein $R^4$ is —I.
67. The compound of any one of embodiments 54 to 66, wherein y is 0.
68. The compound of any one of embodiments 54 to 66, wherein y is 1.
69. The compound of any one of embodiments 54 to 66, wherein y is 2.
70. The compound of any one of embodiments 54 to 66, wherein y is 3.
71. The compound of any one of embodiments 54 to 66, wherein y is 4.
72. The compound of embodiment 1, having a formula selected from the group consisting of:

65
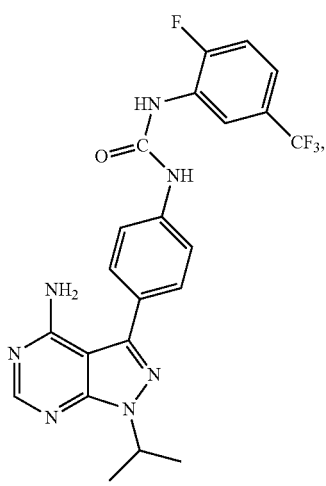
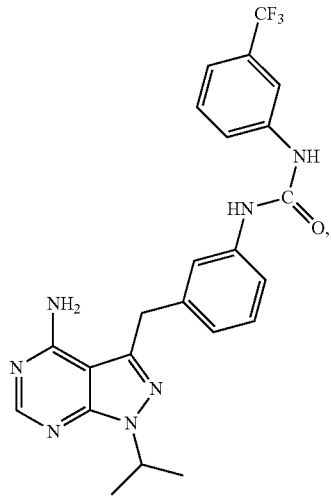
-continued
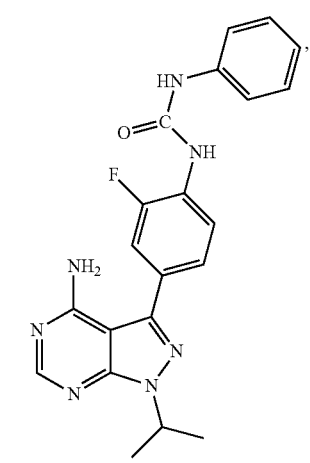
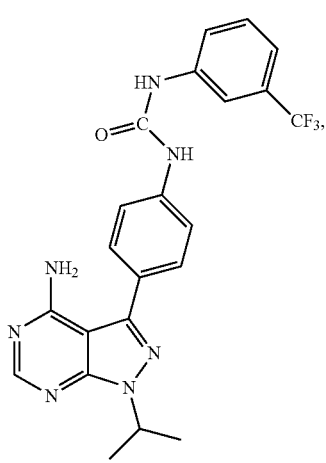

67
-continued
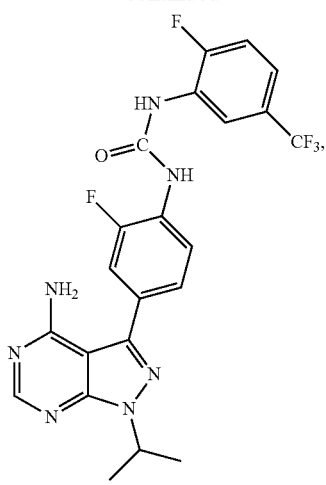
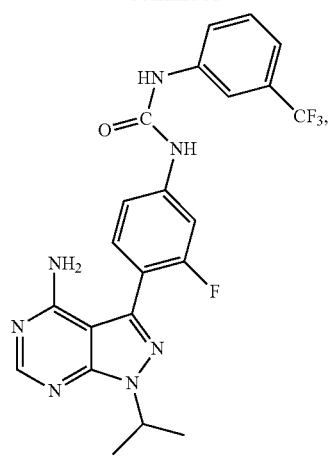
68
-continued
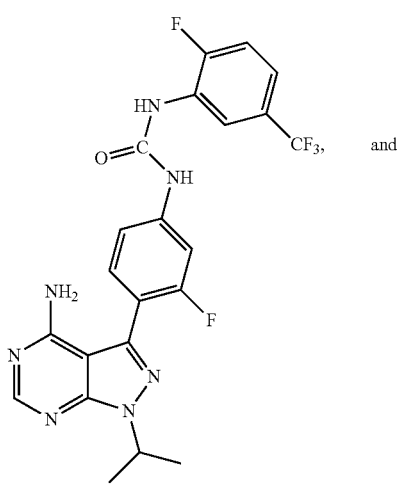
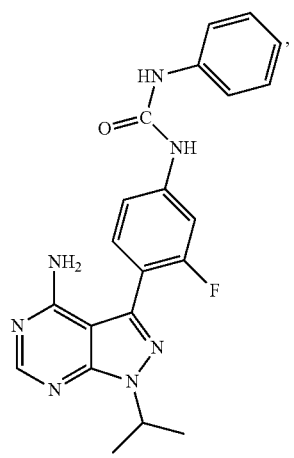
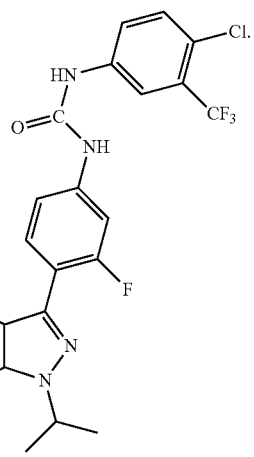
73. The compound of embodiment 1, having a formula selected from the group consisting of:

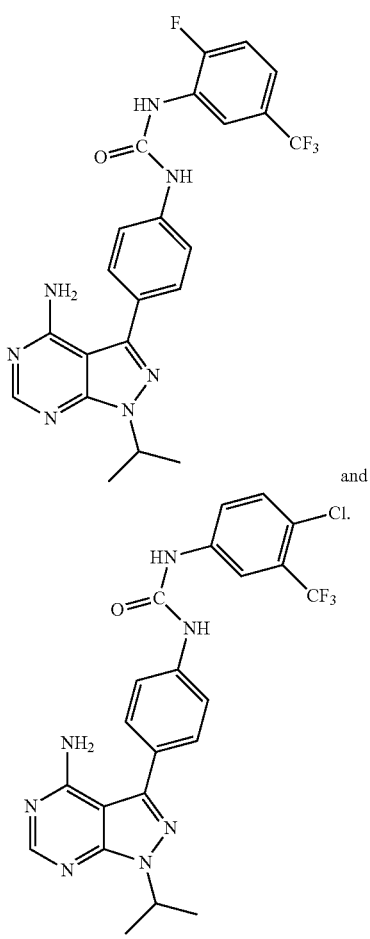

and

74. A pharmaceutical composition comprising a pharmaceutically acceptable excipient and the compound of any one of embodiments 1 to 73.

75. The pharmaceutical composition of embodiment 74, further comprising an anti-cancer agent.

76. The pharmaceutical composition of embodiment 75, wherein said anti-cancer agent is an EGFR-targeted therapy or therapeutic.

77. The pharmaceutical composition of embodiment 76, wherein said EGFR-targeted therapy or therapeutic is erlotinib or gefitinib.

78. The pharmaceutical composition of embodiment 75, wherein said anti-cancer agent is a MEK inhibitor.

79. A method of treating cancer in a subject in need thereof, said method comprising administering to the subject an effective amount of a compound of any one of embodiments 1 to 73.

80. The method of embodiment 79, wherein the cancer is associated with multiple endocrine neoplasm 2.

81. The method of embodiment 79, wherein the cancer is associated with aberrant Ret kinase activity.

82. The method of embodiment 79, wherein the cancer is associated with aberrant Raf kinase activity.

83. The method of embodiment 79, wherein the cancer is associated with aberrant B-Raf kinase activity.

84. The method of embodiment 79, wherein the cancer is associated with aberrant Src kinase activity.

85. The method of embodiment 79, wherein the cancer is associated with aberrant S6K kinase activity.

86. The method of embodiment 79, wherein the cancer is associated with aberrant AXL kinase activity.

87. The method of any one of embodiments 79 to 86, wherein the cancer is resistant to an anti-cancer agent.

88. The method of embodiment 87, wherein the anti-cancer agent is an EGFR-targeted therapy or therapeutic.

89. The method of embodiment 87, wherein the anti-cancer agent is gefitinib or erlotinib.

90. The method of embodiment 87, wherein the anti-cancer agent is a MEK-targeted therapy or therapeutic.

91. The method of any one of embodiments 79 to 90, wherein the cancer is familial medullary thyroid cancer.

92. The method of any one of embodiments 79 to 90, wherein the cancer is medullary thyroid carcinoma, pheochromocytoma, primary hyperparathyroidism, intestinal ganglioneuromatosis, parathyroid hyperplasia, or mucosal neuromas.

93. The method of any one of embodiments 79 to 90, wherein the cancer is melanoma, colorectal cancer, papillary thyroid cancer, breast cancer, hepatocellular carcinoma, pancreatic cancer, chronic myelogenous leukemia, glioblastoma, osteosarcoma, erythroid or megakaryocytic leukemia, uterine cancer, colon cancer, prostate cancer, thyroid cancer, ovarian cancer, liver cancer, gastrointestinal stromal tumors, renal cell carcinoma, acute myeloid leukemia, gastric cancer, or lung cancer.

94. The method of any one of embodiments 79 to 90, wherein the cancer is non-small cell lung cancer.

95. The method of any one of embodiments 79 to 94, further comprising administering to said subject a therapeutically effective amount of an anti-cancer agent.

96. The method of embodiment 95, wherein said anti-cancer agent is an EGFR-targeted therapy or therapeutic.

97. The method of embodiment 95, wherein said anti-cancer agent is erlotinib or gefitinib.

98. The method of embodiment 95, wherein said anti-cancer agent is a MEK-targeted therapy or therapeutic.

99. A method of reducing the activity of Ret kinase, Raf kinase, Src kinase, and S6K kinase, said method comprising contacting a Ret kinase, a Raf kinase, a Src kinase, and a S6K kinase with an effective amount of a compound of any one of embodiments 1 to 73.

100. The method of embodiment 99, wherein the Ret kinase, Raf kinase, Src kinase, and S6K kinase are within a biological cell.

101. The method of embodiment 100, wherein said biological cell is part of an organism.

102. The method of embodiment 100, wherein said biological cell is in vitro.

103. A method of reducing the activity of AXL kinase, said method comprising contacting an AXL kinase with an effective amount of a compound of any one of embodiments 1 to 73.

104. The method of embodiment 103, wherein the AXL kinase is a component of a biological cell.

105. The method of embodiment 104, wherein said biological cell is part of an organism.

106. The method of embodiment 104, wherein said biological cell is in vitro.

107. The method of any one of embodiments 79 to 106, wherein the compound is selected from the group consisting of:

71
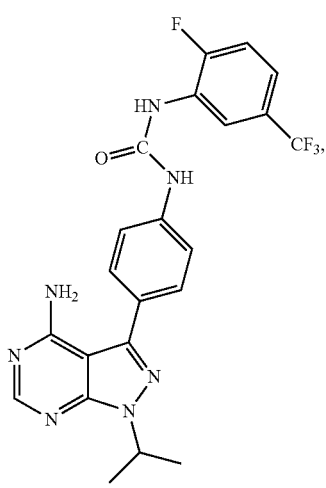
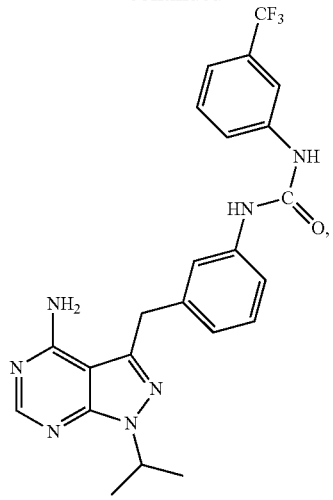
72
-continued
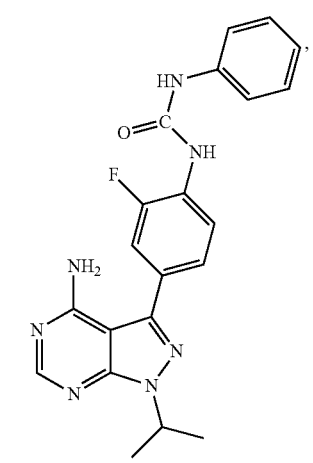
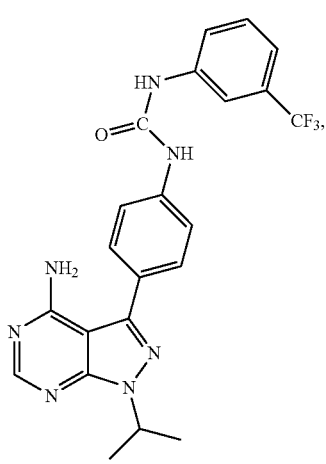

108. The method of any one of embodiments 79 to 106, wherein the compound is selected from the group consisting of:

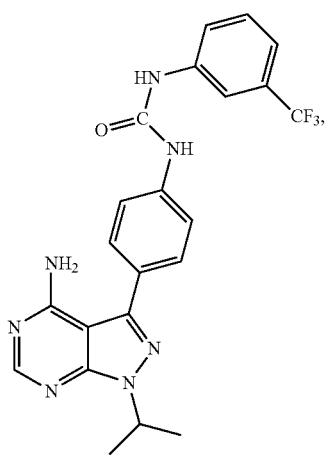

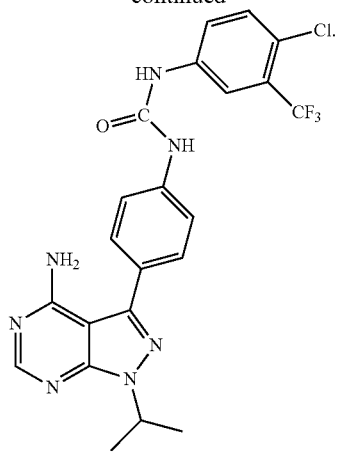

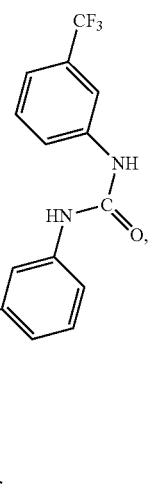

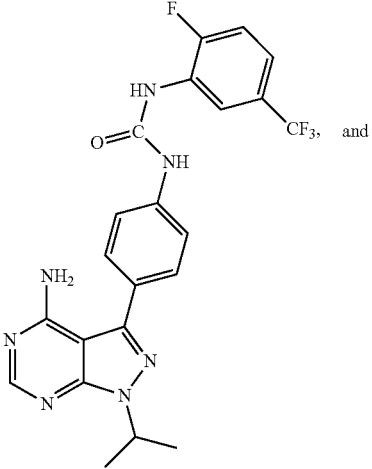

F. EXAMPLES

The following examples are meant to illustrate certain embodiments of the invention and not to limit the scope of the invention described herein.

The complexity of cancer has led to recent interest in polypharmacological approaches for developing kinase inhibitor drugs. The optimal profile of kinase inhibition remains difficult to predict and chemical optimization based on a profile of targets rather than a single target has relied on serendipity. Guided by screening in a Ret-kinase driven *Drosophila* model of Multiple Endocrine Neoplasia Type 2 (MEN2) and kinome-wide profiling of drug candidates, we identified chemically related inhibitors that target oncogenic Ret but have distinct additional kinase targets. When fed to whole flies, AD57 afforded pharmacological rescue from oncogenic Ret-induced lethality, whereas the chemical analogs AD36 and AD58 imparted reduced efficacy and enhanced toxicity, respectively. Through *Drosophila* reverse genetics and cross comparison of AD57, AD58, and AD36 profiles, we defined three pathways that account for the mechanistic basis of efficacy (targets) and dose limiting toxicity (anti-targets) in the context of oncogenic Ret: Ras, Src, and PI3K. Combinatorial inhibition of Ret plus the three downstream kinases Raf, Src, and S6K were required for optimal animal survival. Inhibition of dTor led to paradoxical hyperproliferation due to release of negative feedback; the result was high drug toxicity, demonstrating that identifying anti-targets can be particularly critical in developing cancer therapies. Chemical design based on incorporation of substituents into the phenyl-urea moiety of AD57 incompatible with dTor binding led to development of AD80 and AD81, compounds that retained the desired targets of AD57 but eliminated binding to the anti-target dTor, a feature we term 'balanced pathway inhibition'. The result was significantly improved efficacy and low toxicity in our *Drosophila* MEN2 model. Combining kinase focused chemistry, kinome-wide profiling, and *Drosophila* genetics provides a powerful approach for identifying and characterizing a complex spectrum of kinase targets that is tailored for maximal therapeutic index.

1. *Drosophila* MEN2 Model and Screen

Figure 1:
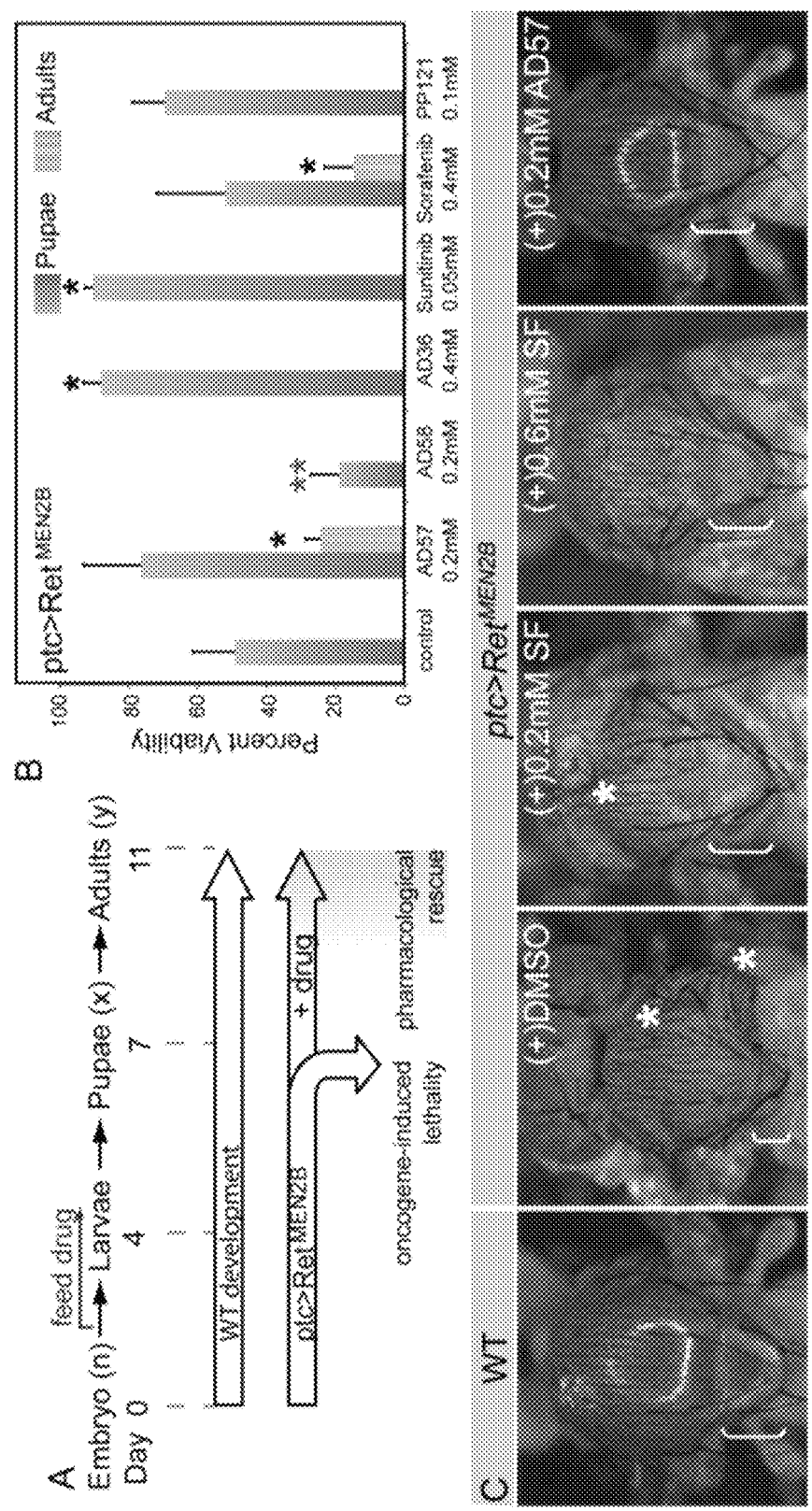
FIG. 1: Screening for an optimal therapeutic index in a *Drosophila* MEN2B model yields a polypharmacological kinase inhibitor.
Figure 1:
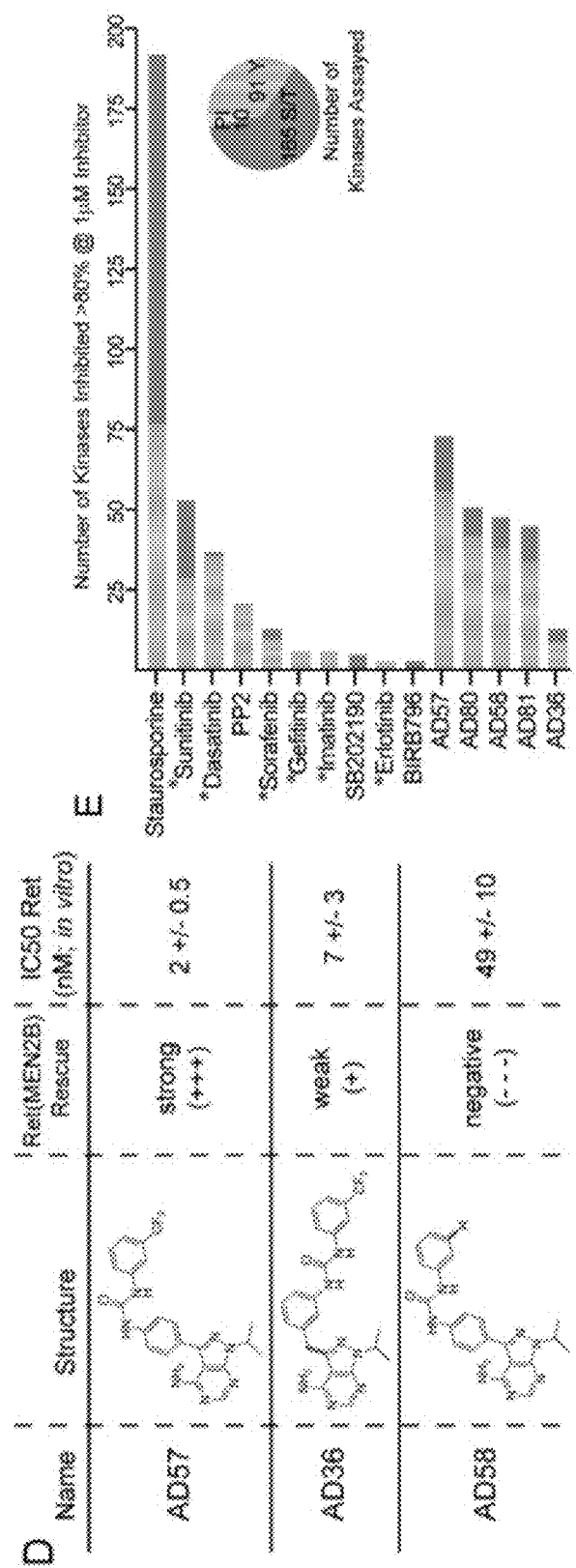

Described herein is a *Drosophila* MEN2B model in which an intracellular mutation in the *Drosophila* Ret ortholog (dRet) was targeted to the eye (Read, R. D. et al., *Genetics*, 2005. 171(3): p. 1057-81). This dRet$^{MEN2B}$ model proved useful for validating whole animal efficacy of the kinase inhibitor ZD6474/Vandetanib (Vidal, M. et al., *Cancer Res*, 2005. 65(9): p. 3538-41), a drug recently approved for MEN2 patients. To improve its utility for drug screening, we developed a more quantitative 'viability assay' that utilizes the GAL4/UAS system to target oncogenic dRet$^{MEN2B}$ to multiple developing epithelial tissues (FIG. 1A). The screen is conducted in developing drosophila embryos. Under normal circumstances, drosophila embryos pass through four developmental steps: embryo→larvae→pupae→adult. However, expression of an oncogenic form of the RET tyrosine kinase blocks 100% of embryos at the pupae stage so that none reach adulthood. We calibrated the ptc>dRetMEN2B assay to permit 50% survival to pupariation and 0% survival to adulthood. Mutated forms of RET are believed to be causative in human thyroid cancers including multiple endocrine neoplasia types 2A and 2B (MEN2A and MEN2B). The screen identifies small molecules that (a) suppress the toxicity induced by oncogenic RET and (b) allow flies to develop to functional adults. Oral administration of clinical kinase inhibitors Sunitinib and Sorafenib Wilhelm, S. M. et al., *Cancer Res,* 2004. 64(19): p. 7099-109; Sun, L. et al., *J Med Chem,* 2003. 46(7): p. 1116-9) resulted in mild (Sunitinib) or stronger (Sorafenib) rescue (FIG. 1B), validating our assay. Of note, Sorafenib rescued some animals to adulthood but did not significantly increase the proportion that developed to pupariation, indicating some efficacy but also toxicity at optimal doses.

2. Screening and Identification of AD57 Compound

We developed a library of polypharmacology-based compounds that target Ret in addition to other classes of kinases. To identify candidate compounds with optimal efficacy and toxicity profiles, we synthesized a panel of inhibitors with near equal potency against RET (a traditional target-based approach) that additionally target downstream kinases within the canonical Ret signaling pathway. We screened them with a phenotype-based screen using a *Drosophila* model of the severe disease subtype MEN2B (Read, R. D. et al., *Genetics,* 2005. 171(3): p. 1057-81). One compound was identified, AD57, that potently suppressed ptc>dRet$^{MEN2B}$ lethality in the larva and rescued approximately 25% of animals to adulthood (FIG. 1B, 1C). Rescued adults also exhibited complete suppression of notum and scutellum defects that were observed in un-enclosed control pupae (FIG. 1C). Many rescued animals were fully active and fertile. Of note, AD57 demonstrated an improved efficacy/toxicity profile in our assay compared to a panel of clinically relevant compounds including Sunitinib and Sorafenib and the recently reported (Apsel, B. et al., *Nat Chem Biol,* 2008. 4(11): p. 691-9) dual PI3K:tyrosine kinase inhibitor PP121 (FIG. 1B).

Described herein is testing AD57 stepwise in genetically modified flies, which lead to rational development of a novel class of kinase inhibitors that exhibited substantially improved efficacy and toxicity in *Drosophila* and a mouse xenograft-based MEN2 model. Our results present a novel approach to rational drug development that combines aspects of target- and phenotype-based drug discovery: it utilizes whole animal screening to both explore the mechanisms by which a drug acts and to identify an improved polypharmacological profile for suppressing tumors in vivo.

AD57 was originally developed as part of a polypharmacology-based, type II inhibitor library that targets multiple kinase classes including cytoplasmic and receptor tyrosine kinases. In a co-crystal structure with c-Src, AD57 bound to the 'DFG-OUT' conformation, a configuration that was previously considered to be energetically unfavorable and inaccessible to drugs (FIG. 9A; Ref (Dar, A. C., M. S. Lopez, and K. M. Shokat, *Chem Biol,* 2008. 15(10): p. 1015-22)).

The overall structure of AD57-like compounds includes two fragments fused through a urea linker (FIG. 1D). Shared features include a pyrazolopyrimidine core that functions as a mimic of adenosine or 'hinge binder' and a hydrophobic element that binds within an allosteric pocket of the kinase domain. The rescue profile of AD57 led us to further explore its properties.

3. Comparison of AD57 to Other Compounds and Kinase Inhibitor SAR

We also examined two close analogs of AD57. AD36 contains a methylene group between the pyrazolopyrimidine ring and fused phenyl portion that alters the relative geometry of the hinge binding and allosteric site elements (FIG. 1D). AD58 does not contain the —CF3 group that is a key pharmacophore for type II inhibition (Liu, Y. and N. S. Gray, *Nat Chem Biol,* 2006. 2(7): p. 358-64). These subtle structural changes led to significant changes in activity. AD36 exhibited some efficacy (increased pupae but no adults) whereas AD58 induced significant toxicity without detectable efficacy (fewer pupae, adults; FIG. 1B). These results demonstrate the sensitivity of whole body phenotypes in *Drosophila* to conservative structural differences between AD57, AD36 and AD58.

We reasoned that the rescue phenotype of AD57 could not solely be based upon its type II binding mode: for example, other type II kinase inhibitors such as Imatinib, Sorafenib and AD36 did not rescue to the same degree as AD57. The difference between AD36 and AD57 was especially surprising since both share near equal potency for Ret in vitro (FIG. 1D); indeed, our analysis of other kinase inhibitors indicated that efficacy did not correlate solely with inhibition of Ret (FIG. 3B). This suggested that targeting of additional kinases is necessary for the biological efficacy of AD57. Using in vitro kinase assays we tested AD57, AD36, and AD58 at 1 µM for activity against approximately one-half of the human kinome (FIG. 1E): 165 Ser/Thr kinases, 91 Tyr kinases, and 10 PI kinases were assayed, totaling 266 kinases (244 distinct kinases plus 22 mutant isoforms; see FIGS. 6-8 for measured inhibition values). This broad survey of differences in activity was instructive and indicated that small perturbations in AD57's structure led to considerable changes in kinase selectivity.

At a cutoff of greater than 80% inhibition, AD36 and AD57 inhibited the least and most kinases, respectively (FIG. 1E). For example and relevant to this work, AD57 is a potent inhibitor of human B-Raf, S6K, mTor, and Src. By comparison, AD58 is a much weaker inhibitor of S6K and B-Raf but is more potent against mTor; AD36 is a relatively selective compound that has maintained activity for Ret and Raf but is nearly inactive against mTor, S6K and Src. We explored these kinase targets in more detail below. Of note, AD36's additional methylene group eliminated its activity for a large number of kinases—most likely through steric clash at the gatekeeper position (FIG. 10): the gatekeeper mutant alleles for Abl (T315I), EGFR (T790M), and Ret (V804L) were inhibited more poorly than their wild type counterparts. In contrast, AD57 retained or improved on inhibition of gatekeeper isoforms (e.g., EGFR(T790M)).

4. AD57 Shows Efficacy in Standard Mammalian MEN2 Models

AD57 potently inhibited viability of the MEN2B patient-derived cell line MZ-CRC-1 with an IC$_{50}$ approximately 150-fold more potent than Sorafenib, a drug currently in clinical trials for MTC (FIG. 2A). AD36 and AD58 inhibited MZ-CRC-1 cell viability at levels similar to Sorafenib but well below AD57; PP121 reduced MZ-CRC-1 cell viability to levels approaching AD57 (FIG. 2A). In dose-response studies with the MEN2A-derived human TT cell line AD57 exhibited an $IC_{50}$ more than 150-fold lower than Vandetanib (FIG. 2B), a kinase inhibitor recently approved for MEN2 and MTC (Wells, S. A., Jr. et al., *J Clin Oncol,* 2010. 28(5): p. 767-72; Wells S A, R. B., Gagel R F et al., *J Clin Oncol* (Meeting Abstracts), 2010. 28(Suppl): p. 5503).

5. Compound Studies in Mouse Model of Cancer

In addition to the experiments with AD57 and AD80 in *drosophila*, we have examined these molecules in murine models of cancer. We have found that both compounds have pharmacokinetic profiles in a range that is similar to several clinical agents. We have found that AD57 displays antitumor activity in a mouse xenograft model of MEN2B cancer.

Cell culture studies provide limited efficacy and toxicity data and so we turned to a conventional mouse xenograft model. TT-based tumors were grown for 46 days in athymic nu/nu male mice prior to drug administration. Subsequent PO administration of 20 mg/kg AD57 led to significant suppression of tumor growth (FIG. 2C) at a concentration (20 mg/kg) that demonstrated no detectable toxicity as assessed by animal weights (FIG. 2D). Together our data indicate that *Drosophila* in vivo assays provide a useful tool for identifying compounds with improved efficacy and toxicity profiles while providing important information on their effects in situ.

6. Inhibition of Ret, B-Raf, Src, Tor, and S6K Kinase Activity

At least three major pathways are required for $dRet^{MEN2B}$-mediated transformation: Ras, Src, and glucose metabolism/PI3K (FIG. 3A; Ref. (Read, R. D. et al., *Genetics,* 2005. 171(3): p. 1057-81)). We utilized in vitro kinase assays to assess compound activity against relevant kinases from each of these pathways, specifically Ret, B-Raf, Src, Tor, and S6K (FIG. 3B). The three AD-class compounds exhibited differing kinase profiles. For example, AD57 and AD58 strongly inhibited Src kinase activity while AD36 inhibited it only weakly. We previously demonstrated that activation of Src is sufficient to direct many of the aspects we observed within the ptc domain (Read, R. D., E. A. Bach, and R. L. Cagan, *Mol Cell Biol,* 2004. 24(15): p. 6676-89; Vidal, M., D. E. Larson, and R. L. Cagan, *Dev Cell,* 2006. 10(1): p. 33-44; Vidal, M. et al., *Cancer Res,* 2007. 67(21): p. 10278-85) and so we explored its activity in situ.

7. Comparison of Compound Effects on Multiple Aspects of dRetMEN2-Mediated Transformation We previously developed a wing-based assay for transformation and cell migration that we utilized to explore Ras- and Src-based tumorigenesis (Vidal, M., D. E. Larson, and R. L. Cagan, *Dev Cell,* 2006. 10(1): p. 33-44). In this assay, the ptc-GAL4 driver directed oncogene expression in a stripe along the anterior-posterior axis; oncogene-based transformation led to over-proliferation, epithelial-to-mesenchymal transition (EMT), and cell migration away from the ptc domain. Adapting this approach to oncogenic dRet we found that ptc>$dRet^{MEN2B}$ wings exhibited each of these aspects (FIG. 3C; top left, arrow). Oral administration of AD57 demonstrated potent in vivo suppression of ptc>$dRet^{MEN2B}$ leading to reduced proliferation, a rescue of the EMT-like phenotype and a block in cell invasion (FIG. 3C; bottom left). Sunitinib, Vandetanib, and PP121 all showed limited ability to significantly rescue the transformation phenotype while Sorafenib, a Raf/RTK-class inhibitor, showed measurable rescue that was nonetheless less than AD57 (FIG. 1B). We conclude that oral administration of AD57 is particularly effective at suppressing dRet-mediated transformation at doses that are non-toxic to the fly.

8. Comparison of Compound Effects on Src Kinase in dRetMEN2 Model ptc>$dRet^{MEN2B}$ led to high levels of activated, phospho-Src at the basal invading front of transformed cells (FIG. 3C top left panel; star). In addition to suppressing EMT and invasion, oral administration of AD57 suppressed phospho-Src in basal regions of the wing epithelium (FIG. 3C bottom left). Distinctions with AD36 and AD58 were instructive. AD36 failed to suppress the invasion or basal migration of ptc>$dRet^{MEN2B}$ cells and, as predicted by our in vitro assay, phospho-Src remained at high levels at the basal leading edge (FIG. 3C middle panel; star). Also as predicted, AD58 prevented basal phospho-Src accumulation, yet it failed to prevent invasion/basal migration (FIG. 3C bottom right). This data support the view that Src inhibition contributes to reducing invasion/basal migration but suggest that other targets are required as well.

9. Compound Effects on Ras/Erk Pathway in dRetMEN2 Model

The adult *Drosophila* wing consists of a stereotypical pattern of four veins and two cross-veins; increased Ras/Erk pathway activity leads to ectopic veins (e.g., Refs. (Sawamoto, K. et al., *Dev Biol,* 1996. 178(1): p. 13-22; Guichard, A. et al., *Development,* 1999. 126(12): p. 2663-76)). Expression of oncogenic dRet throughout the developing wing (765>$dRet^{MEN2B}$) led to disruption of the overall adult wing pattern including ectopic wing veins (FIG. 3D). Reducing gene dosage of the erk ortholog rolled (765>$dRet^{MEN2B}$ erk−/+) suppressed these phenotypes (FIG. 3D), confirming that wing vein formation is dependent on Ras/Erk activity.

$dRet^{MEN2B}$-dependent wing phenotypes were suppressed with AD57 treatment (FIG. 3D). Surprisingly, the ectopic wing vein phenotype was slightly but consistently enhanced with AD58 treatment (FIG. 3D), suggesting that AD58 treatment increased Ras pathway signaling. Consistent with this view, removing a functional copy of erk resulted in strong suppression of $dRet^{MEN2B}$-induced wing phenotypes in the presence of AD58 treatment (FIG. 3D, 3E). Reducing erk copy number also enhanced AD57-treatment to yield wings that were nearly wild type (FIG. 3D, 3E). This data raised the possibility that AD58 toxicity was due to excess Ras pathway activity. It also indicated that further suppressing Ras signaling would improve AD57's activity profile.

10. Inhibition of the Anti-Target dTor Contributes to Whole Animal Toxicity

In addition to elevated Ras/Erk signaling, AD58 directed significant whole animal toxicity when fed to ptc>$dRet^{MEN2B}$ and wild type flies (FIG. 1B, 4A, 4B), providing us an opportunity to explore aspects of AD-class toxicity. Based on in vitro kinase data, AD58 is a stronger inhibitor of mTor and a weaker inhibitor of B-Raf than AD57 (FIG. 3B). Recently, mTor inhibition has been demonstrated to provide feedback activation to Ras pathway signaling (Gedaly, R. et al., *Anticancer Res.* 30(12): p. 4951-8; Carracedo, A. et al., *J Clin Invest,* 2008. 118(9): p. 3065-74). We therefore tested whether differences in AD57 vs. AD58 efficacy and toxicity were due in part to differences in the inhibition of the putative anti-target dTor. We refer to an 'anti-target' as a kinase where inhibition leads to a worse outcome.

Reducing dTor (ptc>$dRet^{MEN2B}$ dTor−/+) dominantly suppressed the efficacy of AD57 and enhanced the toxicity of AD58 (FIG. 4A). A quantitative phenotypic assessment indicated that enhancement of AD58 was due primarily to an increase in proliferation (FIG. 4C, 4E). Importantly, reducing the gene dosage of dTor also enhanced the AD58- induced ectopic wing pattern and vein formation (FIG. 4D) indicating that reducing dTor increased Erk activity.

We also assessed the utility of balancing dTor-Ras signaling by targeting the latter for reduction. AD58-mediated toxicity in wild type flies was almost completely suppressed by co-feeding with the RAF inhibitor Sorafenib or MEK-inhibitor AZD6244 (FIG. 4B). Combining AD58 with Sorafenib also resulted in significant suppression of invasion and migration within ptc>dRet$^{MEN2B}$ wing discs (FIG. 4F). Removing a genomic copy of erk/rolled also improved AD57's efficacy and toxicity profile (FIG. 4A). Together, these data indicate that both AD57 and AD58 act to inhibit dTor activity but failure of AD58 to suppress Raf kinase led to elevated Ras pathway activity. Elevated Erk in turn led to poor tumor efficacy and high whole body toxicity.

11. AD80 and AD81 Demonstrate an Improved Profile

Our genetic and chemical data indicated that an optimal drug for MEN2B will exhibit activity against Src, S6K, and Raf but limited activity against Tor. To improve AD57, we developed a series of new AD-based analogs that were tested for these properties through in vitro kinase assays. From our previously determined structure of AD57 in complex with c-Src we reasoned that modifying the terminal phenyl group of AD57 would selectively perturb dTor binding without altering inhibitor interactions with Ret, Raf, or Src. To test this hypothesis we generated two compounds, AD80 and AD81, in which ortho-Fluorine and para-Chlorine groups, respectively, were incorporated (FIG. 5A).

Based on their in vitro kinase profiles, AD80 and AD81 inhibited Ret, Raf, Src, and S6K but not mTor activity (FIG. 5A). Oral administration of either AD80 or AD81 resulted in a remarkable 70-90% of animals developing to adulthood in our Drosophila ptc>dRet$^{MEN2B}$ model, a significant improvement over the efficacy observed with AD57 and all other compounds we have tested to date (FIG. 5B). In the wing, both compounds displayed significantly improved suppression of dRet$^{MEN2B}$-induced proliferation, EMT, and invasion/migration, restoring normal tissue architecture (FIG. 5F). Focusing on AD80, ectopic Src activation (FIG. 5C) and wing vein pattern phenotypes (FIG. 5E, F) were suppressed indicating that Src and Ras activities were restored to normal levels. The result was phenotypically normal ptc>dRet$^{MEN2B}$ adults exceeding AD57- or Sorafenib-rescued adults, which displayed some cuticle defects.

Importantly, while reducing erk gene dosage (ptc>dRet$^{MEN2B}$ erk−/+) considerably enhanced the efficacy of AD57 and AD58 in viability assays it did not alter efficacy of AD80 treatment (FIG. 5D). This indicates that AD80 demonstrates optimal Ras-Erk pathway inhibition and, more broadly, AD80 and AD81 have an optimal balance of activity against Ret, Raf, Src, Tor, and S6K that leads to high efficacy with very low toxicity.

12. Experimental Analysis

Using a step-wise approach that combined genetics and medicinal chemistry, we identified AD57 and its derivatives AD80 and AD81 as polypharmacology agents that were optimized to inhibit a spectrum of five kinases. Our studies indicate these drugs may be an improvement over existing compounds including Vandetanib, a kinase inhibitor demonstrated by others and us to act on Ret-based tumorigenesis (Vidal, M. et al., Cancer Res, 2005. 65(9): p. 3538-41; Carlomagno, F. et al., Cancer Res, 2002. 62(24): p. 7284-90) and recently approved for MTC patients. Here, we focused on a library of compounds designed for multi-kinase targeting (Ref. (Dar, A. C., M. S. Lopez, and K. M. Shokat, Chem Biol, 2008. 15(10): p. 1015-22)) to improve our chances of identifying useful polypharmacological hits. A related approach is to assess drug combinations; we are also exploring combinations using a similar approach. A collaborative agreement between Merck and AstraZeneca to combine a MEK inhibitor (AZD6244) with an Akt inhibitor (MK-2206) suggests that commercial or trial design barriers for combined therapies are yielding (Knight, Z. A., H. Lin, and K. M. Shokat, Nat Rev Cancer, 10(2): p. 130-7). In addition to the increased cost of producing a mix of compounds, complex target profile interactions and differing pharmacokinetics can make executing clinical trials challenging.

An important point that emerges from these studies is the inadequacy of using potency against the primary oncogene, Ret, to predict a drug's whole animal efficacy. This is surprising, as all phenotypes in our model are due to oncogenic Ret, the sole initiator of tumors in most MEN2 patients. This observation is consistent with the observation that certain drugs that proved potent against Ret and against human MEN2 cell lines have nevertheless shown limited success and substantial toxicity in clinical trials (e.g., Ref. (Verbeek, H. H. et al., J Clin Endocrinol Metab, 2011. 96(6): p. E991-5; Ahmed, M. et al., Eur J Endocrinol, 2011)). At least two reasons are likely to explain this discrepancy. First, strong inhibition of Ret may prove toxic both due to on-target and the inevitable off-target effects across body systems (Durante, C. et al., Expert Opin Investig Drugs, 2011. 20(3): p. 407-413); adding drugs directly to a cell line likely gives it direct access to oncogenic Ret but achieving similar concentrations throughout a body may require toxic doses. Whereas, partial inhibition of multiple kinases may permit sufficient function within non-diseased tissues while preventing the high levels of kinase activity required to sustain and progress a tumor.

13. Balanced Pathway

We defined three pathways that account for the mechanistic basis of efficacy (targets) and dose limiting toxicity (anti-targets) in the context of oncogenic Ret: Ras, Src, and PI3K. Combinatorial inhibition of Ret plus the three downstream kinases Raf, Src, and S6K were required for optimal animal survival. Inhibition of dTor led to paradoxical hyperproliferation due to release of negative feedback; the result was high drug toxicity, demonstrating that identifying anti-targets can be critical in developing cancer therapies. Chemical design based on incorporation of substituents into the phenyl-urea moiety of AD57 incompatible with dTor binding led to development of AD80 and AD81, compounds that retained the desired targets of AD57 but eliminated binding to the anti-target dTor, a feature we term 'balanced pathway inhibition'. The result was significantly improved efficacy and low toxicity in both Drosophila and mammalian MEN2 models.

Based on their in vitro kinase profiles AD80 and AD81 inhibited Ret, Raf, Src, and S6K, with greatly reduced mTor activity relative to AD57 and AD58 (FIG. 5A). Oral administration of either AD80 or AD81 resulted in a remarkable 70-90% of animals developing to adulthood in our Drosophila ptc>dRet$^{MEN2B}$ model, a significant improvement over the efficacy observed with AD57 and all other compounds we have tested to date (FIG. 5B). In the wing, both compounds displayed significantly improved suppression of dRet$^{MEN2B}$-induced proliferation, basal constriction, and invasion/migration, restoring normal tissue architecture (FIG. 5F). Focusing on AD80, ectopic Src activation (FIG. 5C) and wing vein pattern phenotypes (FIG. 5E, F) were strongly suppressed indicating that Src and Ras activities were restored to normal levels. The result was phenotypically normal ptc>dRet$^{MEN2B}$ adults with phenotypic rescue that exceeded AD57 or Sorafenib, which yielded adults with some cuticle defects.

The improved profile of AD80 also translated to mammalian MEN2 models. AD80 inhibited proliferation of MZ and TT thyroid cancer cells in culture (FIG. 18A, B), most likely through the induction of apoptosis (FIG. 19). Immunoblot analysis demonstrated potent downregulation of phospho-Ret and several downstream biomarkers within these cells FIG. 20). Finally, we observed enhanced tumor growth inhibition and reduced body weight modulation relative to Vandetanib in a mouse xenograft model (FIG. 18C, D).

The connection between Tor and the Ras pathway within the MEN2B model is reminiscent of a general network motif termed an incoherent feed-forward loop (Durante, C. et al., *Expert Opin Investig Drugs*, 2011. 20(3): p. 407-413): here, dRet$^{MEN2B}$ activates Ras but also represses Ras signaling by activating Tor. This network motif has been identified within diverse contexts including transcriptional and neuronal networks as a means to tune cellular responses to incoming signals (Durante, C. et al., *Expert Opin Investig Drugs*, 2011. 20(3): p. 407-413).

14. Inhibition of RET Fusion Proteins

As shown in FIGS. 23-25, cells expressing RET fusions (e.g. having aberrant Ret activity or function), inhibition of RET signaling leads to reduction of proliferation at concentrations about 100-fold higher than those required to induce dephosphorylation of the driver oncogene and its downstream signaling. Furthermore, over time, PI3K and MAPK signaling can be reactivated in a RET-independent manner and thus consequently combination of RET and MEK inhibition lead to robust induction apoptosis in these cells. Combination therapies using Ret inhibitors (e.g. compounds described herein) and MEK-targeted therapies or therapeutics may be of clinical relevance for patients with cancers associated with aberrant Ret activity or function or levels (e.g. thyroid cancers expressing RET-fusion proteins (e.g. CCDC6-RET) or lung cancers expressing such oncogenically active RET fusions (e.g. KIF5B-RET).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating cancer in a subject in need thereof, wherein said cancer is thyroid cancer, familial medullary thyroid cancer, medullary thyroid carcinoma, pheochromocytoma, primary hyperparathyroidism, parathyroid hyperplasia, or papillary thyroid cancer, said method comprising administering to the subject an effective amount of a compound having the formula:

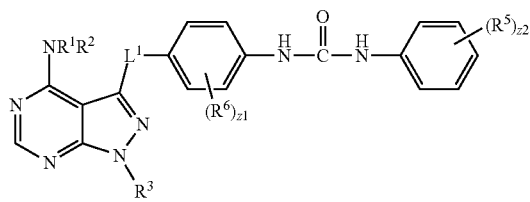

(I)

or

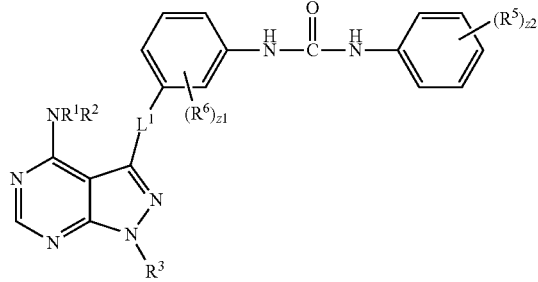

(II)

wherein $R^1$ and $R^2$ are independently hydrogen or substituted or unsubstituted alkyl;

$R^3$ is independently substituted or unsubstituted alkyl;

$R^5$ is independently halogen, —CN, —CX$^a$$_3$, —S(O)$_2$H, —NO, —NO$_2$, —C(O)H, —C(O)NH$_2$, —S(O)$_2$NH$_2$, —OH, —SH, —SO$_2$Cl, —SO$_3$H, —SO$_4$H, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, —CO$_2$H, or substituted or unsubstituted (C$_1$- C$_6$) alkyl;

$R^6$ is independently halogen, —CN, —CX$^b$$_3$, —S(O)$_2$H, —NO, —NO$_2$, —C(O)H, —C(O)NH$_2$, —S(O)$_2$NH$_2$, —OH, —SH, —SO$_2$Cl, —SO$_3$H, —SO$_4$H, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, or —CO$_2$H;

$L^1$ is independently a bond or substituted or unsubstituted alkylene;

z1 is independently an integer from 0 to 4;

z2 is independently an integer from 0 to 5; and $X^a$ and $X^b$ are independently —F, —Cl, —Br, or —I; and wherein treating cancer is amelioration of cancer disease, cancer injury, cancer pathology, or cancer condition.

2. The method of claim 1, wherein $R^1$ is hydrogen.

3. The method of claim 1, wherein $L^1$ is a bond.

4. The method of claim 1, wherein $L^1$ is methylene.

5. The method of claim 1, wherein $R^3$ is substituted or unsubstituted alkyl.

6. The method of claim 1, wherein $R^5$ is halogen, —CN, —CX$^a$$_3$, —NO, —NO$_2$, —C(O)H, or —CO$_2$H.

7. The method of claim 1, wherein $R^6$ is halogen, —CN, —CX$^b$$_3$, —NO, —NO$_2$, —C(O)H, or —CO$_2$H.

8. The method of claim 1, wherein $R^6$ is halogen.

9. The method of claim 1, wherein z1 is 0.

10. The method of claim 1, wherein z2 is 2.

11. The method of claim 1, wherein the compound has the formula

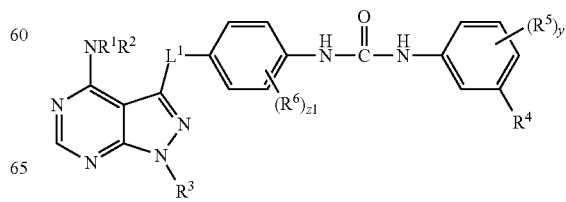

(III)

or

-continued

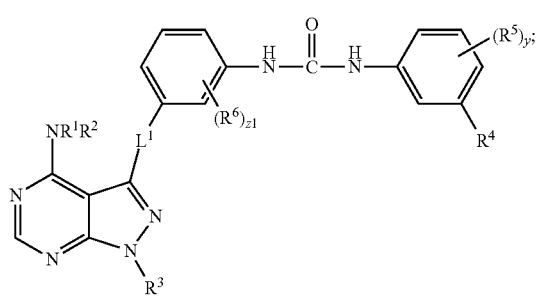

wherein
R[4] is independently halogen, —CN, —CX$_3$, —S(O)$_2$H, —NO, —NO$_2$, —C(O)H, —C(O)NH$_2$, —S(O)$_2$NH$_2$, —OH, —SH, —SO$_2$Cl, —SO$_3$H, —SO$_4$H, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OC$_3$, —OCHF$_2$, —CO$_2$H, or substituted or unsubstituted (C$_1$-C$_6$) alkyl;
y is independently an integer from 0 to 4; and
X is independently —F, —Cl, —Br, or —I.

12. The method of claim 11, wherein R[4] is halogen, —CN, —CX$_3$, —NO, —NO$_2$, —C(O)H, or —CO$_2$H.

13. The method of claim 11, wherein y is 1.

14. The method of claim 1, wherein the compound has a formula selected from the group consisting of:

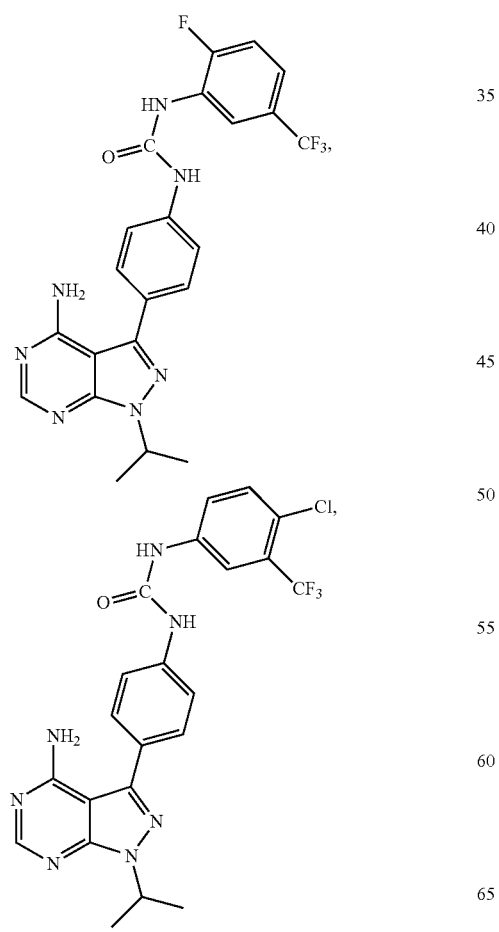

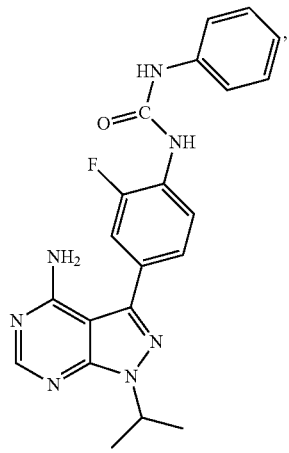

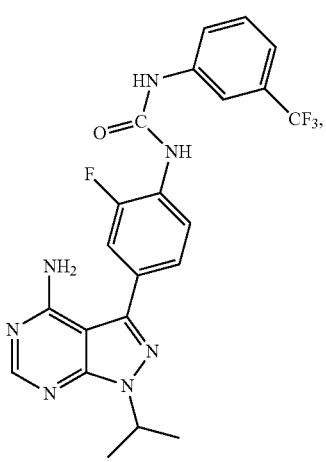

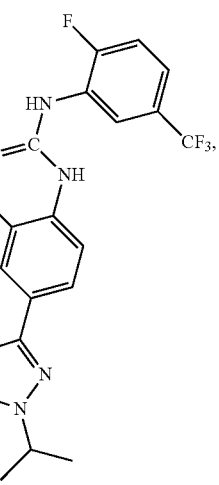

-continued
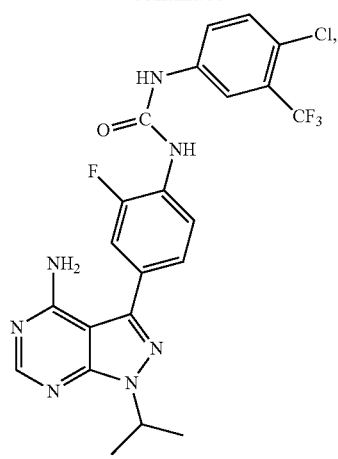
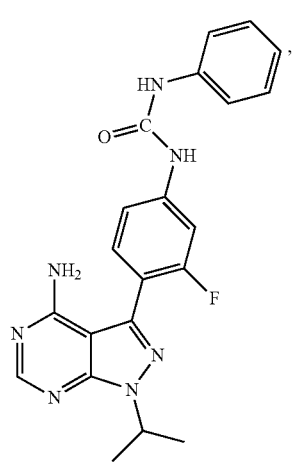
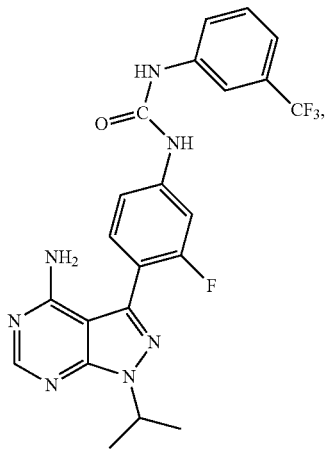
-continued
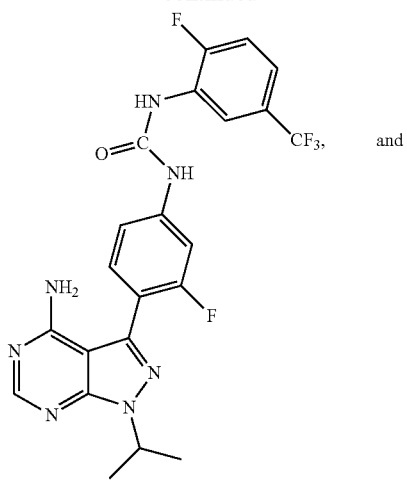
and
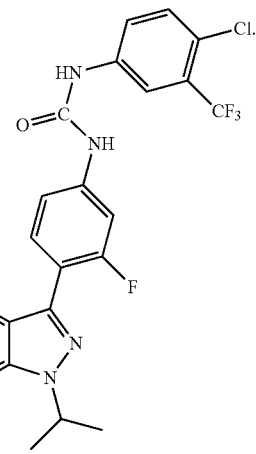
15. The method of claim 13, wherein the compound has a formula selected from the group consisting of:
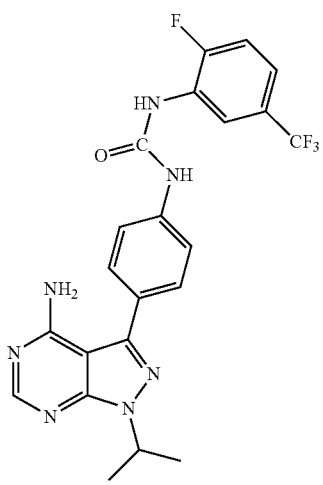
and -continued

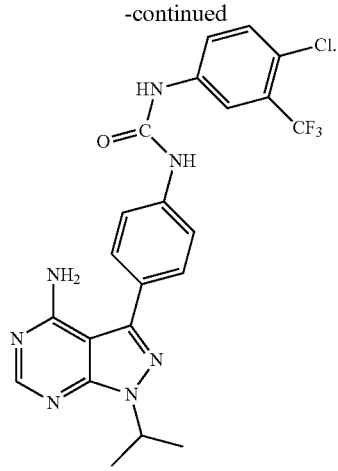

16. The method of claim 1, wherein said cancer is resistant to an anti-cancer agent.

17. The method of claim 16, wherein said anti-cancer agent is an EGFR-targeted therapy or therapeutic.

18. The method of claim 1, further comprising administering to said subject a therapeutically effective amount of an anti-cancer agent.

19. The method of claim 18, wherein said anti-cancer agent is an EGFR-targeted therapy or therapeutic.

* * * * *